US012559514B2

(12) United States Patent
Armiger et al.

(10) Patent No.: US 12,559,514 B2
(45) Date of Patent: Feb. 24, 2026

(54) SYNTHESIS OF FLUORINATED NUCLEOTIDES

(71) Applicant: Merck Sharp & Dohme LLC, Rahway, NJ (US)

(72) Inventors: Travis Armiger, Jersey City, NJ (US); Kevin M. Belyk, Metuchen, NJ (US); Tamas Benkovics, East Brunswick, NJ (US); Cheol K. Chung, Westfield, NJ (US); Yining Ji Chen, Clark, NJ (US); Heather Claire Johnson, New Brunswick, NJ (US); Artis Klapars, Edison, NJ (US); Zhijian Liu, Kendall Park, NJ (US); Zhuqing Liu, Acton, MA (US); Jeffrey C. Moore, Westfield, NJ (US); Andrew J. Neel, Jersey City, NJ (US); Feng Peng, Dayton, NJ (US); Stephan M. Rummelt, Lorrach (DE); Nastaran Salehi Marzuarani, Edgewater, NJ (US); Benjamin D. Sherry, Brooklyn, NY (US); Zhiguo Jake Song, Edison, NJ (US); Ben William Hulme Turnbull, Jersey City, NJ (US); Lu Wang, Scotch Plains, NJ (US); Feng Xu, Staten Island, NY (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 608 days.

(21) Appl. No.: 17/923,784

(22) PCT Filed: May 20, 2021

(86) PCT No.: PCT/US2021/033286
§ 371 (c)(1),
(2) Date: Nov. 7, 2022

(87) PCT Pub. No.: WO2021/236859
PCT Pub. Date: Nov. 25, 2021

(65) Prior Publication Data

US 2023/0174567 A1 Jun. 8, 2023

Related U.S. Application Data

(60) Provisional application No. 63/028,741, filed on May 22, 2020.

(51) Int. Cl.

| | |
|---|---|
| ***C07H 19/10*** | (2006.01) |
| ***C07H 1/00*** | (2006.01) |
| ***C07H 19/06*** | (2006.01) |
| ***C12P 19/32*** | (2006.01) |

(52) U.S. Cl.
CPC ............... *C07H 19/10* (2013.01); *C07H 1/00* (2013.01); *C07H 19/06* (2013.01); *C12P 19/32* (2013.01)

(58) Field of Classification Search
None
See application file for complete search history.

(56) References Cited

U.S. PATENT DOCUMENTS

| | | | | |
|---|---|---|---|---|
| 5,681,702 | A | 10/1997 | Collins et al. | |
| 6,395,710 | B1 | 5/2002 | Chu et al. | |
| 10,106,574 | B2 * | 10/2018 | Altman | C07H 19/20 |
| 10,738,074 | B2 * | 8/2020 | Altman | C07H 19/20 |

(Continued)

FOREIGN PATENT DOCUMENTS

| | | | |
|---|---|---|---|
| CN | 103819524 | A | 5/2014 |
| EP | 0381335 | A1 | 8/1990 |

(Continued)

OTHER PUBLICATIONS

Altschul S.F. et al., Gapped BLAST and PSI-BLAST: a new generation of protein database search programs, Nucleic Acids Research, 1997, 3389-3402, 25-17, Oxford University Press.

(Continued)

*Primary Examiner* — Patrick T Lewis
(74) *Attorney, Agent, or Firm* — Julie M. Lake; Catherine D. Fitch

(57) ABSTRACT

The present invention relates to efficient processes useful in the preparation of fluorinated nucleosides, such as (2S,3R,4S,5R)-5-(2-amino-6-oxo-1,6-dihydro-9H-purin-9-yl)-3-fluoro-4-hydroxy-2-(mercaptomethyl)tetrahydrofuran-3-yl dihydrogen phosphate, also known as 3'-fluoro-thio-guanosine monophosphate or 3'-F-thio-GMP. Such fluorinated nucleosides may be useful as a biologically active compound and or as an intermediate for the synthesis of more complex biologically active compounds. The present invention also encompasses intermediates useful in the disclosed synthetic processes and the methods of their preparation. (I)

(I)

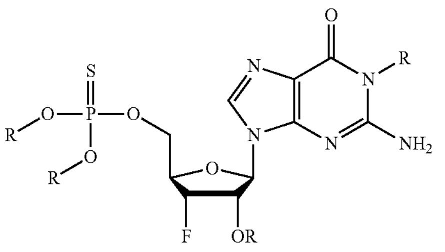

22 Claims, No Drawings

Specification includes a Sequence Listing.

(56) References Cited

U.S. PATENT DOCUMENTS

2018/0127749 A1 5/2018 Vornlocher et al.
2018/0168208 A1 6/2018 McGrane et al.

FOREIGN PATENT DOCUMENTS

WO 2002032920 A2 4/2002
WO 2018118665 A1 6/2018

OTHER PUBLICATIONS

Altschul, Stephen F. et al., Basic Local Alignment Search Tool, J. Mol. Biol., 1990, 403-410, 215.

Balzarini, Jan et al., Anti-Retrovirus Activity of 3'-Fluoro- and 3' -Azido-Substituted Pyrimidine 2' ,3'-Dideozynucleoside Analogues, Biochemical Pharmacology, 1988, 2847-2856, vol. 37. No. 14.

Berge, S.M., et al.,, "Pharmaceutical Salts", J. Pharm. Sci, 1977, pp. 1-19, vol. 66, No. 1.

Eisenberg, D. et al., Analysis of Membrane and Surface Protein Sequences with the Hydrophobic Moment Plot, J. Mol. Biol., 1984, 125-142, 179.

Fleet, George W. J. T Al., Methyl 5-O-Tert-Butyldiphenylsilyl-2-Deoxy-αβ-D-Threo-Pentofuranoside as a Divergent Intermediate for the Synthesis of 3'-Substituted-2',3'-Dideoxynucleosides:, Tetrahedron, 1988, 625-636, 44(2).

Fox, J.J. et al., Antiviral Activities of 2'-Fluorinated Arabinosyl-Pyrimidine Nucleosides, Fluorinated Carbohydrates—Chemical and Biochemical Aspects, ACS Symposium Series, 1988, 176-190, Chapter 10, vol. 374.

Gould, Salt selection for basic drugs, International J. of Pharmaceutics, 1986, 201-217, 33.

Henikoff, Steven, Amino acid substitution matrices from protein blocks, Proc. Natl. Acad. Sci. USA, Biochemistry, 1992, 10915-10919, 89.

Herdewijn, Piet et al., 3'-Substituted 2', 3'-Dideoxynucleoside Analogues as Potential Anti-HIV (HTLV-III/LAV) Agents, Journal of Medicinal Chemistry, 1987, 1270-1278, 30(8).

Herdewijn, Piet et al., Synthesis and Anti-HIV Activity of Different Sugar-Modified Pyrimidine and Purine Nucleosides, J. Med. Chem., 1988, 2040-2048, 31.

Matthes, E. et al., Phosphorylation, Anti-HIV Activity and Cytotoxicity of 3'- Fluorothymidine, Biochemical and Biophysical Research Communications, 1988, 825-831, 153(2).

Needleman, Saul. B. et al., A General Method Applicable to the Search for Similarities in the Amino Acid Sequence of Two Proteins, J. Mol. Biol., 1970, 443-453, 48.

Pearson W.R. et al., Improved tools for biological sequence comparison, Biochemistry, 1988, 2444-2448, 85, Proc. Natl. Acad. Sci. USA.

Ren, Hang et al., Versatile synthesis and biological evaluation of novel 3'-fluorinated purine nucleosides, Beilstein J. Org. Chem., 2015, 2509-2520, 11.

Smith, Temple F. et al., Comparison of Biosequences, Adv. Appl. Math., 1981, 482-489, 2.

* cited by examiner

SYNTHESIS OF FLUORINATED NUCLEOTIDES

CROSS-REFERENCE TO RELATED APPLICATIONS

This application is a National Stage application of International Patent Application No. PCT/US2021/033286, filed May 20, 2021, which claims priority to U.S. Provisional Patent Application No. 63/028,741, filed May 22, 2020.

FIELD OF THE INVENTION

The present invention relates to efficient synthetic processes useful in the preparation of fluorinated nucleotides, such as (trisodium O-{[(2R,3S,4S,5R)-5-(2-amino-6-oxido-9H-purin-9-yl)-3-fluoro-4-hydroxyoxolan-2yl]methyl} phosphorothioate hydrate (1:6)), also known as 3'-fluoro-thio-guanosine monophosphate or 3'-F-thio-GMP. Such fluorinated nucleotides may be useful as biologically active compounds and or as intermediates for the synthesis of more complex biologically active compounds. The present invention also encompasses intermediates useful in the disclosed synthetic processes and the methods of their preparation.

REFERENCE TO SEQUENCE LISTING SUBMITTED ELECTRONICALLY

The sequence listing of the present application is submitted electronically via EFS-Web as an ASCII-formatted sequence listing, with a file name of "24997WOPCT-SEQ-TEXT-14 May 2021.txt", creation date of May 14, 2021, and a size of 24 KB. This sequence listing submitted via EFS-Web is part of the specification and is herein incorporated by reference in its entirety.

BACKGROUND OF THE INVENTION

The synthesis of complex nucleotides and nucleosides continue to challenge the synthetic community, notwithstanding many years of attempts motivated by their medicinal importance. J. J. Fox, et al., Chapter 10*: Antiviral Activities of* 2'*-Fluorinated Arabinosyl-Pyrimidine Nucleosides*, in Fluorinated Carbohydrates—Chemical and Biochemical Aspects, ACS Symposium Series, Vol. 374, 176-190 (1988). Nucleosides containing fluorine stereocenters can greatly enhance the desired biological activity of such nucleosides. For example, the introduction of fluorine to the 3' position of the sugar moiety has been found to lead to more potent antiviral agents. However, the introduction of such stereocenters adds another level of difficulty beyond the already challenging synthesis. See, e.g., Piet Herdewijn et al., 31(10) J. Med. Chem. 2040-2048 (1988); Jan Balzarini et al., 37(14) Biochem. Pharmacol. 2847-2856 (1988); George W. J. Fleet et al., 44(2) Tetrahedron 625-636 (1988); E. Matthes et al., 153(2) Biochem. Biophys. Res. Commun. 825-831 (1988); and Piet Herdewijn et al., 30(8) J. Med. Chem. 1270-1278 (1987). Early approaches suffered from poor yields and required manipulation of protecting groups at several steps.

A new strategy for the synthesis of 3'-fluorinated purine nucleosides was disclosed in 2014, by Hao-yun An et al. in Chinese Patent Application Publication CN103819524 (published May 28, 2014). This synthesis uses xylose as a starting material and provides the N-alkyl-3'-fluoroguanine with improved yields. See CN102819524; Hang Ren et al., 11 Beilstein J. Org. Chem. 2509-2520 (2015).

While these syntheses were promising as improved methods for the preparation of fluorinated nucleobase analogs, they employ lengthy synthetic sequences, among other disadvantages. Thus, there remains a need for improved syntheses of 3'-fluorinated nucleosides, and in particular 3'-F-thio-GMP nucleotide.

SUMMARY OF THE INVENTION

The present disclosure relates to processes useful in the synthesis of 3'-fluorinated nucleotides, particularly 3'-F-thio-GMP. The present disclosure also encompasses chemical processes that afford intermediates useful in the production of 3'-F-thio-GMP. The chemical processes of the present disclosure afford advantages over previously known procedures and include a more efficient route to 3'-fluorinated nucleotides starting from readily available starting materials such as guanosine. The synthetic strategy uses an isolable 2'-keto-nucleoside that undergoes stereoselective electrophilic fluorination at the 3' position. Subsequent ketone reduction proceeds with improved diastereoselectivity, and quinine-catalyzed thiophosphorylation produces 3'-fluorinated nucleotides, such as 3'-F-thio-GMP, that demonstrate selectivity for 5'-thiophosphorylation. These processes, described in further detail herein, provide a shorter synthetic route. Additionally, these processes use inexpensive raw materials, avoid the use of corrosive and hazardous bis(2-methoxyethyl) aminosulfur trifluoride (BAST) to install fluorine, use organocatalysts to control selectivity in two key steps, and proceed exclusively through stable, crystalline intermediates.

Other embodiments, aspects and features of the present disclosure are either further described in or will be apparent from the ensuing description, examples and appended claims.

DETAILED DESCRIPTION OF THE INVENTION

Definitions

Certain technical and scientific terms are specifically defined below. Unless specifically defined elsewhere in this document, all other technical and scientific terms used herein have the meaning commonly understood by one of ordinary skill in the art to which this disclosure relates. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "-O-alkyl," etc.

As used herein, and throughout this disclosure, the following terms, unless otherwise indicated, shall be understood to have the following meanings:

As used herein, including the appended claims, the singular forms of words, such as "a," "an," and "the," include their corresponding plural references unless the context clearly dictates otherwise. In particular, "a," "an," and "the" item each include a single item selected from a list as well as mixtures of two or more items selected from the list.

As used herein, the terms “at least one” item or “one or more” item each include a single item selected from the list as well as mixtures of two or more items selected from the list. For example, “at least one ketoreductase type enzyme” (alternatively referred to as “ketoreductase type enzymes”) refers to a single ketoreductase type enzyme as well as to mixtures of two or more different ketoreductase type enzymes. Similarly, the terms “at least two” items and “two or more” items each include mixtures of two items selected from the list as well as mixtures of three or more items selected from the list.

“Consists essentially of,” and variations such as “consist essentially of” or “consisting essentially of,” as used throughout the specification and claims, indicate the inclusion of any recited elements or group of elements, and the optional inclusion of other elements, of similar or different nature than the recited elements, that do not materially change the basic or novel properties of the specified dosage regimen, method, or composition.

Throughout this specification and claims, the word “comprise,” or variations such as “comprises” or “comprising” will be understood to imply the inclusion of a stated element or group of elements but not the exclusion of any other element or group of elements. In the case of integers, the word “comprise,” or variations such as “comprises” or “comprising” will be understood to imply the inclusion of a stated integer or group of integers but not the exclusion of any other integer or group of integers. Unless otherwise required by context, singular terms shall include pluralities and plural terms shall include the singular. Any example(s) following the term “e.g.” or “for example” is not meant to be exhaustive or limiting. It is understood that wherever embodiments are described herein with the language “comprising,” otherwise analogous embodiments described in terms of “consisting of” and/or “consisting essentially of” are also provided.

Unless expressly stated to the contrary, all ranges cited herein are inclusive, i.e., the range includes the values for the upper and lower limits of the range as well as all values in between. All ranges also are intended to include all included sub-ranges, although not necessarily explicitly set forth. For example, temperature ranges, percentages, ranges of equivalents, and the like described herein include the upper and lower limits of the range and any value in the continuum there between. Numerical values provided herein, and the use of the term “about”, may include variations of ±1%, ±2%, ±3%, ±4%, ±5%, and ±10% and their numerical equivalents. “About” when used to modify a numerically defined parameter means that the parameter may vary by as much as 10% below or above the stated numerical value; where appropriate, the stated parameter may be rounded to the nearest whole number. For example, an amount of about 5 mg may vary between 4.5 mg and 5.5 mg. In addition, the term “or,” as used herein, denotes alternatives that may, where appropriate, be combined; that is, the term “or” includes each listed alternative separately as well as their combination.

The term “alkyl,” as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl, and neohexyl. In one embodiment, an alkyl group is linear. In another embodiment, an alkyl group is branched.

The terms “halogen” and “halo,” as used herein, means —F (fluorine), —Cl (chlorine), —Br (bromine) or —I (iodine).

The term “haloalkyl,” as used herein, refers to an alkyl group as defined above, wherein one or more of the alkyl group’s hydrogen atoms has been replaced with a halogen. In one embodiment, a haloalkyl group has from 1 to 6 carbon atoms. In another embodiment, a haloalkyl group has from 1 to 3 carbon atoms. In another embodiment, a haloalkyl group is substituted with from 1 to 3 halogen atoms. Non-limiting examples of haloalkyl groups include $—CH_2F$, $—CHF_2$, and $—CF_3$. The term “$C_1$-$C_4$ haloalkyl” refers to a haloalkyl group having from 1 to 4 carbon atoms.

The term “alkoxy” as used herein, refers to an —O-alkyl group, wherein an alkyl group is as defined above. Non-limiting examples of alkoxy groups include methoxy, ethoxy, n-propoxy, isopropoxy, n-butoxy, and tert-butoxy. An alkoxy group is bonded via its oxygen atom to the rest of the molecule.

The term “aryl,” as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

When a functional group in a compound is termed “protected,” that functional group is in modified form to preclude undesired side reactions at the protected site when the compound is subjected to a reaction. The term “PG”, as used herein, refers to a protecting group. Those skilled in the art will readily envisage protecting groups suitable for use in compounds and processes according to the disclosure. Suitable protecting groups will be recognized by those of ordinary skill in the art as well as by reference to standard textbooks such as, for example, Green’s Protective Groups in Organic Synthesis ($5^{th}$ ed., Peter G. M. Wuts ed., 2014). Protecting groups suitable for use in the processes disclosed herein include acid-labile protecting groups. Non-limiting examples of PG suitable for use herein include $—S(O)_2R^8$, $—C(O)OR^8$, $—C(O)R^8$, $—CH_2OCH_2CH_2SiR^8$, and $—CH_2R_8$, wherein $R^8$ is selected from the group consisting of $—C_{1-8}$ alkyl (straight or branched), $—C_{3-8}$ cycloalkyl, $—CH_2$(aryl), and $—CH(aryl)_2$, wherein each aryl is independently phenyl or naphthyl and each said aryl is optionally independently unsubstituted or substituted with one or more (e.g., 1, 2, or 3) groups independently selected from $—OCH_3$, —Cl, —Br, and —I.

The term “substituted” means that one or more hydrogens on the atoms of the designated moiety are replaced with a selection from the indicated group, provided that the atoms’ normal valencies under the existing circumstances are not exceeded, and that the substitution results in a stable compound. Combinations of substituents and/or variables are permissible only if such combinations result in stable compounds. By “stable compound” or “stable structure” is meant a compound that is sufficiently robust to survive isolation to a useful degree of purity from a reaction mixture, and formulation into an efficacious therapeutic agent.

When any substituent or variable occurs more than one time in any compound, its definition on each occurrence is independent of its definition at every other occurrence, unless otherwise indicated. For example, description of radicals that include the expression “$—N(C_1$-$C_3$ alkyl$)_2$”

means $—N(CH_3)(CH_2CH_3)$, $—N(CH_3)(CH_2CH_2CH_3)$, and $—N(CH_2CH_3)(CH_2CH_2CH_3)$, as well as $—N(CH_3)_2$, $—N(CH_2CH_3)_2$, and $—N(CH_2CH_2CH_3)_2$.

It should also be noted that any carbon or heteroatom with unsatisfied valences in the text, schemes, examples, and tables herein is assumed to have sufficient hydrogen atom(s) to satisfy the valences. Any one or more of these hydrogen atoms can be deuterium.

The present disclosure also embraces isotopically-labelled compounds that are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{123}I$, respectively.

Certain isotopically-labelled compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Isotopic substitution at a site where epimerization occurs may slow or reduce the epimerization process and thereby retain the more active or efficacious form of the compound for a longer period of time. Isotopically labeled compounds, in particular those containing isotopes with longer half-lives ($T_{1/2}>1$ day), can generally be prepared by following procedures analogous to those disclosed in the Schemes and/or in the Examples herein below, by substituting an appropriate isotopically labeled reagent for a non-isotopically labeled reagent.

Compounds herein may contain one or more stereogenic centers and can occur as racemates, racemic mixtures, single enantiomers, diastereomeric mixtures, and individual diastereomers. Additional asymmetric centers may be present depending upon the nature of the various substituents on the molecule. Each such asymmetric center will independently produce two optical isomers, and all possible optical isomers and diastereomers in mixtures and as pure or partially purified compounds are included within the disclosure. Any formulas, structures, or names of compounds described herein that do not specify a particular stereochemistry are meant to encompass any and all existing isomers as described above and mixtures thereof in any proportion. When stereochemistry is specified, the disclosure is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of chiral HPLC column.

All stereoisomers (for example, geometric isomers, optical isomers, and the like) of disclosed compounds (including those of the salts and solvates of compounds as well as the salts, solvates, and esters of prodrugs), such as those that may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of compounds may, for example, be substantially free of other isomers, or may be admixed, for example, as racemates or with all other, or other selected, stereoisomers. The chiral centers can have the S or R configuration as defined by the IUPAC 1974 Recommendations.

The present disclosure further includes compounds and synthetic intermediates in all their isolated forms. For example, the above-identified compounds are intended to encompass all forms of the compounds such as, any solvates, hydrates, stereoisomers, and tautomers thereof.

Those skilled in the art will recognize that chiral compounds, and in particular, in sugars, can be drawn in a number of different ways that are equivalent. Those skilled in the art will further recognize that the identity and regiochemical position of the substituents on ribose can vary widely and that the same principles of stereochemical equivalence apply regardless of substituent. Non-limiting examples of such equivalence include those exemplified below.

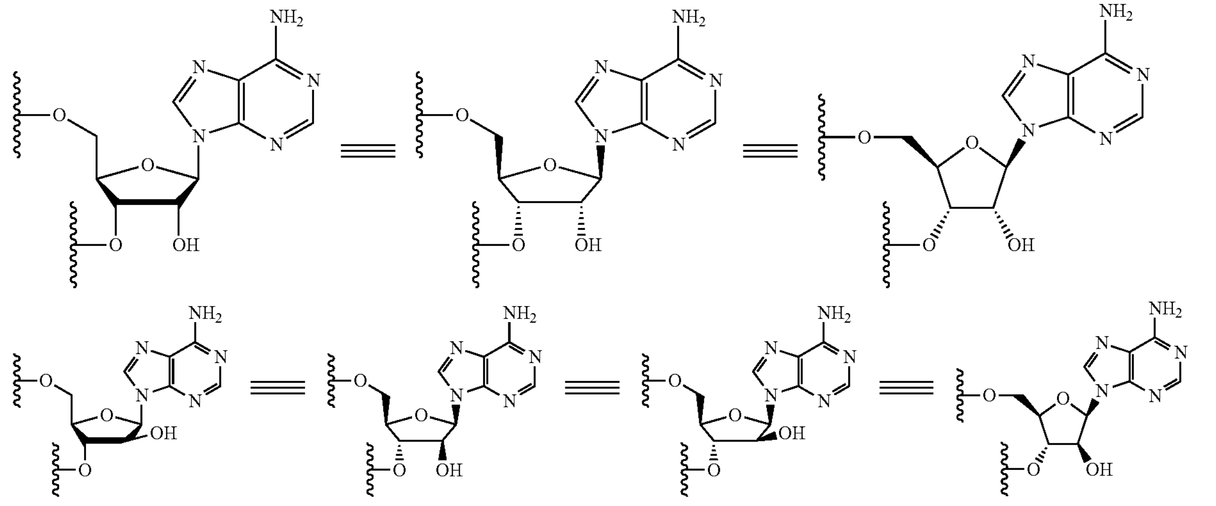

Similarly, those skilled in the art will recognize that certain compounds, and in particular compounds containing certain heteroatoms and double or triple bonds, can be tautomers, structural isomers that readily interconvert. Thus, tautomeric compounds can be drawn in a number of different ways that are equivalent. Non-limiting examples of such tautomers include those exemplified below.

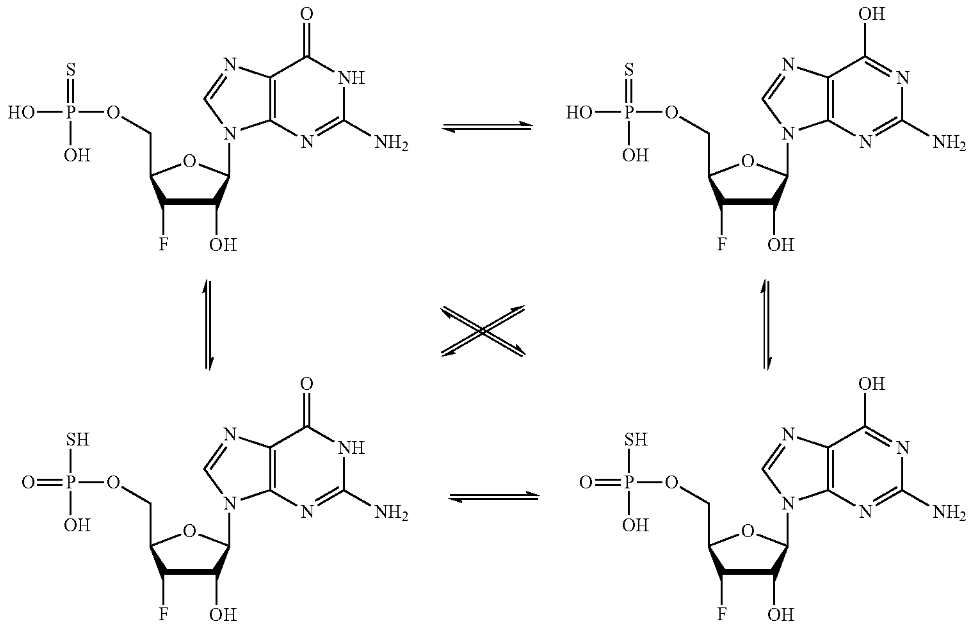

Compounds can form salts that are also within the scope of this disclosure. Reference to a compound herein is understood to include reference to salts thereof, unless otherwise indicated. The term "salt(s)," as employed herein, denotes acidic salts formed with inorganic and/or organic acids, as well as basic salts formed with inorganic and/or organic bases. In addition, when a compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds may be formed, for example, by reacting a compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids that are generally considered suitable for the formation of pharmaceutically useful salts from basic pharmaceutical compounds are discussed, for example, by P. Stahl et al., Camille G. (eds.) Handbook of Pharmaceutical Salts: Properties, Selection and Use (2002) Zurich: Wiley-VCH; S. Berge et al., J. Pharm. Sci. (1977) 66(1) 1-19; P. Gould, *International J of Pharmaceutics* (1986) 33 201-217; Anderson et al., The Practice of Medicinal Chemistry (1996), Academic Press, New York; and in THE ORANGE BOOK (Food & Drug Administration, Washington, D.C.). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine, and the like. Basic nitrogen-containing groups may be quarternized with agents such as lower alkyl halides (e.g., methyl, ethyl, and butyl chlorides, bromides, and iodides), dialkyl sulfates (e.g., dimethyl, diethyl, and dibutyl sulfates), long chain halides (e.g., decyl, lauryl, and stearyl chlorides, bromides, and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

One or more compounds herein may exist in unsolvated as well as solvated forms with pharmaceutically acceptable solvents, such as water, ethanol, and the like, and this disclosure is intended to embrace both solvated and unsolvated forms. "Solvate" means a physical association of a compound with one or more solvent molecules. This physical association involves varying degrees of ionic and covalent bonding, including hydrogen bonding. In certain instances, the solvate will be capable of isolation, for example when one or more solvent molecules are incorporated in the crystal lattice of a crystalline solid. "Solvate" encompasses both solution-phase and isolatable solvates. Non-limiting examples of suitable solvates include ethanolates, methanolates, and the like. "Hydrate" is a solvate in which the solvent molecule is $H_2O$.

"Protein," "polypeptide," and "peptide" are used interchangeably herein to denote a polymer of at least two amino acids covalently linked by an amide bond, regardless of length or post-translational modification (e.g., glycosylation or phosphorylation, lipidation, myristoylation, ubiquitination, etc.). Included within this definition are D- and L-amino acids, and mixtures of D- and L-amino acids, as well as polymers comprising D- and L-amino acids, and mixtures of D- and L-amino acids. Proteins, polypeptides, and peptides may include a tag, such as a histidine tag, which should not be included when determining percentage of sequence identity.

"Amino acid" or "residue" as used in context of the polypeptides disclosed herein refers to the specific monomer at a sequence position. Amino acids are referred to herein by either their commonly known three-letter symbols or by the one-letter symbols recommended by IUPAC-IUB Biochemical Nomenclature Commission. Nucleotides, likewise, may be referred to by their commonly accepted single letter codes.

The abbreviations used for the genetically encoded amino acids are conventional and are as follows: alanine (Ala or A), arginine (Arg or R), asparagine (Asn or N), aspartate (Asp or D), cysteine (Cys or C), glutamate (Glu or E), glutamine (Gln or Q), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

The abbreviations used for the genetically encoding nucleosides are conventional and are as follows: adenosine (A); guanosine (G); cytidine (C); thymidine (T); and uridine (U). Unless specifically delineated, the abbreviated nucleosides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated.

"Derived from" as used herein in the context of enzymes, identifies the originating enzyme, and/or the gene encoding such enzyme, upon which the enzyme was based. For example, the ketoreductase enzyme of SEQ ID NO: 7 was obtained by artificially evolving, over multiple generations the gene encoding the ketoreductase enzyme of SEQ ID NO: 1. Thus, this evolved ketoreductase enzyme is "derived from" the ketoreductase of SEQ ID NO: 1.

"Hydrophilic amino acid or residue" refers to an amino acid or residue having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include L-Thr (T), L-Ser (S), L-His (H), L-Glu (E), L-Asn (N), L-Gln (Q), *L*-Asp (D), L-Lys (K), and L-Arg (R).

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic amino acid or residue" refers to a hydrophilic amino acid or residue having a side chain exhibiting a pKa value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S), and L-Thr (T).

"Hydrophobic amino acid or residue" refers to an amino acid or residue having a side chain exhibiting a hydrophobicity of greater than zero according to the normalized consensus hydrophobicity scale of Eisenberg et al., 1984, J. Mol. Biol. 179:125-142. Genetically encoded hydrophobic amino acids include L-Pro (P), L-Ile (I), L-Phe (F), L-Val (V), L-Leu (L), L-Trp (W), L-Met (M), L-Ala (A), and L-Tyr (Y).

"Aromatic amino acid or residue" refers to a hydrophilic or hydrophobic amino acid or residue having a side chain that includes at least one aromatic or heteroaromatic ring. Genetically encoded aromatic amino acids include L-Phe (F), L-Tyr (Y), L-His (H), and L-Trp (W). L-His (H) histidine is also classified herein as a hydrophilic residue or as a constrained residue.

As used herein, "constrained amino acid or residue" refers to an amino acid or residue that has a constrained geometry. Herein, constrained residues include L-Pro (P) and L-His (H). Histidine has a constrained geometry because it has a relatively small imidazole ring. Proline has a constrained geometry because it also has a five-membered ring.

"Non-polar amino acid or residue" refers to a hydrophobic amino acid or residue that has a side chain that is uncharged at physiological pH and that has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M), and L-Ala (A).

As used herein, "aliphatic amino acid or residue" refers to a hydrophobic amino acid or residue having an aliphatic hydrocarbon side chain. Genetically encoded aliphatic amino acids include L-Ala (A), L-Val (V), L-Leu (L), and L-Ile (I).

The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure, L-Cys (C) is categorized into its own unique group. It is noted that cysteine (or "L-Cys" or "[C]") is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges.

As used herein, "small amino acid or residue" refers to an amino acid or residue having a side chain that is composed of a total three or fewer carbon and/or heteroatoms (excluding the α-carbon and hydrogens). The small amino acids or residues may be further categorized as aliphatic, non-polar, polar, or acidic small amino acids or residues, in accordance with the above definitions. Genetically-encoded small amino acids include L-Ala (A), L-Val (V), L-Cys (C), L-Asn (N), L-Ser (S), L-Thr (T), and L-Asp (D).

"Hydroxyl-containing amino acid or residue" refers to an amino acid containing a hydroxyl (—OH) moiety. Genetically-encoded hydroxyl-containing amino acids include L-Ser (S) L-Thr (T), and L-Tyr (Y).

As used herein, "polynucleotide" and "nucleic acid" refer to two or more nucleotides that are covalently linked together. The polynucleotide may be wholly comprised of ribonucleotides (i.e., RNA), wholly comprised of 2' deoxyribonucleotides (i.e., DNA), or comprised of mixtures of ribo- and 2' deoxyribonucleotides. While the nucleosides will typically be linked together via standard phosphodiester linkages, the polynucleotides may include one or more non-standard linkages. The polynucleotide may be single-stranded or double-stranded, or the polynucleotide may include both single-stranded regions and double-stranded regions. Moreover, while a polynucleotide will typically be composed of the naturally occurring encoding nucleobases (i.e., adenine, guanine, uracil, thymine, and cytosine), it may include one or more modified and/or synthetic nucleobases, such as, for example, inosine, xanthine, hypoxanthine, etc. In some embodiments, such modified or synthetic nucleobases are nucleobases encoding amino acid sequences.

As used herein, "nucleoside" refers to glycosylamines comprising a nucleobase (i.e., a nitrogenous base), and a 5-carbon sugar (e.g., ribose or deoxyribose). Non-limiting examples of nucleosides include cytidine, uridine, adenosine, guanosine, thymidine, and inosine. In contrast, the term "nucleotide" refers to the glycosylamines comprising a nucleobase, a 5-carbon sugar, and one or more phosphate groups. In some embodiments, nucleosides can be phosphorylated by kinases to produce nucleotides.

As used herein, "nucleoside diphosphate" refers to glycosylamines comprising a nucleobase (i.e., a nitrogenous base), a 5-carbon sugar (e.g., ribose or deoxyribose), and a diphosphate (i.e., pyrophosphate) moiety. In some embodiments herein, "nucleoside diphosphate" is abbreviated as "NDP." Non-limiting examples of nucleoside diphosphates include cytidine diphosphate (CDP), uridine diphosphate (UDP), adenosine diphosphate (ADP), guanosine diphosphate (GDP), thymidine diphosphate (TDP), and inosine diphosphate (IDP). The terms "nucleoside" and "nucleotide" may be used interchangeably in some contexts.

As used herein, "nucleoside triphosphate" refers to glycosylamines comprising a nucleobase (i.e., a nitrogenous base), a 5-carbon sugar (e.g., ribose or deoxyribose), and a triphosphate moiety. In some embodiments herein, "nucleoside triphosphate" is abbreviated as "NTP." Non-limiting examples of nucleoside triphosphates include cytidine triphosphate (CTP), uridine triphosphate (UTP), adenosine triphosphate (ATP), guanosine triphosphate (GTP), thymidine triphosphate (TTP), and inosine triphosphate (ITP). The terms "nucleoside" and "nucleotide" may be used interchangeably in some contexts.

As used herein, "conservative amino acid substitution" refers to a substitution of a residue with a different residue having a similar side chain, and thus typically involves substitution of the amino acid in the polypeptide with amino acids within the same or similar defined class of amino acids. By way of example and not limitation, in some embodiments, an amino acid with an aliphatic side chain is substituted with another aliphatic amino acid (e.g., alanine, valine, leucine, and isoleucine); an amino acid with an hydroxyl side chain is substituted with another amino acid with an hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basic side chain (e.g., lysine and arginine); an amino acid with an acidic side chain is substituted with another amino acid with an acidic side chain (e.g., aspartic acid and glutamic acid); and/or a hydrophobic or hydrophilic amino acid is replaced with another hydrophobic or hydrophilic amino acid, respectively.

As used herein, "non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

As used herein, "deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an evolved enzyme. Deletions can be directed to the internal portions and/or terminal portions of the polypeptide. In various embodiments, the deletion can comprise a continuous segment or can be discontinuous. Deletions are typically indicated by "-" in amino acid sequences.

As used herein, "insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

The term "amino acid substitution set" or "substitution set" refers to a group of amino acid substitutions in a polypeptide sequence, as compared to a reference sequence. A substitution set can have 1, 2, 3, 4, 5, 6, 7, 8, 9, 10, 11, 12, 13, 14, 15, or more amino acid substitutions.

A "functional fragment" and "biologically active fragment" are used interchangeably herein to refer to a polypeptide that has an amino-terminal and/or carboxy-terminal deletion(s) and/or internal deletions, but where the remaining amino acid sequence is identical to the corresponding positions in the sequence to which it is being compared and that retains substantially all of the activity of the full-length polypeptide.

As used herein, "isolated polypeptide" refers to a polypeptide that is substantially separated from other contaminants that naturally accompany it (e.g., protein, lipids, and polynucleotides). The term embraces polypeptides that have been removed or purified from their naturally occurring environment or expression system (e.g., within a host cell or via in vitro synthesis). The recombinant polypeptides may be present within a cell, present in the cellular medium, or prepared in various forms, such as lysates or isolated preparations. As such, in some embodiments, the recombinant polypeptides can be an isolated polypeptide.

As used herein, "substantially pure polypeptide" or "purified protein" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. However, in some embodiments, an enzyme comprising composition comprises enzymes that are less than 50% pure (e.g., about 10%, about 20%, about 30%, about 40%, or about 50%). Generally, a substantially pure enzyme or polypeptide composition comprises about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated recombinant polypeptides are substantially pure polypeptide compositions.

"Improved enzyme property" refers to an enzyme that exhibits an improvement in any enzyme property as compared to a reference enzyme. For the enzymes described herein, the comparison is generally made to the wild-type enzyme, although in some embodiments, the reference enzyme can be another improved enzyme. Enzyme properties for which improvement is desirable include, but are not limited to, enzymatic activity (which can be expressed in terms of percent conversion of the substrate), thermal stability, pH activity profile, cofactor requirements, refractoriness to inhibitors (e.g., product inhibition), stereospecificity, and stereoselectivity (including enantioselectivity).

"Increased enzymatic activity" refers to an improved property of the enzymes, which can be represented by an increase in specific activity (e.g., product produced/time/weight protein) or an increase in percent conversion of the substrate to the product (e.g., percent conversion of starting amount of substrate to product in a specified time period using a specified amount of enzyme) as compared to the reference enzyme. Exemplary methods to determine enzyme activity are provided in the Examples. Any property relating to enzyme activity may be affected, including the classical enzyme properties of $K_m$, $V_{max}$, or $k_{cat}$, changes of which can lead to increased enzymatic activity. Improvements in enzyme activity can be from about 1.5 times the enzymatic activity of the corresponding wild-type enzyme, to as much as 2 times. 5 times, 10 times, 20 times, 25 times, 50 times, 75 times, 100 times, 150 times, 200 times, 500 times, 1000 times, 3000 times, 5000 times, 7000 times or more enzymatic activity than the naturally occurring enzyme or another enzyme from which the polypeptides were derived. In specific embodiments, the enzyme exhibits improved enzymatic activity in the range of 150 to 3000 times, 3000 to 7000 times, or more than 7000 times greater than that of the parent enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10^9$ ($M^{-1}$ $s^{-1}$). Hence, any improvements in the enzyme activity will have an upper limit related to the diffusion rate of the substrates acted on by the enzyme. Enzyme activity can be measured by any one of standard assays used for measuring kinase activity, or via a coupled assay with an nucleoside phosphorylase enzyme which is capable of catalyzing reaction between the polypeptide product and a nucleoside base to afford a nucleoside, or by any of the traditional methods for assaying chemical reactions, including but not limited to HPLC, HPLC-MS, UPLC, UPLC-MS, TLC, and NMR. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. In some embodiments, an "expression vector" has a promoter sequence operably linked to the DNA sequence (e.g., transgene) to drive expression in a host cell, and in some embodiments, also comprises a transcription terminator sequence.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, an amino acid or nucleotide sequence (e.g., a promoter sequence, signal peptide, terminator sequence, etc.) is "heterologous" to another sequence with which it is operably linked if the two sequences are not associated in nature. For example, a "heterologous polynucleotide" is any polynucleotide that is introduced into a host cell by laboratory techniques, and the term includes polynucleotides that are removed from a host cell, subjected to laboratory manipulation, and then reintroduced into a host cell.

As used herein, the terms "host cell" and "host strain" refer to suitable hosts for expression vectors comprising DNA provided herein (e.g., the polynucleotides encoding the variants). In some embodiments, the host cells are prokaryotic or eukaryotic cells that have been transformed or transfected with vectors constructed using recombinant DNA techniques as known in the art.

The term "analogue" means a polypeptide having more than 70% sequence identity but less than 100% sequence identity (e.g., more than 75%, 78%, 80%, 83%, 85%, 88%, 90%, 91%, 92%, 93%, 94%, 95%, 96%, 97%, 98%, or 99% sequence identity) with a reference polypeptide. In some embodiments, "analogues" means polypeptides that contain one or more non-naturally occurring amino acid residues including, but not limited, to homoarginine, omithine and norvaline, as well as naturally occurring amino acids. In some embodiments, analogues also include one or more D-amino acid residues and non-peptide linkages between two or more amino acid residues.

As used herein, "EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

As used herein, "ATCC" refers to the American Type Culture Collection whose biorepository collection includes genes and strains.

As used herein, "NCBI" refers to National Center for Biological Information and the sequence databases provided therein.

"Coding sequence" refers to that portion of a nucleic acid (e.g., a gene) that encodes an amino acid sequence of a protein.

"Naturally occurring" or "wild-type" refers to a form found in nature. For example, a naturally occurring or wild-type polypeptide or polynucleotide sequence is a sequence present in an organism that can be isolated from a source in nature and that has not been intentionally modified by human manipulation, with the sole exception that wild-type polypeptide or polynucleotide sequences as identified herein may include a tag, such as a histidine tag, which should not be included when determining percentage of sequence identity. Herein, "wild-type" polypeptide or polynucleotide sequences may be denoted "WT".

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410; and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff and Henikoff, 1989, Proc. Natl. Acad. Sci. Usa 89:10915).

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison WI), using default parameters provided.

"Substantial identity" refers to a polynucleotide or polypeptide sequence that has at least 80 percent sequence identity, preferably at least 85 percent sequence identity, more preferably at least 89 percent sequence identity, more preferably at least 95 percent sequence identity, and even more preferably at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, more preferably at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (EE) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (DE). Enantiomeric excess and diastereomeric excess are types of stereomeric excess.

"Highly stereoselective" refers to a chemical or enzymatic reaction that is capable of converting a substrate to its corresponding product with at least about 85% stereoisomeric excess.

"Chemoselectivity" refers to the preferential formation in a chemical or enzymatic reaction of one product over another.

"Conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a polypeptide can be expressed as "percent conversion" of the substrate to the product.

"Chiral alcohol" refers to amines of general formula $R^1$—CH(OH)—$R^2$ wherein $R^1$ and $R^2$ are nonidentical and is employed herein in its broadest sense, including a wide variety of aliphatic and alicyclic compounds of different, and mixed, functional types, characterized by the presence of a primary hydroxyl group bound to a secondary carbon atom which, in addition to a hydrogen atom, carries either (i) a divalent group forming a chiral cyclic structure, or (ii) two substituents (other than hydrogen) differing from each other in structure or chirality. Divalent groups forming a chiral cyclic structure include, for example, 2-methylbutane-1,4-diyl, pentane-1,4-diyl, hexane-1,4-diyl, hexane-1,5-diyl, 2-methylpentane-1,5-diyl. The two different substituents on the secondary carbon atom ($R^1$ and $R^2$ above) also can vary widely and include alkyl, aralkyl, aryl, halo, hydroxy, lower alkyl, lower alkoxy, lower alkylthio, cycloalkyl, carboxy, carboalkoxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, aralkyl, or aryl substituted by the foregoing.

Immobilized enzyme preparations have a number of recognized advantages. They can confer shelf life to enzyme preparations, they can improve reaction stability, they can enable stability in organic solvents, they can aid in protein removal from reaction streams, as examples. "Stable" refers to the ability of the immobilized enzymes to retain their structural conformation and/or their activity in a solvent system that contains organic solvents. Stable immobilized enzymes lose less than 10% activity per hour in a solvent system that contains organic solvents. Stable immobilized enzymes lose less than 9% activity per hour in a solvent system that contains organic solvents. Preferably, the stable immobilized enzymes lose less than 8% activity per hour in a solvent system that contains organic solvents. Preferably, the stable immobilized enzymes lose less than 7% activity per hour in a solvent system that contains organic solvents. Preferably, the stable immobilized enzymes lose less than 6% activity per hour in a solvent system that contains organic solvents. Preferably, the stable immobilized enzymes lose less than 5% activity per hour in a solvent system that contains organic solvents. Preferably, the stable immobilized enzymes less than 4% activity per hour in a solvent system that contains organic solvents. Preferably, the stable immobilized enzymes lose less than 3% activity per hour in a solvent system that contains organic solvents. Preferably, the stable immobilized enzymes lose less than 2% activity per hour in a solvent system that contains organic solvents. Preferably, the stable immobilized enzymes lose less than 1% activity per hour in a solvent system that contains organic solvents.

"Thermostable" refers to a polypeptide that maintains similar activity (more than 60% to 80% for example) after exposure to elevated temperatures (e.g., 400 to 80° C.) for a period of time (e.g., 0.5 h to 24 h) compared to the untreated enzyme.

"Solvent stable" refers to a polypeptide that maintains similar activity (more than e.g., 60% to 80%) after exposure to varying concentrations (e.g., 5% to 99%) of solvent (isopropyl alcohol, tetrahydrofuran, 2-methyltetrahydrofuran, acetone, toluene, butylacetate, methyl tert-butylether, etc.) for a period of time (e.g., 0.5 h to 24 h) compared to the untreated enzyme.

"pH stable" refers to a polypeptide that maintains similar activity (more than e.g., 60% to 80%) after exposure to high or low pH (e.g., 4.5 to 6 or 8 to 12) for a period of time (e.g., 0.5 h to 24 h) compared to the untreated enzyme.

"Thermo- and solvent stable" refers to a polypeptide that is both thermostable and solvent stable.

As used herein, the terms "biocatalysis," "biocatalytic," "biotransformation," and "biosynthesis" refer to the use of enzymes to perform chemical reactions on organic compounds.

The term "effective amount" means an amount sufficient to produce the desired result. One of general skill in the art may determine what the effective amount by using routine experimentation.

The terms "isolated" and "purified" are used to refer to a molecule (e.g., an isolated nucleic acid, polypeptide, etc.) or other component that is removed from at least one other component with which it is naturally associated. The term "purified" does not require absolute purity, rather it is intended as a relative definition.

Exemplary methods and materials are described herein, although methods and materials similar or equivalent to those described herein can also be used in the practice or testing of the present disclosure. The materials, methods, and examples are illustrative only and not intended to be limiting.

ABBREVIATIONS 2,4,6-collidine 2,4,6-Trimethylpyridine
2,6-lutidine 2,6-Dimethylpyridine
2-Me-THF 2-Methyltetrahydrrofuran
3'-F-thio-GMP (2S,3R,4S,5R)-5-(2-amino-6-oxo-1,6-dihydro-9H-purin-9-yl)-3-fluoro-4-hydroxy-2-(mercaptomethyl)tetrahydrofuran-3-yl dihydrogen phosphate, also known as 3'-fluoro-thio-guanosine monophosphate
Ac Acetyl
ACN, MeCN Acetonitrile
AcOH, HOAc Acetic acid
Bu Butyl
CPME Cyclopentylmethyl ether
DABCO 1,3-Diazabicyclo[2.2.2]octane
DBU 1,8-Diazabicyclo[5.4.0]undec-7-ene
DI water Deionized water
DMAc Dimethylacetamide
DME, Glyme Dimethoxyethane
DMF N,N-Dimethylformamide
DMPU N,N'-Dimethylpropyleneurea
eq Equivalents
Et Ethyl, $CH_3CH_2$—
EtOAc Ethyl acetate
g Grams
h Hour
$H_2O$ Water
HFIP Hexafluoro-2-propanol
IPA Isopropyl alcohol
IPAc Isopropyl acetate
IPTG Isopropyl O-D-1-thiogalactopyranoside
kg Kilogram
L, l liter
M Molar, moles per liter
Me Methyl, $CH_3$—
mg Milligrams
MIBK Methyl isobutyl ketone
min Minute(s)
mL or ml Milliliters
mM Millimole per liter
mmol Millimoles
Ms Methanesulfonyl
MTBE Methyl tert-butyl ether, methyl tertiary butyl ether
NADPH Nicotinamide adenine dinucleotide phosphate
NFSI N-fluorobenzenesulfonimide
NMI 1-Methylimidazole
NMP N-Methyl-2-pyrrolidone
OD Optical density
PG Protecting group
Ph Phenyl
Py Pyridine
RPM, rpm Revolutions per minute
RT Room temperature, approximately 25° C.
STAB Sodium triacetoxyborohydride
TBS tert-Butyldimethylsilyl
TEA, $Et_3N$ Triethylamine
TFA Trifluoroacetic acid
TFE 2,2,2-Trifluoroethanon
THF Tetrahydrofuran
Trityl Triphenylmethyl
Ts para-Toluenesulfonyl (tosyl)
UPLC Ultra-Performance Liquid Chromatography
Vol., vol Volumes The present disclosure provides a process for preparing compounds of Formula (I) and pharmaceutically acceptable salts, hydrates, and solvates thereof:

(I)

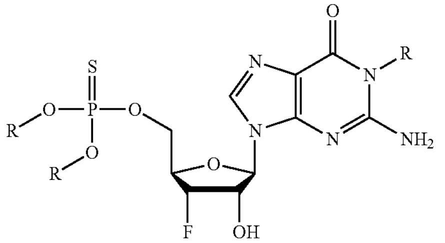

wherein each R is independently selected from the group consisting of H, Na, and K. In specific embodiments, the disclosure provides a process for preparing a compound of Formula (Ia), 3'-F-thio-GMP, and pharmaceutically acceptable salts, hydrates, and solvates thereof:

(Ia)

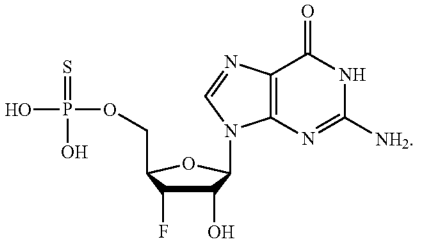

A first embodiment of this process comprises first reacting a compound of Formula (I-1) with a thiophosphorylating agent in the presence of at least one Catalyst A and at least one Base A in the presence of at least one Solvent A, to form a compound of Formula (I-1') and then reacting the compound of Formula (I-1') with at least one Base B in the presence of at least one Solvent B to form a compound of Formula (I).

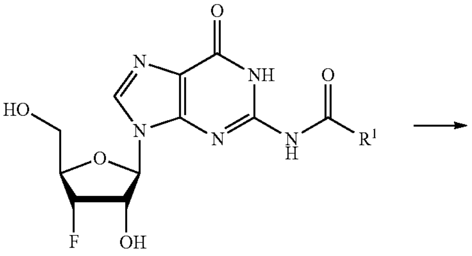

(I-1)

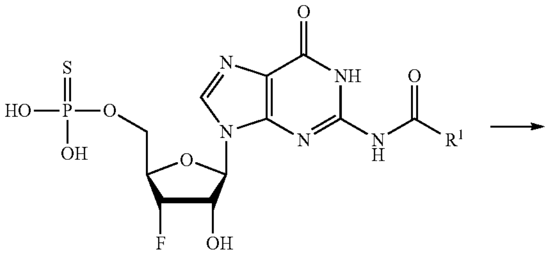

(I-1')

-continued

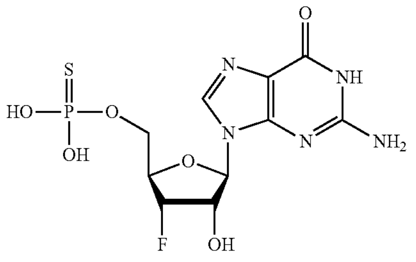

(I)

In compounds of Formula (I-1), each R is as defined above, and $R^1$ is selected from the group consisting of $C_1$-$C_{12}$ alkyl, benzyl, aryl, and heteroaryl. In particular aspects of this embodiment, $R^1$ is selected from the group consisting of $C_1$-$C_{12}$ alkyl. In still more particular aspects of this embodiment, $R^1$ is selected from the group consisting of methyl, ethyl, propyl, isopropyl, n-butyl, tert-butyl, and isobutyl. In still more particular aspects of this embodiment, $R^1$ is isobutyl.

In a first aspect of the first embodiment, the thiophosphorylating agent is $PSCl_3$. In specific instances of this aspect, the thiophosphorylating agent is provided in an amount in a range of from about 0.5 to about 5.0 equivalents with respect to the amount of the compound of Formula (I-1), such as an amount in a range of from about 0.75 to about 3.5 equivalents, an amount in a range of from about 1.0 to about 2.5 equivalents, or an amount in a range of from about 1.25 to about 1.5 equivalents.

In a second aspect of the first embodiment, the Catalyst A is selected from the group consisting of

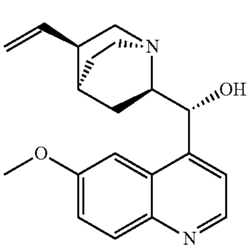

(quinine),

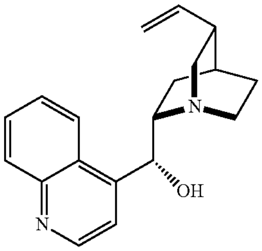

(cinchonidine),

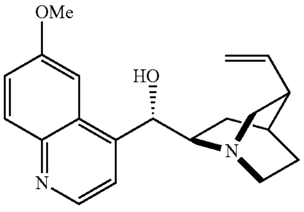

(quinidine),

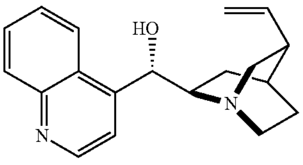

(cinchonine),

-continued

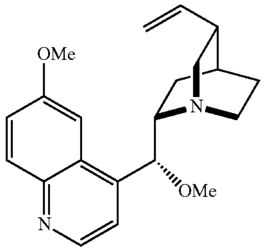

,

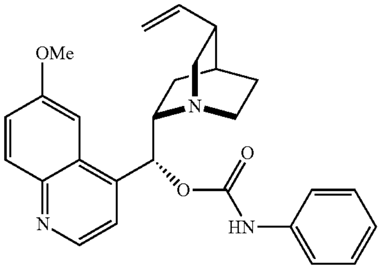

,

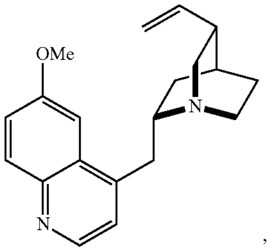

,

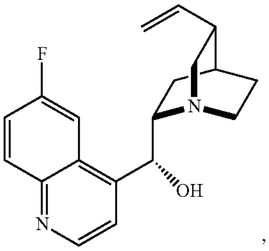

,

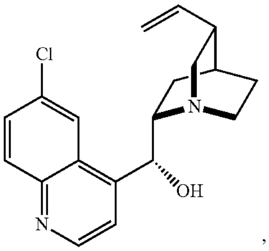

,

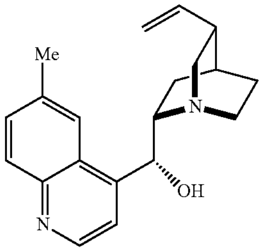

,

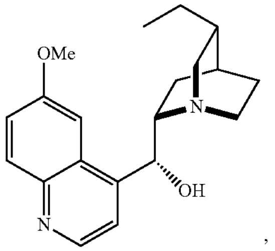

,

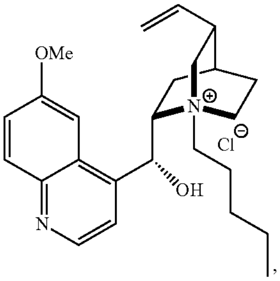

,

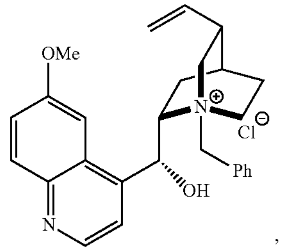

,

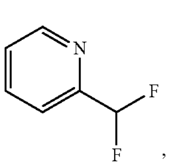

,

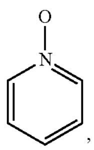

,

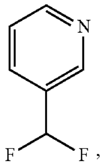

,

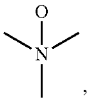

,

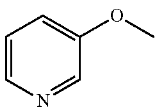

,

-continued

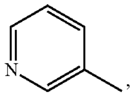, 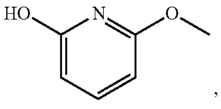, 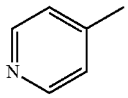,

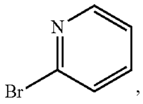, 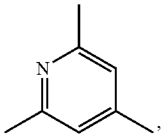, and 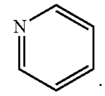.

In specific instances of this aspect, the Catalyst A is selected from

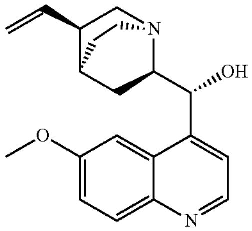, 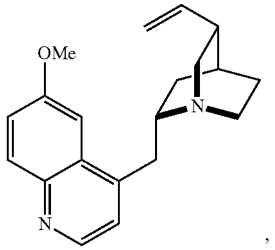,

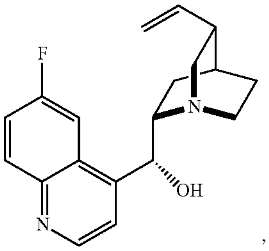, 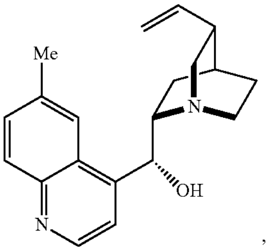,

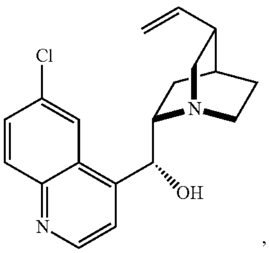, 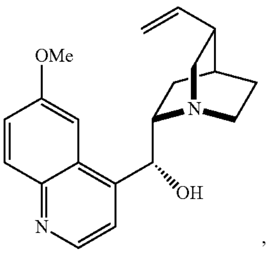,

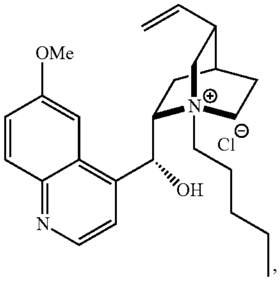, 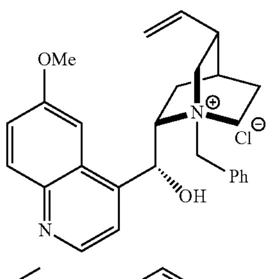,

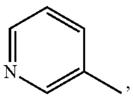, 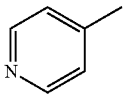, and 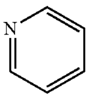.

In more specific instances, the Catalyst A is

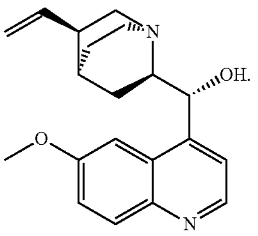 [SMILES: C=C[C@H]1C[N@]2CC[C@H]1C[C@@H]2[C@H](O)c1ccnc2ccc(OC)cc12]

In specific instances of this aspect, the Catalyst A is provided in an amount in a range of from about 0.01 to about 5.0 equivalents with respect to the amount of the compound of Formula (I-1), such as an amount in a range of from about 0.1 to about 1.0 equivalents, an amount in a range of from about 0.15 to about 0.4 equivalents, or an amount of about 0.25 equivalents.

In a third aspect of the first embodiment, the at least one Base A is selected from the group consisting of 2,6-lutidine, pyridine, $Et_3N$, 1,8-bis(dimethylamino)naphthalene (commercially available from SigmaAldrich as Proton Sponge®), 2,6-lutidine, 2,4-lutidine, 2-methyl-pyridine, trimethylpyridine, 3-methoxy-pyridine, 4-methyl-pyridine, quinuclidine, Hunig's base, 3-methyl-pyridine, and 2,6-di-tert-butyl-4-methyl pyridine, and mixtures thereof. In specific instances of this aspect, the at least one Base A is 2,6-lutidine. In specific instances of this aspect, the at least one Base A is provided in an amount in a range of from about 0.5 to about 5.0 equivalents with respect to the amount of the compound of Formula (I-1), such as an amount in a range of from about 1.0 to about 3 equivalents, or an amount of about 1.5 equivalents.

In a fourth aspect of the first embodiment, the at least one Solvent A is selected from the group consisting of THF, MeCN, acetone, DMPU, HFIP, TFE, DME, DMAc, 2-Me-THF, EtOAc, and MIBK, and mixtures thereof. In more specific instances, the at least one Solvent A is THF due to high selectivity, conversion, and yield. In specific instances of this aspect, the at least one Solvent A is provided in an amount in a range of from about 5 to about 50 volumes with respect to the amount of the compound of Formula (I-1), such as an amount in a range of from about 10 to about 30 volumes, or an amount of about 20 volumes.

In a fifth aspect of the first embodiment, the reacting to form the compound of Formula (I-1') is conducted at a temperature in a range of from about −40° C. to about 40° C., such as at a temperature in a range of from about −10° C. to about 10° C., or about −5° C.

In a sixth aspect of the first embodiment, the reaction forming the compound of Formula (I-1') is quenched using water as Quenching Reagent A.

In a seventh aspect of the first embodiment, the at least one Base B is selected from the group consisting of NaOH, KOH, $NH_4OH$, and $MeNH_2$, and mixtures thereof. In more specific instances, the at least one Base B is NaOH. In specific instances of this aspect, the at least one Base B is provided in an amount in a range of from about 1 to about 20 equivalents with respect to the amount of the compound of Formula (I-1), such as an amount in a range of from about 4 to about 14 equivalents, or an amount of about 9 equivalents.

In an eighth aspect of the first embodiment, the at least one Solvent B is selected from the group consisting of MeOH, IPA, and EtOH, and mixtures thereof. In more specific instances, the at least one Solvent B is MeOH. In more specific instances, the at least one Solvent B is MeOH. In specific instances of this aspect, the at least one Solvent B is provided in an amount in a range of from about 2 to about 20 volumes with respect to the amount of the compound of Formula (I-1), such as an amount in a range of from about 5 to about 15 volumes, or an amount of about 10 volumes.

In a ninth aspect of the first embodiment, the process further comprises isolating the compound of Formula (I) by crystallization from at least one Solvent C selected from the group of IPA, THF, EtOH, and MeCN, and mixtures thereof. In specific instances, the at least one Solvent C selected from the group of IPA and THF, and mixtures thereof. In specific instances of this ninth aspect, the at least one Solvent C is provided in an amount in a range of from about 0.5 to about 10 volumes with respect to the amount of the compound of Formula (I-1), such as an amount in a range of from about 1 to about 5 volumes, or an amount of about 2-3 volumes.

In a second embodiment, the disclosure provides a process for the preparation of the compound of Formula (I-1) by reacting a compound of Formula (I-2) with at least one Reducing Agent to provide a compound of Formula (I-1):

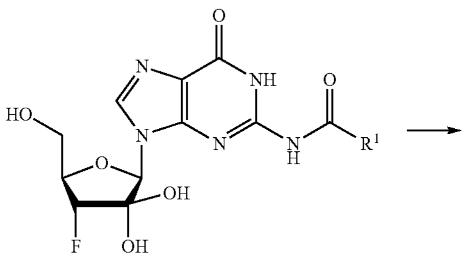

(I-2)

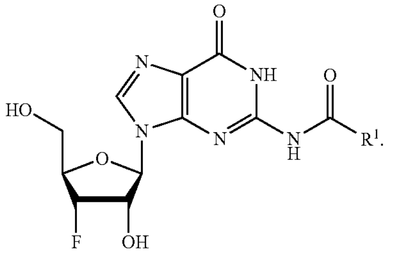

(I-1)

In a first aspect of the second embodiment, the at least one Reducing Agent is at least one chemical reducing agent selected from the group consisting of sodium triacetoxy borohydride, sodium cyanoborohydride, sodium borohydride, sodium tris(trifluoroacetoxy) borohydride, tetramethylammonium triacetoxyborohydride, sodium tri(2-methylacetoxy) borohydride, sodium tri(2-phenylacetoxy) borohydride, and mixtures thereof. In specific instances of this aspect, the at least one Reducing Agent is sodium triacetoxyborohydride. In particular instances of this first aspect of the second embodiment, the at least one Reducing Agent is provided in an amount in a range of from about 0.5 to about 5.0 equivalents with respect to the amount of the compound of Formula (I-2).

In instances of the first aspect of the second embodiment, the reacting a compound of Formula (I-2) with at least one Reducing Agent to provide a compound of Formula (I-1) is conducted in the presence of at least one Solvent D. In instances of this aspect, the at least one Solvent D is selected from the group consisting of acetonitrile, acetone, acetic acid, ethyl acetate, tetrahydrofuran, 2-methyltetrahydrofuran, N,N-dimethylformamide, and N,N-dimethylacetamide, and mixtures thereof. In particular instances of this aspect, the at least one Solvent D is selected from the group consisting of acetonitrile and acetic acid, and mixtures thereof. In more particular instances of this aspect, the at least one Solvent D is a mixture of acetonitrile and acetic acid.

In a second aspect of the second embodiment, the at least one Reducing Agent is at least one biocatalytic reducing agent selected from enzymatic reducing agents. In specific instances of this aspect, the at least one Reducing Agent is selected from one or more ketoreductase enzymes selected from the group consisting of wild-type ketoreductase enzymes and ketoreductase enzymes that are produced from the directed evolution from a commercially available, wild-type ketoreductase enzyme, and mixtures thereof. In specific instances of this aspect, the at least one Reducing Agent is selected from ketoreductase enzymes that are the product of directed evolution from a commercially available, wild-type ketoreductase, which was identified by screening a Prozomix metagenomic panel and that have the amino acid sequence as set forth below in SEQ ID NO: 1.

```
                                    (SEQ ID NO: 1)
MHHHHHHNKTIVVTGGTKGIGRAIVEKFAKEGFTV
LTCARTKGDNFPENVHFFKADLSKKVEVLAFADFI
KQTVNQVDILVNNTGFFLPGEINNEAEGTLEAMIE
TNLYSAYYLTRALVGDMITKKEGHIFNICSTASIT
AYTNGGSYCISKFALLGMSKVLREELKPHHVRVTS
ILPGATLTDSWAGVELPAERFIASEDIAQIVWTAH
CLPSTTVLEEILIRPQLGDL
```

In specific instances of this aspect, the at least one Reducing Agent is a ketoreductase enzyme comprising the amino acid sequence as set forth below in SEQ ID NO. 2.

```
                                    (SEQ ID NO: 2)
MHHHHHHNKTIVVTGGTKGIGRAIVEKFAKEGFTV
LTCARTKGDNFPENVHFFKADLSKKVEVLAFADFI
KQTVNQVDILVNNTGFFLPGEINNEAEGTLEAMIE
TNLYSAYYLTRALVGDMITKKEGHIFNICSTASIT
AYTNGGSYCISKFALLGMSKVLREELKPHHVRVTS
ILPGATLNDSWAGVELPAERFIASEDIAQIVWTAH
CLPSTTVLEEILIRPQLGDL
```

In specific instances of this aspect, the at least one Reducing Agent is a ketoreductase enzyme comprising the amino acid sequence as set forth below in SEQ ID NO. 3.

```
                                    (SEQ ID NO: 3)
MHHHHHHNKTIVVTGGTKGIGRAIVEKFAKEGFTV
LTCARTKGDNFPENVHFFKADLSKKVEVLAFADFI
KQTVNQVDILVNNTGFFLPGEINNEAEGTLEAMIE
TNLYSAYYLTRALVGDMITKKEGHIFNICSYASIT
```

-continued

AYTSGGSYCISKFALLGMSKVLREELKPHHVRVTS

ILPGATLNDSWAKVELPAERFIASEDIAQIVWTAH

CLPSTTVLEEILIRPQLGDL

In specific instances of this aspect, the at least one Reducing Agent is a ketoreductase enzyme comprising the amino acid sequence as set forth below in SEQ ID NO. 4.

(SEQ ID NO: 4)

MHHHHHPATIVVTGGTKGIGRAIVEKFAKEGFTVL

TCARTKGDNFPENVHFFKADLSKKVEVLAFADFIK

QTVNQVDILVNNTGFFLPGEINNEAEGTLEAMIET

NLYSAYYLTRALVGDMITKKEGHIFNICSYASITA

YTSGGSYCISKTALLGMSKVLREELKPHHVRVTSI

LPGATLNDSWAKVELPAEWFIASEDIAQIVWTAHC

LPSTTVLEEILIRPQLGDL

In specific instances of this aspect, the at least one Reducing Agent is a ketoreductase enzyme comprising the amino acid sequence as set forth below in SEQ ID NO. 5.

(SEQ ID NO: 5)

MHHHHHPATIVVTGGTKGIGRAIVEKFAKEGFTVL

TCARTKGDNFPENVHFFKADLSKKVEVLAFADFIK

QTVNQVDILVNNTGWFLPGEINNEAEGTLEAMIET

NLYSAYYLTRALVGDMITKKEGHIFNICSYASIVP

YTSGGSYCISKTAQLGMSKVLREELKPHHVRVTSI

LPGAVLNDSWAKVELPAEWFIASEDIAQIVWTAHC

LPSTTVLEEILIRPQLGDL

In specific instances of this aspect, the at least one Reducing Agent is a ketoreductase enzyme comprising the amino acid sequence as set forth below in SEQ ID NO. 6.

(SEQ ID NO: 6)

MHHHHHPATIVVTGGTKGIGRAIVEKFAKEGFTVL

TCARTKGDNFPENVHFFKADLSKKVEVLAFADFIK

QTVNQVDILVNNTGWFLPGEINNEAEGTLEAMIET

NLYSAYYLTRALVGDMITKKEGHIFNICSYASIVP

YTSGGSYCISKTAQLGMSKVLREELKPHHVRVTSI

LPGAVLNDSWAKVELPAELFIAPEDIAQIVWTAHC

LPSTTVLEEILIRPQTGDL

In specific instances of this aspect, the at least one Reducing Agent is a ketoreductase enzyme comprising the amino acid sequence as set forth below in SEQ ID NO. 7.

(SEQ ID NO: 7)

MHHHHHPATIVVTGGTKGIGRAIVEKFAKEGFTVL

TCARTAGDNFPENVHFFKADLSKKVEVLAFADFIK

QTVNQVDILVNNTGWFLPGEINNEEEGTLEAMIET

-continued

NLYSAYYLTRALVGDMITKKEGHIFNICSYASIVP

YTSGGSYCISKTAQLGMSKVLREELKPHHVRVTSI

LPGAVLNDSWAKVELPAELFIAPEDIAQIVWTAHC

LPSTTVLEEILIRPQEGDL

In specific instances of this aspect, the at least one Reducing Agent is a ketoreductase enzyme comprising the amino acid sequence as set forth below in SEQ ID NO. 8.

(SEQ ID NO: 8)

MHHHHHPATIVVTGGTKGIGRAIVEKFAKEGFTVL

TCARTAGDNFPENVHFFKADLSKKVEVLAFADFIK

QTVNQVDILVNNTGHFLPGEINNEEEGTLEAMIET

NLYSAYYLTRALVGDMITKKEGHIFNICSYASIVP

YTSGGSYCISKTAELGMSKVLREELKPHHVRVTSI

LPGAVLNDSWAKAELPAELFIAPEDIAQIVWTAHC

LPSTTVLEEILIRPQEGDL

In specific instances of this aspect, the at least one Reducing Agent is a ketoreductase enzyme comprising the amino acid sequence as set forth below in SEQ ID NO. 9.

(SEQ ID NO: 9)

MHHHHHPATIVVTGGTKGIGRAIVEKFAKEGFTVL

TCARTAGDNFPENVHFFKADLSKKVEVLAFADFIK

QTVNQVDILVNNTGHFLPGEINNEEEGTLEAMIET

NLYSAYYLTRALVGDMITKKEGHIFNICSYASIVP

YTSGGSYCISKTAELAMSRVLREELKPHHVRVTSI

LPGAVLNDNWAKAELPAELFIAPEDIAQIVWTAHC

LPSTTVLEEILIRPTEGDL

In specific instances of this aspect, the at least one Reducing Agent is a ketoreductase enzyme comprising the amino acid sequence as set forth below in SEQ ID NO: 10.

(SEQ ID NO: 10)

MHHHHHPATIVVTGGTKGIGRAIVEKFAKEGFTVL

TCARTAGDNFPENVHFFKADLSKKVEVLAFADFIK

ATVNQVDILVNNTGHFLPGEINNEEEGTLEAMIET

NLYSAYYLTRALVGDMITKKEGHIFNICSYASIVP

YTPGGSYCISKTAELAMSRVLREELKPHHVRVTSI

LPGAVLNDNWAKAELPAELFIAPEDIAQIVWTAHC

LPSTTVLEEILIRPTEGDL

In specific instances of this aspect, the at least one Reducing Agent is a ketoreductase enzyme comprising the amino acid sequence as set forth below in SEQ ID NO: 11.

(SEQ ID NO: 11)

MHHHHHPATIVVTGGTKGIGRAIVEKFAKEGFTVL

TCARTAGDNFPENVHFFKADLSKKVEVLAFADFIK

-continued

```
ATVNQVDILVNNTGHFLPGEINNEEEGTLEAMIET

NLYSAYYLTRALVGDMITKKEGHIFNICSYASIVP

YTSGGSYCISKTAMLAMSRVLREELKPHHVRVTSI

LPGAVLNDNWAKAELPAELFIAPEDIAQIVWTAHC

LPSTTVLEEILIRPTEGDL
```

In some instances, the at least one Reducing Agent is selected from ketoreductase enzymes that are based on the sequence Formulas of SEQ ID NO: 2, 3, 4, 5, 6, 7, 8, 9, 10, or 11 and that can comprise an amino acid sequence that is at least about 85%, 86%, 87%, 88%, 89%, 90%, 91%, 92%, 93%, 94%, 95%, 96%, 97%, 98%, or 99% identical to the reference sequence of SEQ ID NO: 2, 3, 4, 5, 6, 7, 8, 9, 10, or 11. These differences can be amino acid insertions, deletions, substitutions, or any combinations of such changes. In some embodiments, the ammo acid sequence differences can comprise non-conservative, conservative, as well as a combination of non-conservative and conservative amino acid substitutions.

In particular instances of this second aspect of the second embodiment, the at least one Reducing Agent is provided in an amount in a range of from about 0.0005 to about 1.0 equivalents with respect to the amount of the compound of Formula (I-2).

In instances of the second aspect of the second embodiment, the reacting a compound of Formula (I-2) with at least one Reducing Agent to provide a compound of Formula (I-1) is conducted in the presence of NADPH, an aqueous solution of sodium phosphate or potassium phosphate with pH between 6.0 and 7.4, and at least one Solvent E. In specific instances, the at least one Solvent E is selected from the group consisting of dimethyl sulfoxide, isopropanol, tetrahydrofuran, and mixtures thereof. In more particular instances, the mixture of 80% of 50 mM sodium phosphate at pH=6 and 20% isopropanol.

In particular instances of the second aspect of the second embodiment, the at least one Reducing Agent is selected from one or more ketoreductase enzymes that have been pre-treated with isopropanol to a volume % of at least about 20% isopropanol, and then centrifuged to remove protein components that precipitate under such conditions. In specific instances the at least one Reducing Agent is selected from one or more ketoreductase enzymes that have been pre-treated with isopropanol to a volume % of at least about 25% isopropanol and centrifuged to remove protein components that precipitate under such conditions. Specific instances of the process of the second embodiment further comprise pre-treating the at least one Reducing Agent selected from one or more ketoreductase enzymes with isopropanol to a volume % of at least about 20% isopropanol; still further specific instances of such processes further comprise removing precipitated proteins from pretreated ketoreductase enzyme Reducing Agents by centrifuge. Specific instances of the process of the second embodiment further comprise pre-treating the at least one Reducing Agent selected from one or more ketoreductase enzymes with isopropanol to a volume % of at least about 25% isopropanol; still further specific instances of such processes further comprise removing precipitated proteins from pre-treated ketoreductase enzyme Reducing Agents by centrifuge.

In further instances of the second aspect of the second embodiment, the reacting a compound of Formula (I-2) with at least one Reducing Agent to provide a compound of Formula (I-1) is conducted in the presence of a second biocatalytic additive. The second biocatalytic additive is selected from ketoreductase enzymes and glucose dehydrogenase enzymes. In specific instances, the second biocatalytic additive is selected from commercially available enzymes. In some instances, the second biocatalytic additive is a wild-type enzyme; in other instances, the second biocatalytic additive is an evolved enzyme. In particular instances, the second biocatalytic additive is a commercially available ketoreductase enzyme, which is provided as between 0.1 wt % to 25 wt % in combination with isopropanol; in specific instances, the second biocatalytic additive is selected from the group of commercially available ketoreductase enzymes comprising those available from CODEXIS as catalog reference numbers KRED-P1 B2, KRED-P1 B10, KRED-P1 H9, and KRED-P2 D11. As described above, these ketoreductases may be pre-treated with 25% isopropanol and centrifuged to remove protein components. In other particular instances, the second biocatalytic additive is a commercially available glucose dehydrogenase enzyme, which is provided in combination with glucose; in specific instances, the second biocatalytic additive is selected from the group of commercially available glucose dehydrogenase enzymes comprising those available from CODEXIS as catalog reference numbers GDH-105 and CDX-901.

In a third aspect of the second embodiment, the process further comprises crystallizing the compound of Formula (I-1) from a solution comprising (a) at least one Solvent F selected from the group consisting of acetonitrile, acetone, acetic acid, tetrahydrofuran, N,N-dimethylformamide, N,N-dimethylacetamide, isopropanol, water, and mixtures thereof, and (b) at least one salting-out agent selected from the group consisting of sodium chloride, sodium carbonate, ammonium acetate, ammonium sulfate, sodium malonate, ammonium citrate, and potassium citrate, and mixtures thereof. In instances of this fourth aspect, the salting-out agent is ammonium sulfate.

In a third embodiment, the disclosure provides a process for the preparation of the compound of Formula (I-2) by reacting a compound of Formula (I-3) with at least one Fluorinating Agent A in the presence of at least one Catalyst B, at least one Base C, and water to provide a compound of Formula (I-2):

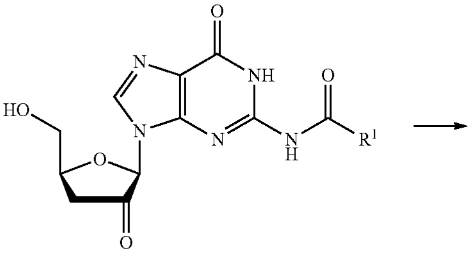

(I-3)

-continued

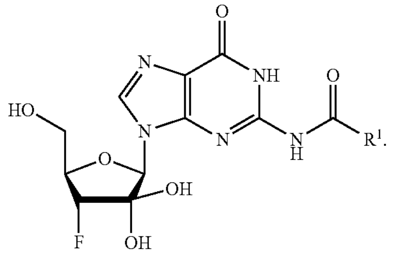

(I-2)

In aspects of the third embodiment, the at least one Fluorinating Agent A is selected from the group consisting of N-fluorobenzenesulfonimide, 1-chloromethyl-4-fluoro-1, 4-diazoniabicyclo[2.2.2]octane bis(tetrafluoroborate) (also known as F-TEDA; commercially available from SigmaAldrich as SELECTFLUOR™), 1-fluoro-4-methyl-1,4-diazoniabicyclo[2.2.2]octanebis(tetrafluoroborate) (also known as N-fluoro-N'-methyl-triethylenediamine bis(tetrafluoroborate); commercially available from SigmaAldrich as SELECTFLUOR II™), N-fluoropyridinium triflate, and N-fluoropyridinium tetrafluoroborate, and mixtures thereof. In specific instances, the at least one Fluorinating Agent A is N-fluorobenzenesulfonimide.

In further aspects of the third embodiment, the at least one Catalyst B is selected from the group consisting of ($C_1$-$C_8$ alkyl)$NH_2$,

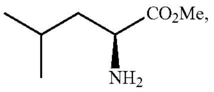 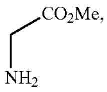 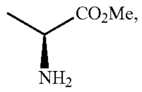

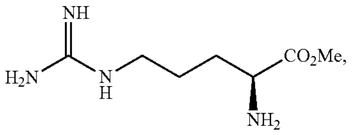

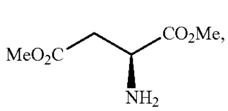 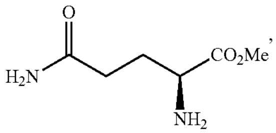

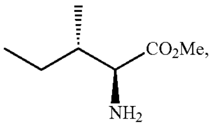 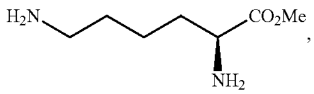

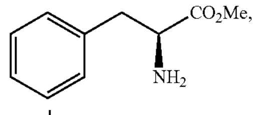 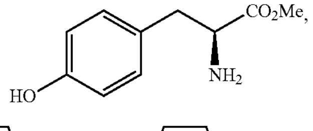

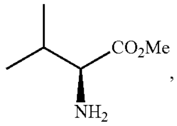 , 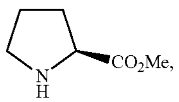 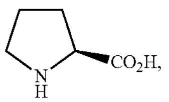

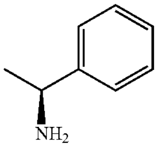 , 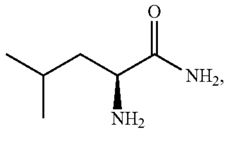

-continued

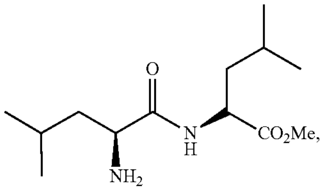 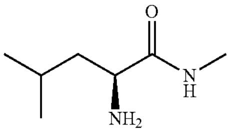 ,

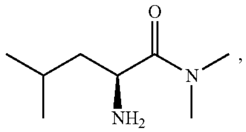 and 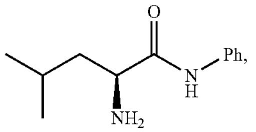

and mixtures thereof. In specific instances of these aspects, the at least one Catalyst B is

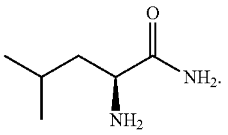

In still further aspects of the third embodiment, the at least one Base C is selected from the group consisting of lithium carbonate, sodium carbonate, sodium bicarbonate, potassium carbonate, ammonium carbonate, cesium carbonate, lithium dihydrogen phosphate, sodium hydrogen phosphate, sodium dihydrogen phosphate, sodium phosphate, potassium hydrogen phosphate, potassium dihydrogen phosphate, potassium phosphate, ammonium hydrogen phosphate, sodium acetate, ammonium acetate, sodium benzoate, sodium hydrogen sulfate, potassium hydrogen sulfate, potassium fluoride, cesium fluoride, sodium formate, and ammonium formate, and mixtures thereof. In instances of these aspects, the at least one Base C is selected from lithium dihydrogen phosphate, sodium hydrogen phosphate, sodium dihydrogen phosphate, sodium phosphate, potassium hydrogen phosphate, potassium dihydrogen phosphate, potassium phosphate, and ammonium hydrogen phosphate, and mixtures thereof. In instances of these aspects, the at least one Base C is ammonium hydrogen phosphate.

In even further aspects of the third embodiment, water is presence in a range of from about 2.0 to about 20.0 equivalents with respect to the amount of the compound of Formula (I-2), such as in a range of from about 7.5 to about 15.0 equivalents, or about 10 equivalents.

In a fourth embodiment, the disclosure provides a process for the preparation of the compound of Formula (I-3) from a compound of Formula (I-4). In particular, the process comprises preparing a compound of Formula (I-4[1]) from a compound of Formula (I-4) followed by preparing a compound of Formula (I-3) from a compound for Formula (I-4[1]):

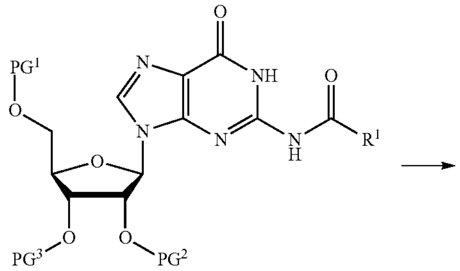

(I-4)

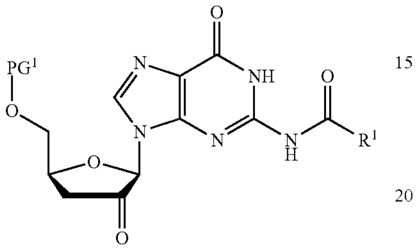

($I-4^1$)

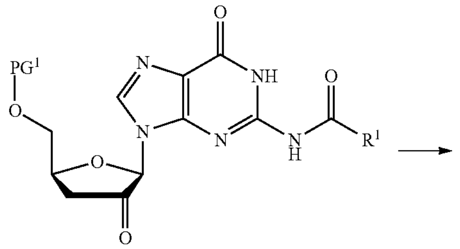

($I-4^1$)

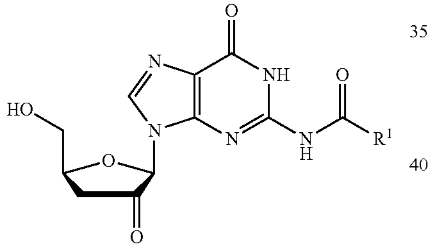

(I-3)

wherein protecting group $PG^1$ is selected from the group consisting of isobutyryl, pivaloyl, trityl, tert-butyldiphenylsilyl, and tert-butyldimethylsilyl; protecting group $PG^2$ is selected from the group consisting of isobutyroyl, pivaloyl, methanesulfonyl, ethanesulfonyl, benzenesulfonyl, 2-nitrobenzenesulfonyl, 4-nitrobenzensulfonyl, 4-chlorobenzenesulfonyl, 4-fluorobenzenesulfonyl, and p-toluenesulfonyl; and protecting group $PG^3$ is selected from the group consisting of methanesulfonyl, ethanesulfonyl, benzenesulfonyl, 2-nitrobenzenesulfonyl, 4-nitrobenzene sulfonyl, 4-chlorobenzenesulfonyl, 4-fluorobenzenesulfonyl, and p-toluenesulfonyl.

In a first aspect of the fourth embodiment, the preparing a compound of Formula ($I-4^1$) from a compound of Formula (I-4) comprises reacting the compound of Formula (I-4) with at least one Base D to form a compound of Formula ($I-4^1$).

In a first instance of this first aspect of the fourth embodiment, the at least one Base D is selected from the group consisting of lithium hydroxide, lithium methoxide, lithium ethoxide, lithium isopropoxide, lithium tert-butoxide, sodium hydroxide, sodium methoxide, sodium ethoxide, sodium isopropoxide, sodium tert-butoxide, and mixtures thereof. In specific instances, the at least one Base D is lithium isopropoxide, which can be used as a commercially available solution or prepared in situ from n-butyllithium and isopropanol. In specific instances, the at least one Base D is provided in an amount in a range of from about 4.0 to about 7.0 equivalents with respect to the amount of the compound of Formula (I-4), or an amount of about 6.0 equivalents.

In a second instance of this first aspect of the fourth embodiment, the reacting the compound of Formula (I-4) with at least one Base D is performed in the presence of at least one Solvent G. The at least one Solvent G is selected from the group consisting of THF, 2-Me-THF, DME, CPME, MTBE, DMF, toluene, acetonitrile, and mixtures thereof. In more specific instances, the at least one Solvent G is tetrahydrofuran or CPME and mixtures thereof. In specific instances of this aspect, the at least one Solvent G is provided in an amount in a range of from about 1 to about 25 volumes with respect to the amount of the compound of Formula (I-4), or an amount of about 5.5 volumes.

In a third instance of this first aspect of the fourth embodiment, the reacting the compound of Formula (I-4) with at least one Base D is performed at a temperature in a range of from about −20° C. to about 50° C., such as at a temperature in a range of from about −10° C. to about 10° C., or about 0° C.

In a fourth instance of this first aspect of the fourth embodiment, the reaction forming the compound of Formula ($I-4^1$) is quenched using a Quenching Reagent B selected from the group consisting of acetic acid, TFA, HCl, and $H_2SO_4$, and mixtures thereof. In specific occurrences of this instance, the Quenching Reagent B is acetic acid.

In a second aspect of this embodiment, the preparing a compound of Formula (I-3) from a compound of Formula ($I-4^1$) comprises reacting the compound of Formula ($I-4^1$) with at least one Acid A to form a compound of Formula (I-3). In instances of this second aspect of the fourth embodiment, the at least one Acid A is selected from the group consisting of TFA, HCl, $H_2SO_4$, MsOH, TsOH, and mixtures thereof. In more specific instances, the Acid A is TFA. In specific instances of this aspect, the Acid A is provided in an amount in a range of from about 0.5 to about 8.0 equivalents with respect to the amount of the compound of Formula (I-4), or an amount of about 5.0 equivalents.

In further instances of this second aspect of the fourth embodiment, the preparing a compound of Formula (I-3) from a compound of Formula ($I-4^1$) optionally comprises reacting the compound of Formula ($I-4^1$) with at least one Tri-Alkyl Amine A, selected from the group consisting of $N(C_1\text{-}C_{10}\text{ alkyl})_3$ and mixtures thereof. In more specific instances, the Tri-Alkyl Amine A is tri-n-octylamine. In specific instances of this aspect, the Tri-Alkyl Amine A is provided in an amount in a range of from about 0 to about 5.0 equivalents with respect to the amount of the compound of Formula (I-4), or an amount of about 2.0 equivalents.

In a third aspect of the fourth embodiment, the process further comprises crystallizing the compound of Formula (I-3) by neutralization with Tri-Alkyl Amine B, selected from the group consisting of $N(C_1\text{-}C_{10}\text{ alkyl})_3$ and mixtures thereof. In more specific instances, the Tri-Alkyl Amine B is tri-n-octylamine. In specific instances of this aspect, the Tri-Alkyl Amine B is provided in an amount in a range of from about 0.5 to about 8.0 equivalents with respect to the amount of the compound of Formula (I-4), or an amount of about 3.0 equivalents.

In a fifth embodiment, the disclosure provides an alternative process for the preparation of the compound of Formula (I-2). In particular, the process comprises preparing a compound of Formula (I-4$^1$) from a compound of Formula (I-4), followed by preparing a compound of Formula (I-2) from a compound for Formula (I-4$^1$):

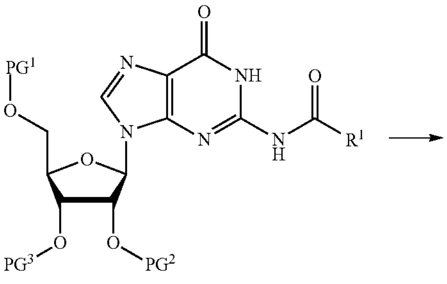

(I-4)

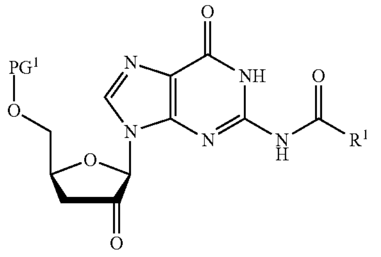

(I-4$^1$)

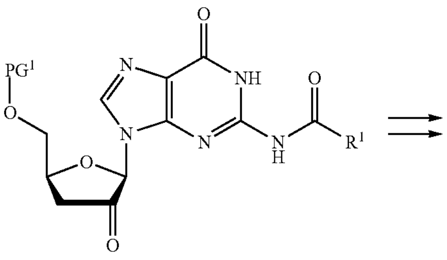

(I-4$^1$)

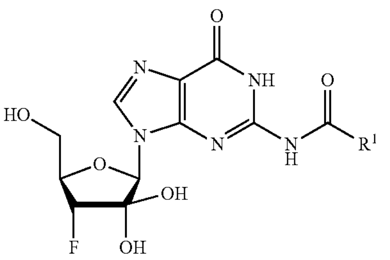

(I-2)

In a first aspect of the fifth embodiment, the process comprises reacting the compound of Formula (I-4) with at least one Base E to form a compound of Formula (I-4$^1$):

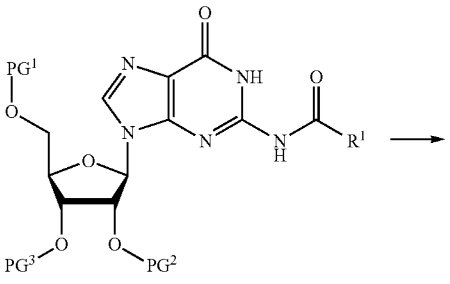

(I-4)

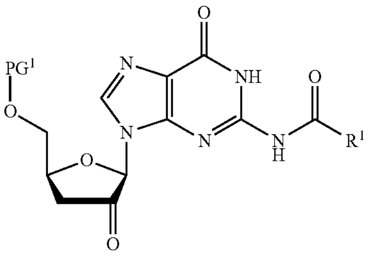

(I-4$^1$)

In a first instance of this first aspect of the fifth embodiment, the at least one Base E is selected from the group consisting of lithium hydroxide, lithium methoxide, lithium ethoxide, lithium isopropoxide, lithium tert-butoxide, sodium hydroxide, sodium methoxide, sodium ethoxide, sodium isopropoxide, sodium tert-butoxide, and mixtures thereof. In specific instances, the at least one Base E is lithium isopropoxide, which can be used as a commercially available solution or prepared in situ from n-butyllithium and isopropanol. In specific instances, the at least one Base E is provided in an amount in a range of from about 4.0 to about 7.0 equivalents with respect to the amount of the compound of Formula (I-4), or an amount of about 6.0 equivalents.

In a second instance of this first aspect of the fifth embodiment, the reacting the compound of Formula (I-4) with at least one Base E is performed in the presence of at least one Solvent H. The at least one Solvent H is selected from the group consisting of THF, 2-Me-THF, DME, CPME, MTBE, DMF, toluene, acetonitrile, and mixtures thereof. In more specific instances, the at least one Solvent H is tetrahydrofuran or CPME and mixtures thereof. In specific instances of this aspect, the at least one Solvent H is provided in an amount in a range of from about 1 to about 25 volumes with respect to the amount of the compound of Formula (I-4), or an amount of about 5.5 volumes.

In a third instance of this first aspect of the fifth embodiment, the reacting the compound of Formula (I-4) with at least one Base E is performed at a temperature in a range of from about −20° C. to about 50° C., such as at a temperature in a range of from about −10° C. to about 10° C., or about 0° C.

In a fourth instance of this first aspect of the fifth embodiment, the reaction forming the compound of Formula (I-4$^1$) is quenched using a Quenching Reagent C selected from the group consisting of acetic acid, TFA, HCl, and $H_2SO_4$, and mixtures thereof. In specific occurrences of this instance, the Quenching Reagent C is acetic acid.

In a second aspect of the fifth embodiment, the process comprises preparing the compound of Formula (I-2) by reacting a compound of Formula (I-4$^1$) with at least one Fluorinating Agent B in the presence of at least one Catalyst C, at least one Base F, and water to form a product, followed by reacting the product with at least one Acid B to form a compound of Formula (I-2):

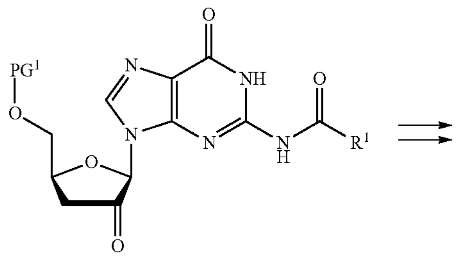

(I-4[1])

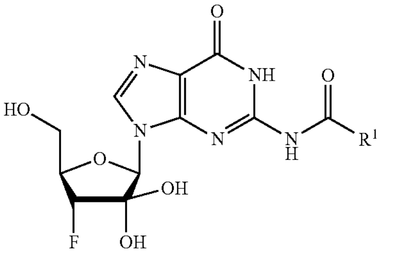

(I-2)

In a first instance of this second aspect of the fifth embodiment, the at least one Fluorinating Agent B is selected from the group consisting of N-fluorobenzenesulfonimide, 1-chloromethyl-4-fluoro-1,4-diazoniabicyclo[2.2.2] octane bis(tetrafluoroborate), 1-fluoro-4-methyl-1,4-diazoniabicyclo[2.2.2] octanebis(tetrafluoroborate), N-fluoropyridinium triflate, and N-fluoropyridinium tetrafluoroborate, and mixtures thereof. In specific instances, the at least one Fluorinating Agent B is N-fluorobenzenesulfonimide.

In a second instance of this second aspect of the fifth embodiment, the at least one Catalyst C is selected from the group consisting of ($C_1$-$C_8$ alkyl)$NH_2$,

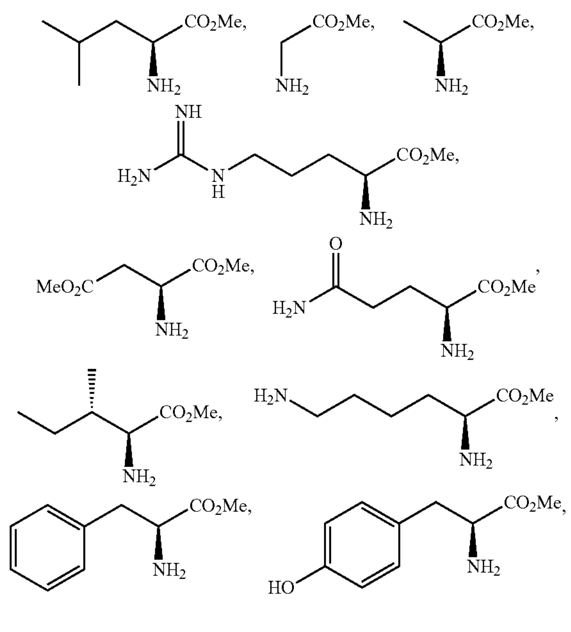

-continued

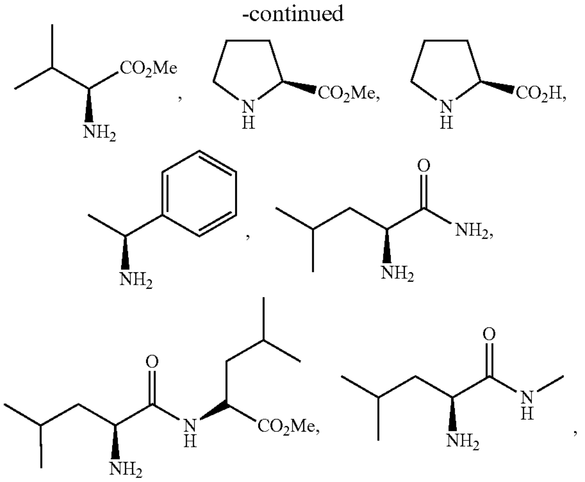

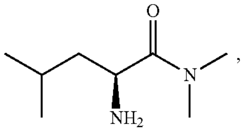

and

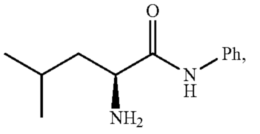

and mixtures thereof. In specific instances of these aspects, the at least one Catalyst C is

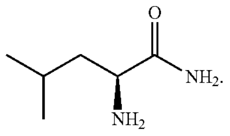

In a third instance of this second aspect of the fifth embodiment, the at least one Base F is selected from the group consisting of lithium carbonate, sodium carbonate, sodium bicarbonate, potassium carbonate, ammonium carbonate, cesium carbonate, lithium dihydrogen phosphate, sodium hydrogen phosphate, sodium dihydrogen phosphate, sodium phosphate, potassium hydrogen phosphate, potassium dihydrogen phosphate, potassium phosphate, ammonium hydrogen phosphate, sodium acetate, ammonium acetate, sodium benzoate, sodium hydrogen sulfate, potassium hydrogen sulfate, potassium fluoride, cesium fluoride, sodium formate, and ammonium formate, and mixtures thereof. In instances of these aspects, the at least one Base F is selected from lithium dihydrogen phosphate, sodium hydrogen phosphate, sodium dihydrogen phosphate, sodium phosphate, potassium hydrogen phosphate, potassium dihydrogen phosphate, potassium phosphate, and ammonium hydrogen phosphate, and mixtures thereof. In instances of these aspects, the at least one Base F is ammonium hydrogen phosphate.

In a fourth instance of this second aspect of the third embodiment, water is presence in a range of from about 2.0 to about 20.0 equivalents with respect to the amount of the compound of Formula (I-2), such as in a range of from about 7.5 to about 15.0 equivalents, or about 10 equivalents.

In a fifth instance of this second aspect of the fifth embodiment, the at least one Acid B is selected from the group consisting of TFA, HCl, $H_2SO_4$, MsOH, TsOH, and mixtures thereof. In more specific instances, the at least one Acid B is TFA. In specific instances of this aspect, the at least one Acid B is provided in an amount in a range of from about 0.5 to about 8.0 equivalents with respect to the amount of the compound of Formula (I-$4^1$), or an amount of about 5.0 equivalents.

A sixth instance of this second aspect of the fifth embodiment further comprises optionally further reacting with at least one Tri-Alkyl Amine B, selected from the group consisting of $N(C_1$-$C_{10}$ alkyl$)_3$ and mixtures thereof. In more specific instances, the Tri-Alkyl Amine B is tri-n-octylamine. In specific instances of this aspect, the Tri-Alkyl Amine B is provided in an amount in a range of from about 0 to about 5.0 equivalents with respect to the amount of the compound of Formula (I-$4^1$), or an amount of about 2.0 equivalents.

In a sixth embodiment, the disclosure provides a process for the preparation of the compound of Formula (I-4) by selectively functionalizing guanosine to provide a compound of Formula (I-4):

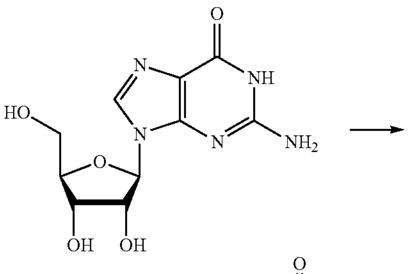

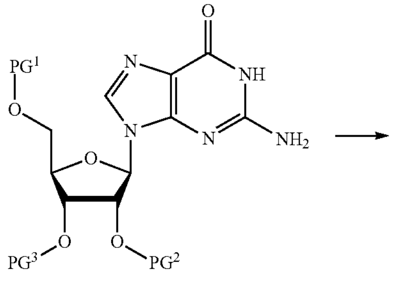

(I-$4^3$)

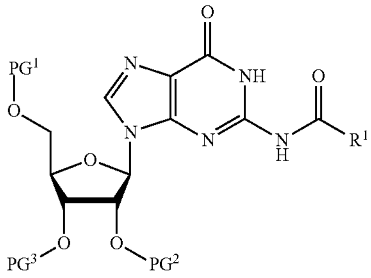

(I-4)

wherein protecting group $PG^1$ is selected from the group consisting of isobutyryl, pivaloyl, trityl, tert-butyldiphenylsilyl, and tert-butyldimethylsilyl; protecting group $PG^2$ is selected from the group consisting of isobutyryl, pivaloyl, methanesulfonyl, ethanesulfonyl, benzenesulfonyl, 2-nitrobenzenesulfonyl, 4-nitrobenzensulfonyl, 4-chlorobenzenesulfonyl, 4-fluorobenzenesulfonyl, and p-toluenesulfonyl; and protecting group $PG^3$ is selected from the group consisting of methanesulfonyl, ethanesulfonyl, benzenesulfonyl, 2-nitrobenzenesulfonyl, 4-nitrobenzene sulfonyl, 4-chlorobenzenesulfonyl, 4-fluorobenzenesulfonyl, and p-toluenesulfonyl. In this sixth embodiment, the selectively functionalizing guanosine to provide a compound of Formula (I-4) comprises:

(a) reacting guanosine with $PG^1$-Cl in the presence of at least one Base G to form the product of step (a);

(b) reacting the product of step (a) with $PG^2$-Cl and $PG^3$-Cl in the presence of at least one Base H to form the product of step (b); and (c) reacting the product of step (b) with $R^1$—COCl in the presence of at least one Base I to form the compound of Formula (I-4).

In a first aspect of this sixth embodiment, $PG^1$-Cl is selected from the group consisting of isobutyryl chloride, pivaloyl chloride, trityl, tert-butyldiphenylsilyl, and tert-butyldimethylsilyl chloride. In specific instances, $PG^1$-Cl is tert-butyldimethylsilyl chloride. In specific instances of this aspect, $PG^1$-Cl is provided in an amount in a range of from about 1.0 to about 2.0 equivalents with respect to the amount of the compound guanosine, or an amount of about 1.4 equivalents.

In a second aspect of the sixth embodiment, the at least one Base G is selected from the group consisting of pyridine, NMI, 2,6-lutidine, 2,4,6-collidine, DBU, DABCO, tetramethylguanidine, triethylamine, diisopropylethylamine, and mixtures thereof. In more specific instances, the at least one Base G is a mixture of pyridine and NMI. In specific instances of this aspect, the at least one Base G is provided in an amount in a range of from about 1.0 to about 5.0 equivalents with respect to the amount of the compound guanosine, or an amount of about 3.0 equivalents.

In a third aspect of the sixth embodiment, step a) is performed in the presence of at least one Solvent I, which is selected from the group consisting of NMP, DMF, DMAc, DMSO, pyridine, THF, 2-methyltetrahydrofuran, dimethyl carbonate, and mixtures thereof. In specific instances, the at least one Solvent I is NMP. In specific instances of this aspect, the at least one Solvent I is provided in an amount in a range of from about 2.0 to about 7.0 volumes with respect to the amount of the compound guanosine, or an amount of about 5.5 volumes.

In a fourth aspect of the sixth embodiment, step a) is conducted at a temperature in a range of from about −20° C. to about 20° C., such as at a temperature in a range of from about 0° C. to about 20° C., or about 10° C.

In a fifth aspect of the sixth embodiment, $PG^2$-Cl is selected from the group consisting of isobutyryl, pivaloyl, methanesulfonyl, ethanesulfonyl, benzenesulfonyl, 2-nitrobenzenesulfonyl, 4-nitrobenzensulfonyl, 4-chlorobenzenesulfonyl, 4-fluorobenzenesulfonyl, and p-toluenesulfonyl, and $PG^3$-Cl is selected from the group consisting of methanesulfonyl, ethanesulfonyl, benzenesulfonyl, 2-nitrobenzenesulfonyl, 4-nitrobenzensulfonyl, 4-chlorobenzenesulfonyl, 4-fluorobenzenesulfonyl, and p-toluenesulfonyl. In specific instances, $PG^2$-Cl is p-toluenesulfonyl chloride, and $PG^3$-Cl is p-toluenesulfonyl chloride. In more specific instances of this aspect, $PG^2$-Cl and $PG^3$-Cl are provided in a combined amount in a range of from about 2.0 to about 3.0 equivalents with respect to the amount of the compound guanosine, or an amount of about 2.1 equivalents.

In a sixth aspect of the sixth embodiment, the at least one Base H is selected from the group consisting of pyridine, NMI, 2,6-lutidine, 2,4,6-collidine, DBU, DABCO, tetramethylguanidine, triethylamine, diisopropylethylamine, and mixtures thereof. In more specific instances, the at least one Base H is NMI. In specific instances of this aspect, the at least one Base H is provided in an amount in a range of from about 1.0 to about 5.0 equivalents with respect to the amount of the compound guanosine, or an amount of about 3.0 equivalents.

In a seventh aspect of the sixth embodiment, $R^1$ is selected from the group consisting of $C_1$-$C_{12}$ alkyl, benzyl, aryl, and heteroaryl. In specific instances, $R^1$ is isopropyl. In specific instances of this aspect, the $R^1$—COCl is provided in an amount in a range of from about 1.0 to about 4.0 equivalents with respect to the amount of the compound of Formula (I-43), such as an amount of about 2.4 equivalents.

In an eighth aspect of the sixth embodiment, the at least one Base I is selected form the group consisting of pyridine, NMI, 2,6-lutidine, 2,4,6-collidine, DBU, DABCO, tetramethylguanidine, triethylamine, diisopropylethylamine, and mixtures thereof. In specific instances of this seventh aspect, the at least one Base I is pyridine. In specific instances of this aspect, the at least one Base I is provided in an amount in a range of from about 2.0 to about 6.0 equivalents with respect to the amount of the compound of Formula (I-43), an amount of about 4.2 equivalents.

In a seventh embodiment, the disclosure provides a process for the preparation of compounds of Formula (I), or a pharmaceutically acceptable salt, hydrate, or solvate thereof:

(I)

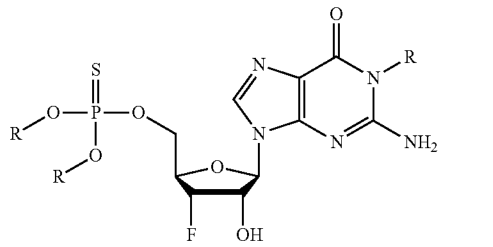

wherein each R is independently selected from the group consisting of H, Na, and K, comprising (i) selectively functionalizing guanosine to provide a compound of Formula (I-4)

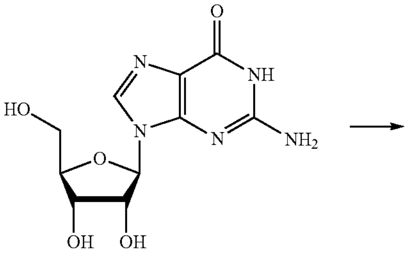

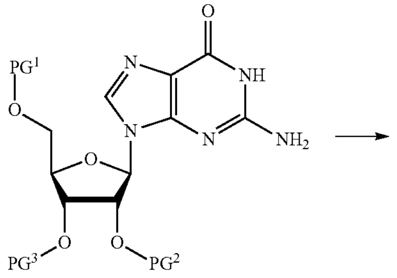

(I-4³)

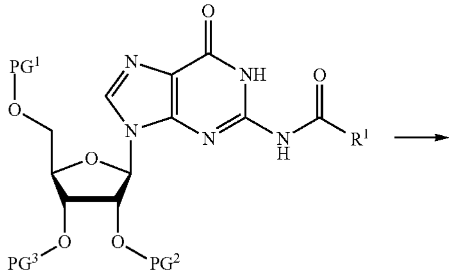

(I-4)

-continued

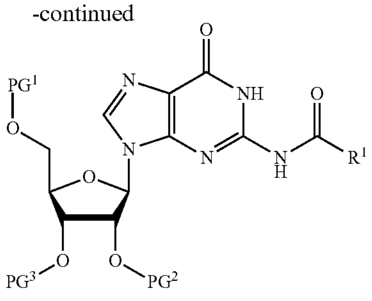

(I-4)

wherein protecting group $PG^1$ is selected from the group consisting of isobutyryl, pivaloyl, trityl, tert-butyldiphenylsilyl, and tert-butyldimethylsilyl; protecting group $PG^2$ is selected from the group consisting of isobutyryl, pivaloyl, methanesulfonyl, ethanesulfonyl, benzenesulfonyl, 2-nitrobenzenesulfonyl, 4-nitrobenzensulfonyl, 4-chlorobenzenesulfonyl, 4-fluorobenzenesulfonyl, and p-toluenesulfonyl; and protecting group $PG^3$ is selected from the group consisting of methanesulfonyl, ethanesulfonyl, benzenesulfonyl, 2-nitrobenzenesulfonyl, 4-nitrobenzene sulfonyl, 4-chlorobenzenesulfonyl, 4-fluorobenzenesulfonyl, and p-toluenesulfonyl;

wherein the selectively functionalizing guanosine to provide a compound of Formula (I-4) comprises:

(a) reacting guanosine with $PG^1$-Cl in the presence of at least one Base G, wherein the at least one Base G is selected from the group consisting of pyridine, NMI, 2,6-lutidine, 2,4,6-collidine, DBU, DABCO, tetramethylguanidine, triethylamine, diisopropylethylamine, and mixtures thereof, to form a product of step (a);

(b) reacting the product of step (a) with $PG^2$-Cl and $PG^3$-Cl in the presence of at least one Base H, wherein the at least one Base H is selected from the group consisting of pyridine, NMI, 2,6-lutidine, 2,4,6-collidine, DBU, DABCO, tetramethylguanidine, triethylamine, diisopropylethylamine, and mixtures thereof, to form a product of step (b); and (c) reacting the product of step (b) with $R^1$—COCl in the presence of at least one Base I, wherein $R^1$ is selected from the group consisting of $C_1$-$C_{12}$ alkyl, benzyl, aryl, and heteroaryl, and the at least one Base I is selected form the group consisting of pyridine, NMI, 2,6-lutidine, 2,4,6-collidine, DBU, DABCO, tetramethylguanidine, triethylamine, diisopropylethylamine, and mixtures thereof, to form the compound of Formula (I-4);

(ii) reacting the compound of Formula (I-4) with at least one Base D to form a compound of Formula (I-4¹)

-continued

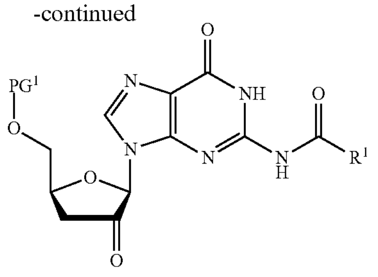

(I-4[1])

wherein the at least one Base D is selected from the group consisting of lithium hydroxide, lithium methoxide, lithium ethoxide, lithium isopropoxide, lithium tert-butoxide, sodium hydroxide, sodium methoxide, sodium ethoxide, sodium isopropoxide, sodium tert-butoxide, and mixtures thereof; and (iii) reacting the compound of Formula (I-4[1]) with at least one Acid A to form a compound of Formula (I-3)

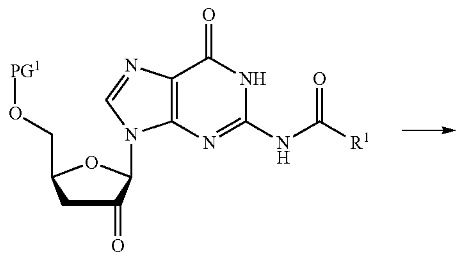

(I-4[1])

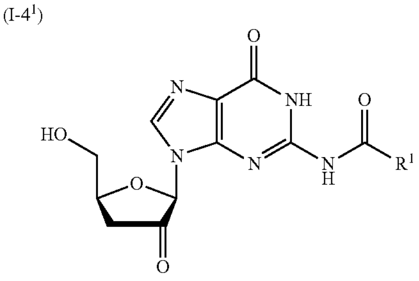

(I-3)

wherein the at least one Acid A is selected from the group consisting of TFA, HCl, $H_2SO_4$, methanesulfonyl hydroxide, para-toluenesulfonyl hydroxide, and mixtures thereof;

(iv) reacting the compound of Formula (I-3) with at least one Fluorinating Agent A in the presence of at least one Catalyst B, at least one Base C, and water to provide a compound of Formula (I-2):

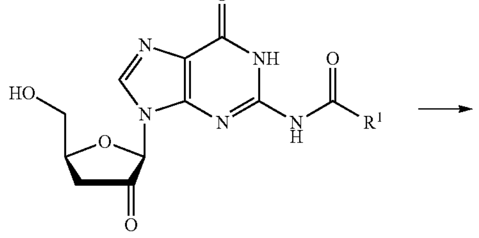

(I-3)

-continued

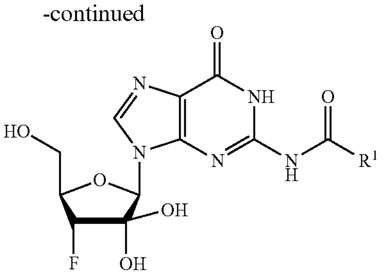

(I-2)

wherein the at least one Fluorinating Agent A is selected from the group consisting of N-fluorobenzenesulfonimide, 1-chloromethyl-4-fluoro-1,4-diazoniabicyclo[2.2.2] octane bis(tetrafluoroborate), 1-fluoro-4-methyl-1,4-diazoniabicyclo[2.2.2] octanebis(tetrafluoroborate), N-fluoropyridinium triflate, and N-fluoropyridinium tetrafluoroborate, and mixtures thereof;

the at least one Catalyst B is selected from the group consisting of ($C_1$-$C_8$ alkyl)$NH_2$,

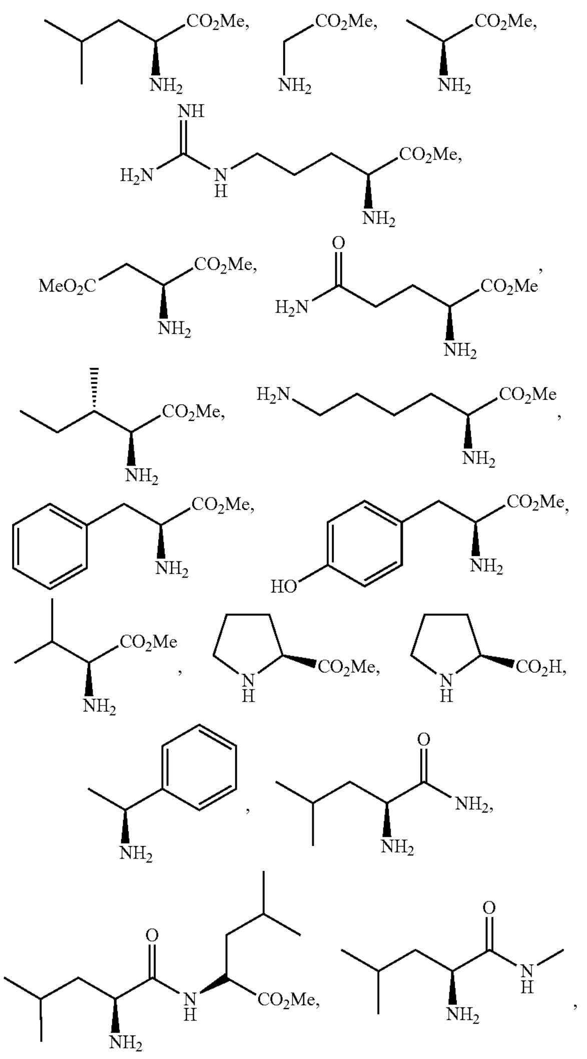

-continued

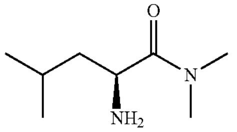

, and

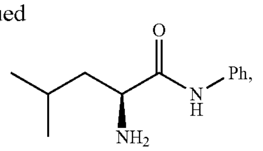

and mixtures thereof, and the at least one Base C is selected from the group consisting of lithium carbonate, sodium carbonate, sodium bicarbonate, potassium carbonate, ammonium carbonate, cesium carbonate, lithium dihydrogen phosphate, sodium hydrogen phosphate, sodium dihydrogen phosphate, sodium phosphate, potassium hydrogen phosphate, potassium dihydrogen phosphate, potassium phosphate, ammonium hydrogen phosphate, sodium acetate, ammonium acetate, sodium benzoate, sodium hydrogen sulfate, potassium hydrogen sulfate, potassium fluoride, cesium fluoride, sodium formate, and ammonium formate, and mixtures thereof;

(v) reacting the compound of Formula (I-2) with at least one Reducing Agent to provide a compound of Formula (I-1):

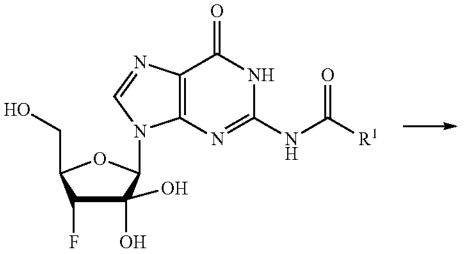

(I-2)

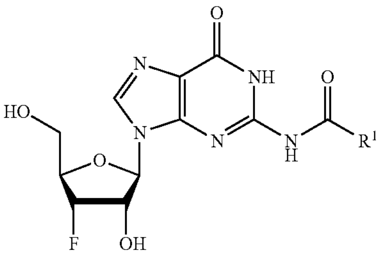

(I-1)

wherein the at least one Reducing Agent is at least one chemical reducing agent selected from the group consisting of sodium triacetoxy borohydride, sodium cyanoborohydride, sodium borohydride, sodium tris(trifluoroacetoxy) borohydride, tetramethylammonium triacetoxyborohydride, sodium tri(2-methylacetoxy) borohydride, sodium tri(2-phenylacetoxy) borohydride, and mixtures thereof; and (vi) reacting the compound of Formula (I-1) with a thiophosphorylating agent in the presence of at least one Catalyst A and at least one Base A in the presence of at least one Solvent A, to form a compound of Formula (I-1') and then reacting the compound of Formula (I-1') with at least one Base B in the presence of at least one Solvent B:

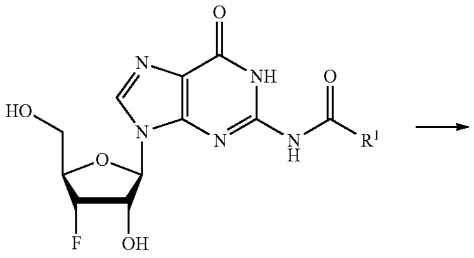

(I-1)

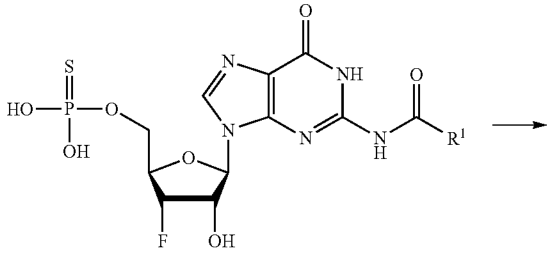

(I-1')

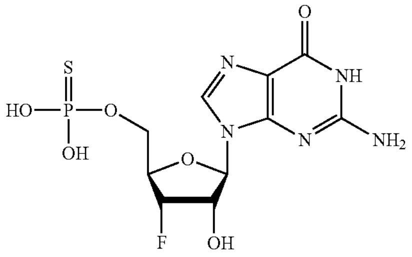

(I)

wherein the at least one thiophosphorylating agent is $PSCl_3$; and the at least one Catalyst A is selected from the group consisting of

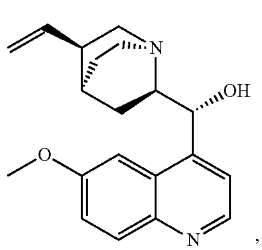

,

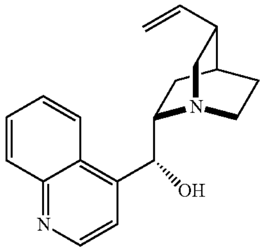

,

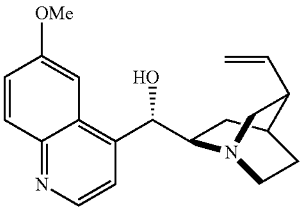

,

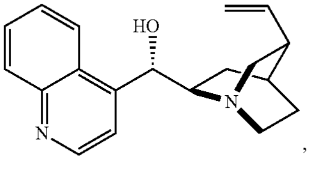

,

-continued

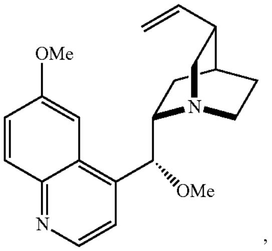

,

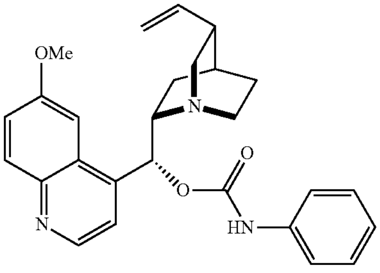

,

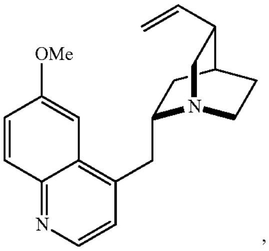

,

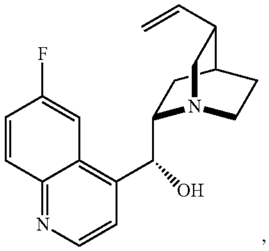

,

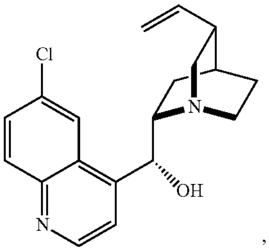

,

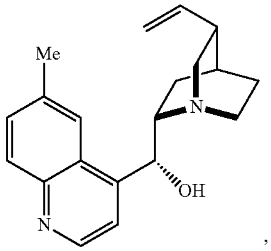

,

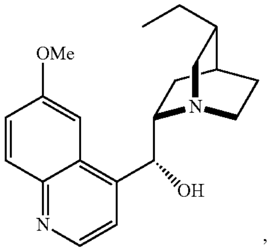

,

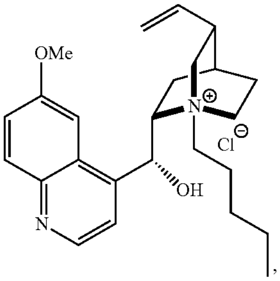

,

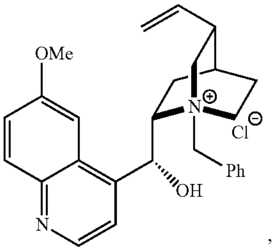

,

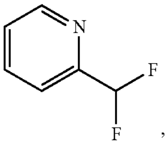

,

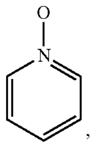

,

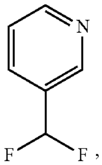

,

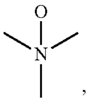

,

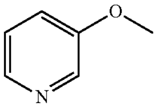

,

-continued

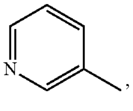

,

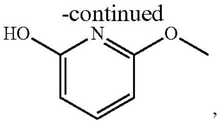

,

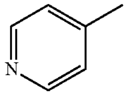

,

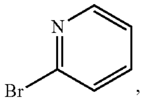

,

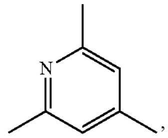

, and

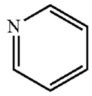

;

the at least one Base A is selected from the group consisting of 2,6-lutidine, pyridine, $Et_3N$, 1,8-bis(dimethylamino) naphthalene, 2,6-lutidine, 2,4-lutidine, 2-methyl-pyridine, trimethylpyridine, 3-methoxy-pyridine, 4-methyl-pyridine, quinuclidine, Hunig's base, 3-methyl-pyridine, and 2,6-di-tert-butyl-4-methyl pyridine, and mixtures thereof;

the at least one Solvent A is selected from the group consisting of THF, MeCN, acetone, DMPU, HFIP, TFE, DME, DMAc, 2-Me-THF, EtOAc, and MIBK, and mixtures thereof;

the at least one Base B is selected from the group consisting of NaOH, KOH, $NH_4OH$, and $MeNH_2$, and mixtures thereof;

the at least one Solvent B is selected from the group consisting of MeOH, IPA, and EtOH, and mixtures thereof.

In aspects of the seventh embodiment, the process further comprises forming a sodium or potassium salt of the compound of Formula (I).

In an eighth embodiment, the disclosure provides a process for the preparation of compounds of Formula (I), or a pharmaceutically acceptable salt, hydrate, or solvate thereof:

(I)

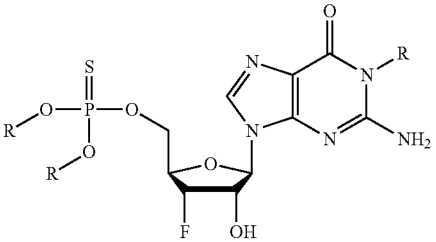

wherein each R is independently selected from the group consisting of H, Na, and K, comprising (i) selectively functionalizing guanosine to provide a compound of Formula (I-4):

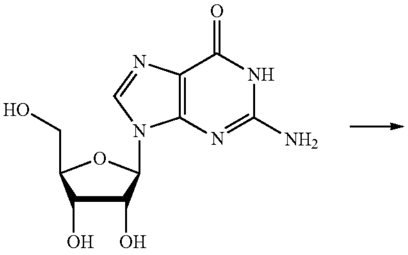

-continued

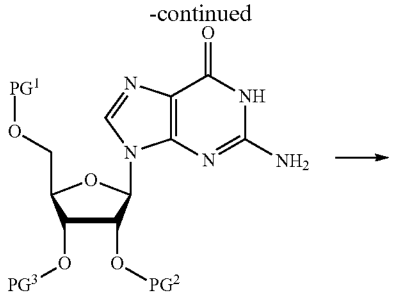

(I-4[3])

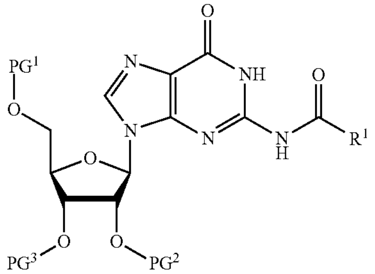

(I-4)

wherein protecting group $PG^1$ is selected from the group consisting of isobutyryl, pivaloyl, trityl, tert-butyldiphenylsilyl, and tert-butyldimethylsilyl; protecting group $PG^2$ is selected from the group consisting of isobutyryl, pivaloyl, methanesulfonyl, ethanesulfonyl, benzenesulfonyl, 2-nitrobenzenesulfonyl, 4-nitrobenzensulfonyl, 4-chlorobenzenesulfonyl, 4-fluorobenzenesulfonyl, and p-toluenesulfonyl; and protecting group $PG^3$ is selected from the group consisting of methanesulfonyl, ethanesulfonyl, benzenesulfonyl, 2-nitrobenzenesulfonyl, 4-nitrobenzene sulfonyl, 4-chlorobenzenesulfonyl, 4-fluorobenzenesulfonyl, and p-toluenesulfonyl;

wherein the selectively functionalizing guanosine to provide a compound of Formula (I-4) comprises:

(a) reacting guanosine with $PG^1$-Cl in the presence of at least one Base G, wherein the at least one Base G is selected from the group consisting of pyridine, NMI, 2,6-lutidine, 2,4,6-collidine, DBU, DABCO, tetramethylguanidine, triethylamine, diisopropylethylamine, and mixtures thereof, to form a product of step (a);

(b) reacting the product of step (a) with $PG^2$-Cl and $PG^3$-Cl in the presence of at least one Base H, wherein the at least one Base H is selected from the group consisting of pyridine, NMI, 2,6-lutidine, 2,4,6-collidine, DBU, DABCO, tetramethylguanidine, triethylamine, diisopropylethylamine, and mixtures thereof, to form a product of step (b); and (c) reacting the product of step (b) with $R^1$—COCl in the presence of at least one Base I, wherein $R^1$ is selected from the group consisting of $C_1$-$C_{12}$ alkyl, benzyl, aryl, and heteroaryl, and the at least one Base I is selected form the group consisting of pyridine, NMI, 2,6-lutidine, 2,4,6-collidine, DBU, DABCO, tetramethylguanidine, triethylamine, diisopropylethylamine, and mixtures thereof, to form the compound of Formula (I-4);

(ii) reacting the compound of Formula (I-4) with at least one Base D to form a compound of Formula (I-4[1])

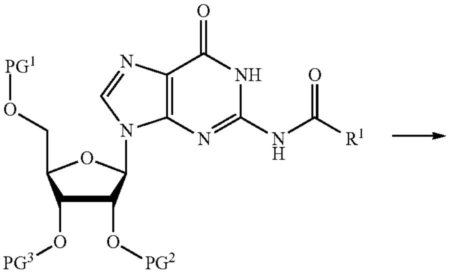

(I-4)

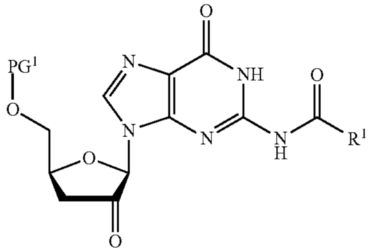

(I-4[1])

wherein the at least one Base D is selected from the group consisting of lithium hydroxide, lithium methoxide, lithium ethoxide, lithium isopropoxide, lithium tert-butoxide, sodium hydroxide, sodium methoxide, sodium ethoxide, sodium isopropoxide, sodium tert-butoxide, and mixtures thereof; and (iii) reacting the compound of Formula (I-4[1]) with at least one Acid A to form a compound of Formula (I-3)

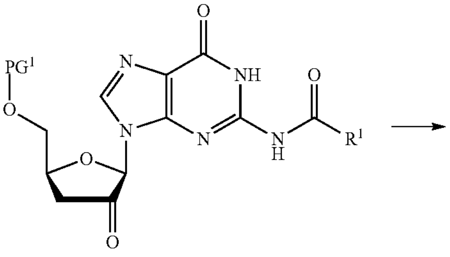

(I-4[1])

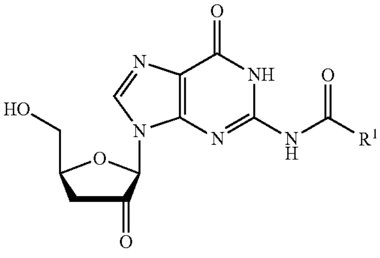

(I-3)

wherein the at least one Acid A is selected from the group consisting of TFA, HCl, $H_2SO_4$, methanesulfonyl hydroxide, para-toluenesulfonyl hydroxide, and mixtures thereof;

(iv) reacting the compound of Formula (I-3) with at least one Fluorinating Agent A in the presence of at least one Catalyst B, at least one Base C, and water to provide a compound of Formula (I-2):

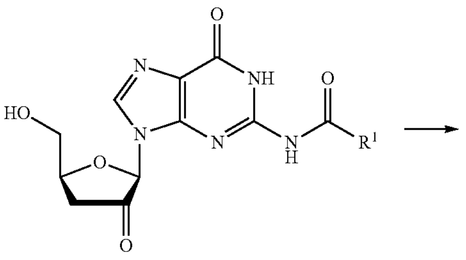

(I-3)

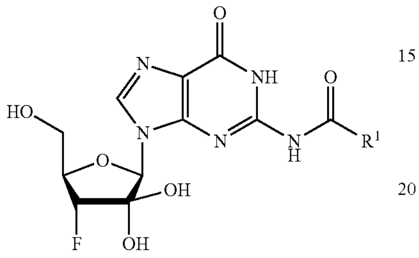

(I-2)

wherein the at least one Fluorinating Agent A is selected from the group consisting of N-fluorobenzenesulfonimide, 1-chloromethyl-4-fluoro-1,4-diazoniabicyclo[2.2.2] octane bis(tetrafluoroborate), 1-fluoro-4-methyl-1,4-diazoniabicyclo[2.2.2] octanebis(tetrafluoroborate), N-fluoropyridinium triflate, and N-fluoropyridinium tetrafluoroborate, and mixtures thereof;

the at least one Catalyst B is selected from the group consisting of ($C_1$-$C_8$ alkyl)$NH_2$,

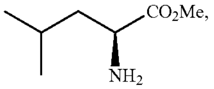

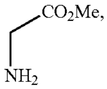

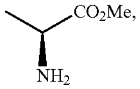

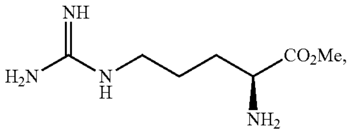

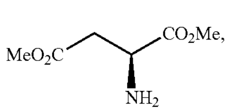

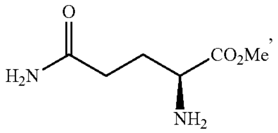

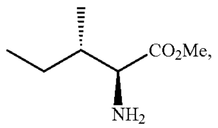

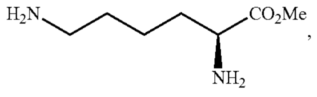

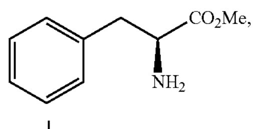

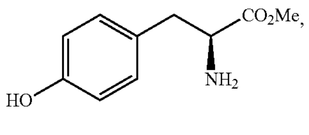

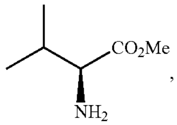

,

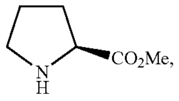

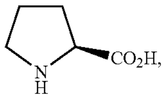

-continued

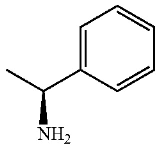

,

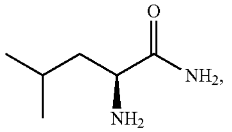

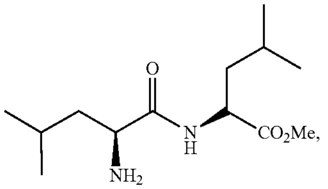

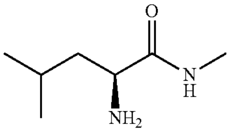

,

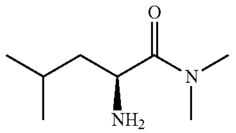

, and

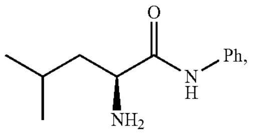

and mixtures thereof, and the at least one Base C is selected from the group consisting of lithium carbonate, sodium carbonate, sodium bicarbonate, potassium carbonate, ammonium carbonate, cesium carbonate, lithium dihydrogen phosphate, sodium hydrogen phosphate, sodium dihydrogen phosphate, sodium phosphate, potassium hydrogen phosphate, potassium dihydrogen phosphate, potassium phosphate, ammonium hydrogen phosphate, sodium acetate, ammonium acetate, sodium benzoate, sodium hydrogen sulfate, potassium hydrogen sulfate, potassium fluoride, cesium fluoride, sodium formate, and ammonium formate, and mixtures thereof;

(v) reacting the compound of Formula (I-2) with at least one Reducing Agent to provide a compound of Formula (I-1):

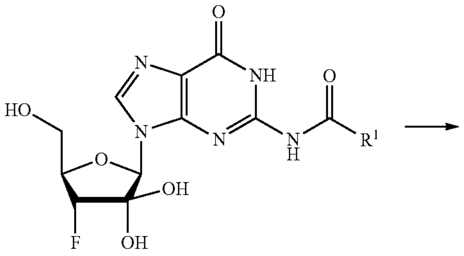

(I-2)

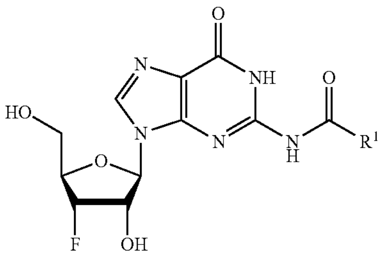

(I-1)

wherein the at least one Reducing Agent is at least one biocatalytic reducing agent selected from enzymatic reducing agents; and (vi) reacting the compound of Formula (I-1) with a thiophosphorylating agent in the presence of at least one Catalyst A and at least one Base A in the presence of at least one Solvent A, to form a compound of Formula (I-1') and then reacting the compound of Formula (I-1') with at least one Base B in the presence of at least one Solvent B:

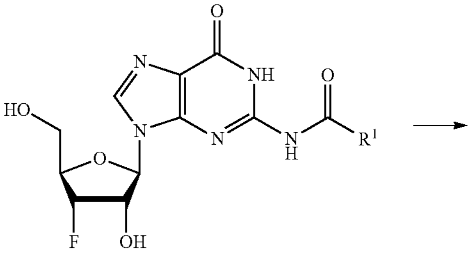

(I-1)

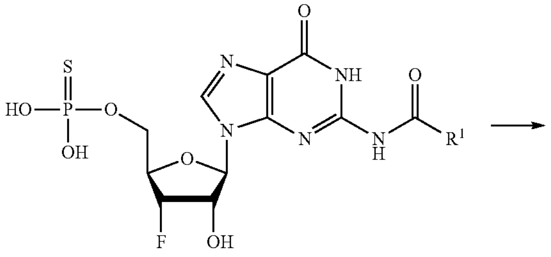

(I-1')

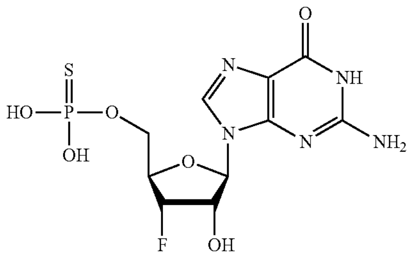

(I)

wherein the at least one thiophosphorylating agent is $PSCl_3$; and the at least one Catalyst A is selected from the group consisting of

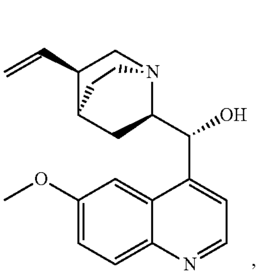

,

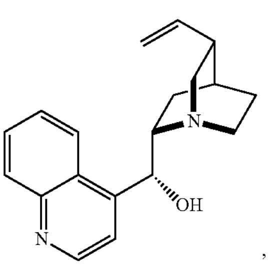

,

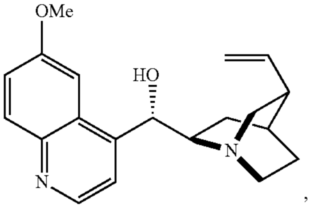

,

-continued

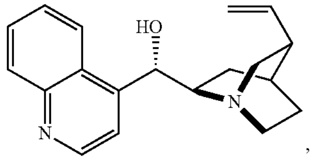

,

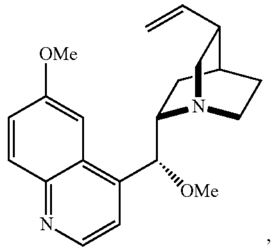

,

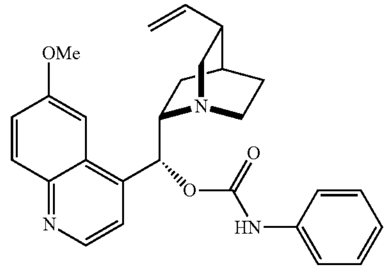

,

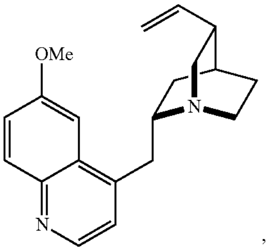

,

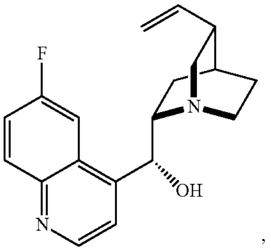

,

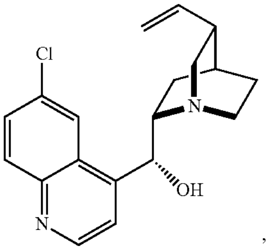

,

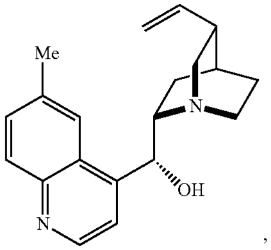

,

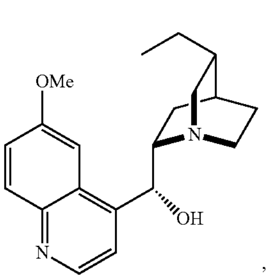

,

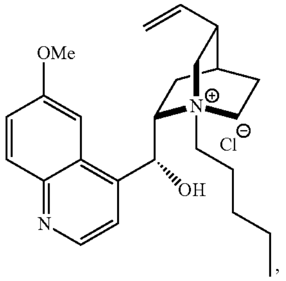

,

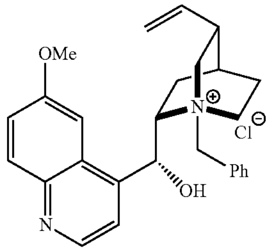

,

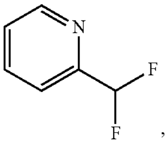

,

-continued

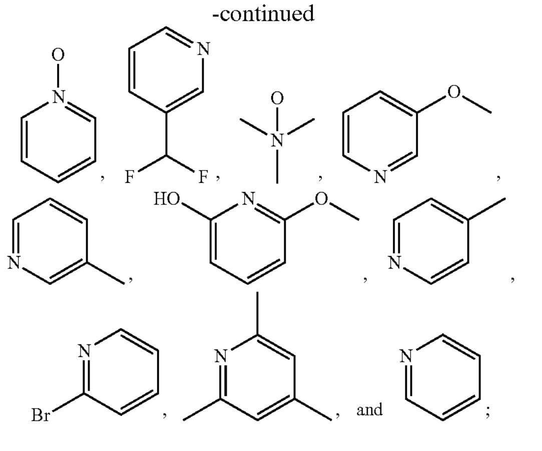

the at least one Base A is selected from the group consisting of 2,6-lutidine, pyridine, $Et_3N$, 1,8-bis(dimethylamino) naphthalene, 2,6-lutidine, 2,4-lutidine, 2-methyl-pyridine, trimethylpyridine, 3-methoxy-pyridine, 4-methyl-pyridine, quinuclidine, Hunig's base, 3-methyl-pyridine, and 2,6-di-tert-butyl-4-methyl pyridine, and mixtures thereof;

the at least one Solvent A is selected from the group consisting of THF, MeCN, acetone, DMPU, HFIP, TFE, DME, DMAc, 2-Me-THF, EtOAc, and MIBK, and mixtures thereof;

the at least one Base B is selected from the group consisting of NaOH, KOH, $NH_4O$, and $MeNH_2$, and mixtures thereof;

the at least one Solvent B is selected from the group consisting of MeOH, IPA, and EtOH, and mixtures thereof.

In aspects of the eighth embodiment, the process further comprises forming a sodium or potassium salt of the compound of Formula (I).

In aspects of the eighth embodiment, the at least one Reducing Agent is selected from one or more ketoreductase enzymes that have been pre-treated with isopropanol to a volume % of at least about 20% isopropanol, and then centrifuged to remove protein components that precipitate under such conditions. In specific aspects, the at least one Reducing Agent is selected from one or more ketoreductase enzymes that have been pre-treated with isopropanol to a volume % of at least about 25% isopropanol and centrifuged to remove protein components that precipitate under such conditions. Specific aspects of the eighth embodiment further comprise pre-treating the at least one Reducing Agent selected from one or more ketoreductase enzymes with isopropanol to a volume % of at least about 20% isopropanol; still further specific instances of such processes further comprise removing precipitated proteins from pretreated ketoreductase enzyme Reducing Agents by centrifuge. Specific aspects of the eighth embodiment further comprise pre-treating the at least one Reducing Agent selected from one or more ketoreductase enzymes with isopropanol to a volume % of at least about 25% isopropanol; still further specific instances of such processes further comprise removing precipitated proteins from pretreated ketoreductase enzyme Reducing Agents by centrifuge.

In a ninth embodiment, the disclosure provides a process for the preparation of compounds of Formula (I), or a pharmaceutically acceptable salt, hydrate, or solvate thereof:

(I)

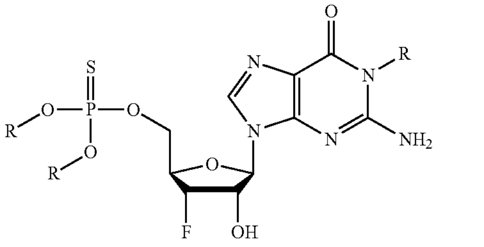

wherein each R is independently selected from the group consisting of H, Na, and K, comprising (i) selectively functionalizing guanosine to provide a compound of Formula (I-4):

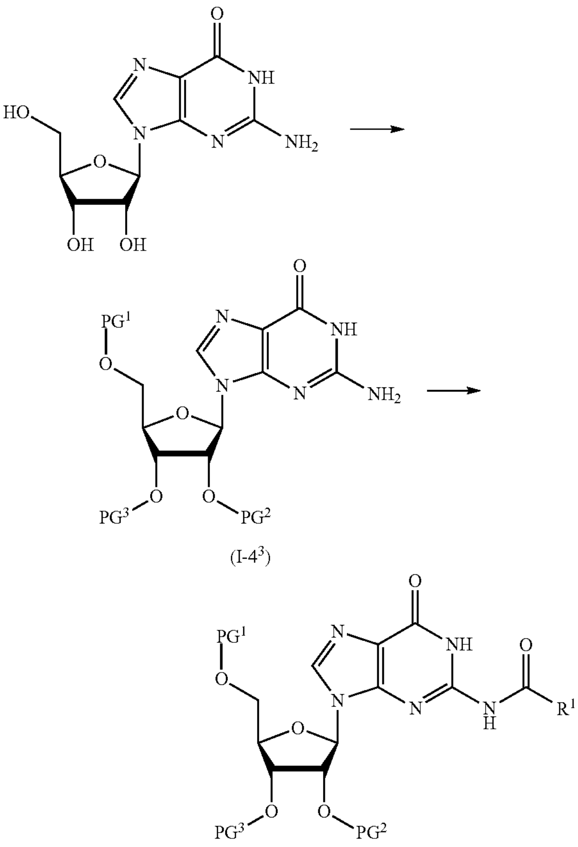

(I-4³)

(I-4)

wherein protecting group $PG^1$ is selected from the group consisting of isobutyryl, pivaloyl, trityl, tert-butyldiphenylsilyl, and tert-butyldimethylsilyl; protecting group $PG^2$ is selected from the group consisting of isobutyryl, pivaloyl, methanesulfonyl, ethanesulfonyl, benzenesulfonyl, 2-nitrobenzenesulfonyl, 4-nitrobenzensulfonyl, 4-chlorobenzenesulfonyl, 4-fluorobenzenesulfonyl, and p-toluenesulfonyl; and protecting group $PG^3$ is selected from the group consisting of methanesulfonyl, ethanesulfonyl, benzenesulfonyl, 2-nitrobenzenesulfonyl, 4-nitrobenzene sulfonyl, 4-chlorobenzenesulfonyl, 4-fluorobenzenesulfonyl, and p-toluenesulfonyl;

wherein the selectively functionalizing guanosine to provide a compound of Formula (I-4) comprises:

(a) reacting guanosine with $PG^1$-Cl in the presence of at least one Base G, wherein the at least one Base G is selected from the group consisting of pyridine, NMI, 2,6-lutidine, 2,4,6-collidine, DBU, DABCO, tetramethylguanidine, triethylamine, diisopropylethylamine, and mixtures thereof, to form a compound of step (a);

(b) reacting the product of step (a) with $PG^2$-Cl and $PG^3$-Cl in the presence of at least one Base H, wherein the at least one Base H is selected from the group consisting of pyridine, NMI, 2,6-lutidine, 2,4,6-collidine, DBU, DABCO, tetramethylguanidine, triethylamine, diisopropylethylamine, and mixtures thereof, to form a compound of step (b); and (c) reacting the product of step b) with $R^1$—COCl in the presence of at least one Base I, wherein $R^1$ is selected from the group consisting of $C_1$-$C_{12}$ alkyl, benzyl, aryl, and heteroaryl, and the at least one Base I is selected form the group consisting of pyridine, NMI, 2,6-lutidine, 2,4,6-collidine, DBU, DABCO, tetramethylguanidine, triethylamine, diisopropylethylamine, and mixtures thereof, to form the compound of Formula (I-4);

(ii) reacting the compound of Formula (I-4) with at least one Base E to form a compound of Formula (I-4$^1$)

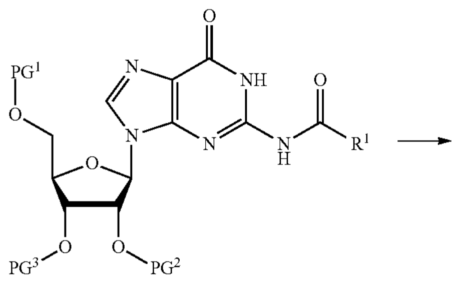

(I-4)

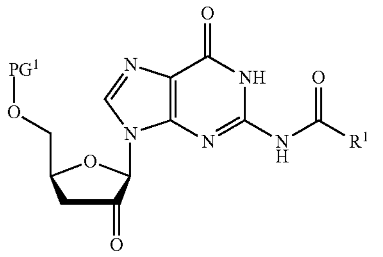

(I-4$^1$)

wherein at least one Base E is selected from the group consisting of lithium hydroxide, lithium methoxide, lithium ethoxide, lithium isopropoxide, lithium tert-butoxide, sodium hydroxide, sodium methoxide, sodium ethoxide, sodium isopropoxide, sodium tert-butoxide, and mixtures thereof;

(iii) reacting the compound of Formula (I-4$^1$) with at least one Fluorinating Agent B in the presence of at least one Catalyst C, at least one Base F, and water to form a product, followed by reacting the product with at least one Acid B to form a compound of Formula (I-2):

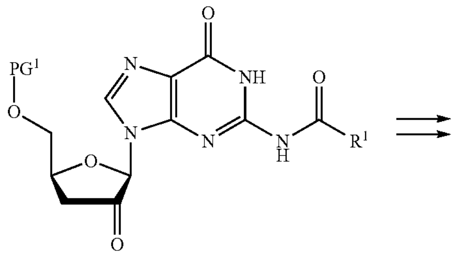

(I-4$^1$)

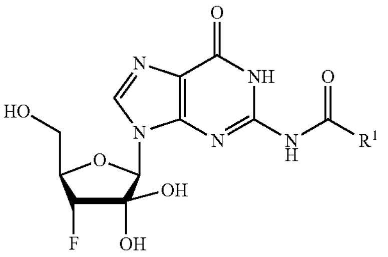

(I-2)

wherein the at least one Fluorinating Agent B is selected from the group consisting of N-fluorobenzenesulfonimide, 1-chloromethyl-4-fluoro-1,4-diazoniabicyclo[2.2.2] octane bis(tetrafluoroborate), 1-fluoro-4-methyl-1,4-diazoniabicyclo[2.2.2] octanebis(tetrafluoroborate), N-fluoropyridinium triflate, and N-fluoropyridinium tetrafluoroborate, and mixtures thereof, the at least one Catalyst C is selected from the group consisting of ($C_1$-$C_8$ alkyl)$NH_2$,

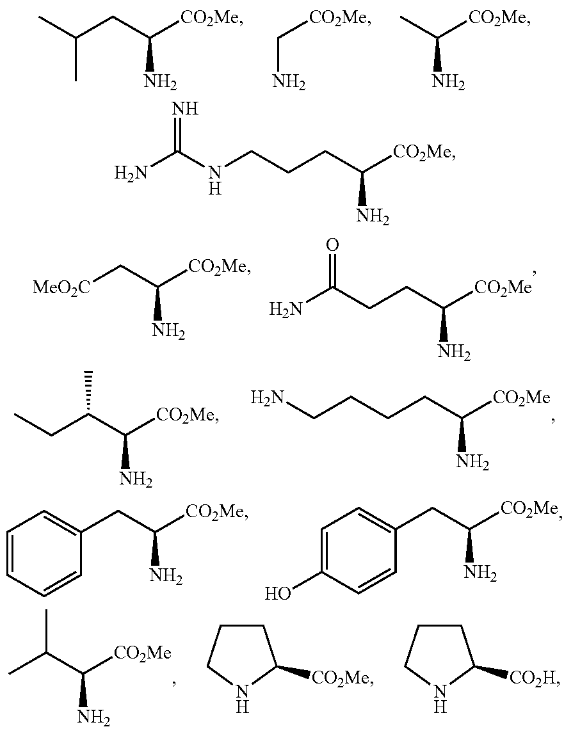

-continued

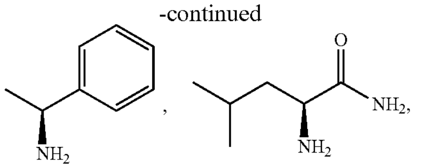

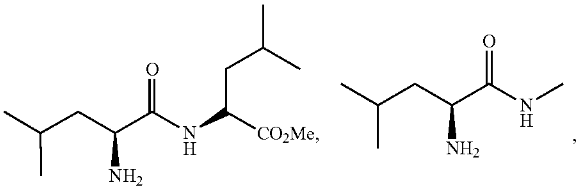

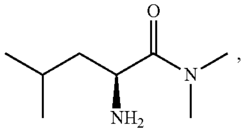

and

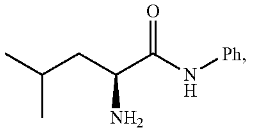

and mixtures thereof, the at least one Base F is selected from the group consisting of lithium carbonate, sodium carbonate, sodium bicarbonate, potassium carbonate, ammonium carbonate, cesium carbonate, lithium dihydrogen phosphate, sodium hydrogen phosphate, sodium dihydrogen phosphate, sodium phosphate, potassium hydrogen phosphate, potassium dihydrogen phosphate, potassium phosphate, ammonium hydrogen phosphate, sodium acetate, ammonium acetate, sodium benzoate, sodium hydrogen sulfate, potassium hydrogen sulfate, potassium fluoride, cesium fluoride, sodium formate, and ammonium formate, and mixtures thereof;

wherein the at least one Acid B is selected from the group consisting of TFA, HCl, $H_2SO_4$, methanesulfonyl hydroxide, para-toluenesulfonyl hydroxide, and mixtures thereof; and the at least one Acid B is selected from the group consisting of TFA, HCl, $H_2SO_4$, MsOH, TsOH, and mixtures thereof;

(iv) reacting the compound of Formula (I-2) with at least one Reducing Agent to provide a compound of Formula (I-1):

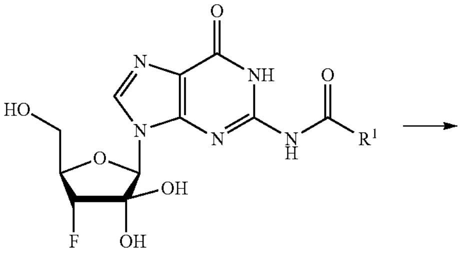

(I-2)

-continued

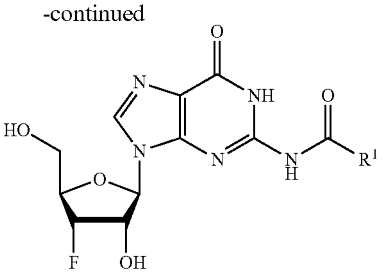

(I-1)

wherein the at least one Reducing Agent is at least one chemical reducing agent selected from the group consisting of sodium triacetoxy borohydride, sodium cyanoborohydride, sodium borohydride, sodium tris(trifluoroacetoxy) borohydride, tetramethylammonium triacetoxyborohydride, sodium tri(2-methylacetoxy) borohydride, sodium tri(2-phenylacetoxy) borohydride, and mixtures thereof, and (v) reacting the compound of Formula (I-1) with a thiophosphorylating agent in the presence of at least one Catalyst A and at least one Base A in the presence of at least one Solvent A, to form a compound of Formula (I-1') and then reacting the compound of Formula (I-1') with at least one Base B in the presence of at least one Solvent B:

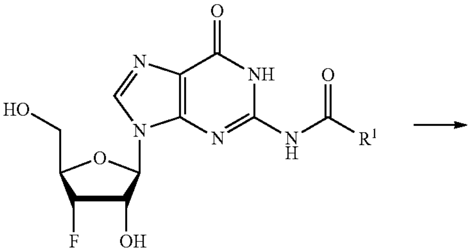

(I-1)

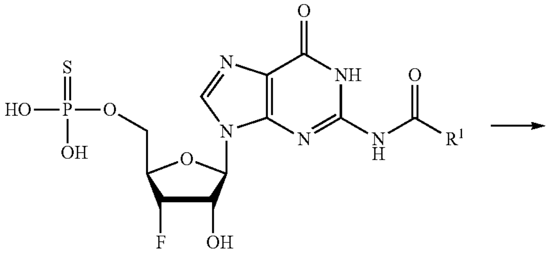

(I-1')

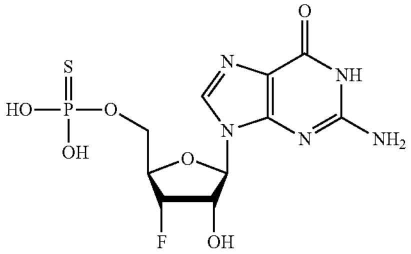

(I)

wherein the at least one thiophosphorylating agent is $PSCl_3$; and the at least one Catalyst A is selected from the group consisting of

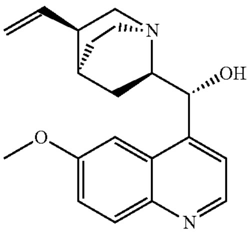
,
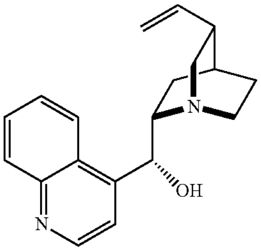
,
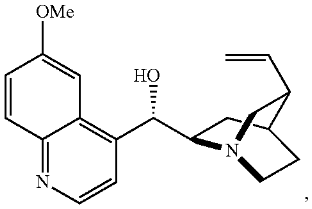
,
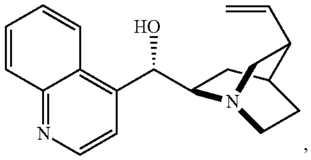
,
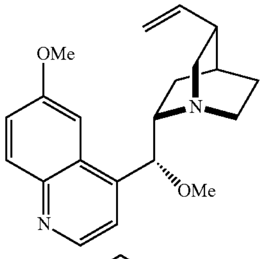
,
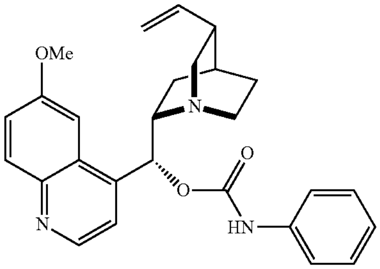
,
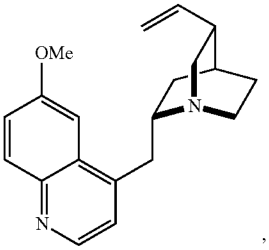
,
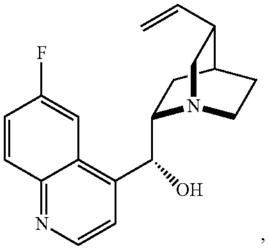
,
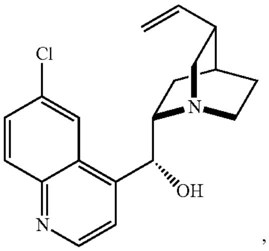
,
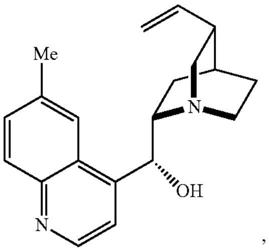
, -continued

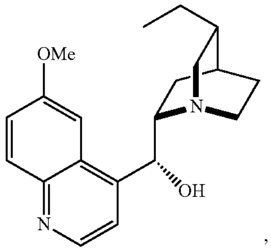
,
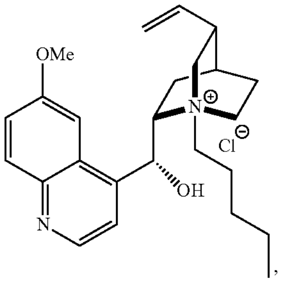
,
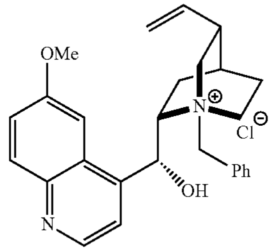
,
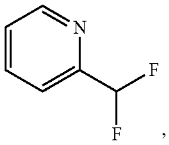
,
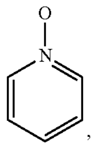
,
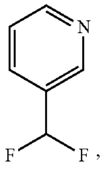
,
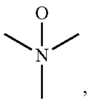
,
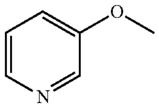
,
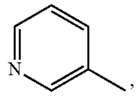
,
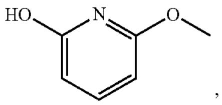
,
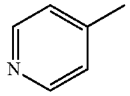
,
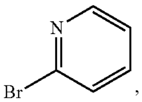
,
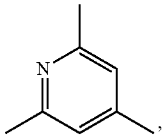
, and
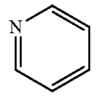
;

the at least one Base A is selected from the group consisting of 2,6-lutidine, pyridine, $Et_3N$, 1,8-bis(dimethylamino) naphthalene, 2,6-lutidine, 2,4-lutidine, 2-methyl-pyridine, trimethylpyridine, 3-methoxy-pyridine, 4-methyl-pyridine, quinuclidine, Hunig's base, 3-methyl-pyridine, and 2,6-di-tert-butyl-4-methyl pyridine, and mixtures thereof;

the at least one Solvent A is selected from the group consisting of THF, MeCN, acetone, DMPU, HFIP, TFE, DME, DMAc, 2-Me-THF, EtOAc, and MIBK, and mixtures thereof;

the at least one Base B is selected from the group consisting of NaOH, KOH, $NH_4OH$, and $MeNH_2$, and mixtures thereof;

the at least one Solvent B is selected from the group consisting of MeOH, IPA, and EtOH, and mixtures thereof.

In aspects of the ninth embodiment, the process further comprises forming a sodium or potassium salt of the compound of Formula (I).

In a tenth embodiment, the disclosure provides a process for the preparation of compounds of Formula (I), or a pharmaceutically acceptable salt, hydrate, or solvate thereof.

(I)

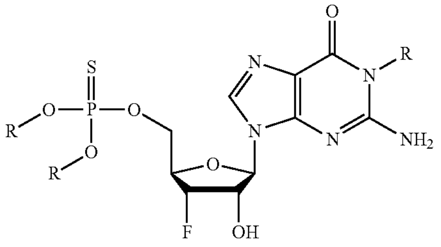

wherein each R is independently selected from the group consisting of H, Na, and K, comprising (i) selectively functionalizing guanosine to provide a compound of Formula (I-4):

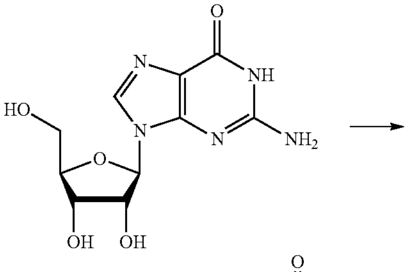

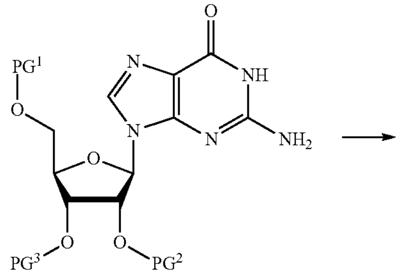

(I-4[3])

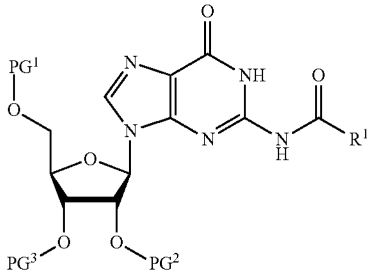

(I-4)

wherein protecting group $PG^1$ is selected from the group consisting of isobutyryl, pivaloyl, trityl, tert-butyldiphenylsilyl, and tert-butyldimethylsilyl; protecting group $PG^2$ is selected from the group consisting of isobutyryl, pivaloyl, methanesulfonyl, ethanesulfonyl, benzenesulfonyl, 2-nitrobenzenesulfonyl, 4-nitrobenzensulfonyl, 4-chlorobenzenesulfonyl, 4-fluorobenzenesulfonyl, and p-toluenesulfonyl; and protecting group $PG^3$ is selected from the group consisting of methanesulfonyl, ethanesulfonyl, benzenesulfonyl, 2-nitrobenzenesulfonyl, 4-nitrobenzene sulfonyl, 4-chlorobenzenesulfonyl, 4-fluorobenzenesulfonyl, and p-toluenesulfonyl;

wherein the selectively functionalizing guanosine to provide a compound of Formula (I-4) comprises:

a) reacting guanosine with $PG^1$-Cl in the presence of at least one Base G, wherein the at least one Base G is selected from the group consisting of pyridine, NMI, 2,6-lutidine, 2,4,6-collidine, DBU, DABCO, tetramethylguanidine, triethylamine, diisopropylethylamine, and mixtures thereof, to form a product of step (a);

(b) reacting the product of step (a) with $PG^2$-Cl and $PG^3$-Cl in the presence of at least one Base H, wherein the at least one Base H is selected from the group consisting of pyridine, NMI, 2,6-lutidine, 2,4,6-collidine, DBU, DABCO, tetramethylguanidine, triethylamine, diisopropylethylamine, and mixtures thereof, to form a product of step (b); and (c) reacting the product of step (b) with $R^1$—COCl in the presence of at least one Base I, wherein $R^1$ is selected from the group consisting of $C_1$-$C_{12}$ alkyl, benzyl, aryl, and heteroaryl, and the at least one Base I is selected form the group consisting of pyridine, NMI, 2,6-lutidine, 2,4,6-collidine, DBU, DABCO, tetramethylguanidine, triethylamine, diisopropylethylamine, and mixtures thereof, to form the compound of Formula (I-4);

(ii) reacting the compound of Formula (I-4) with at least one Base E to form a compound of Formula (I-4[1])

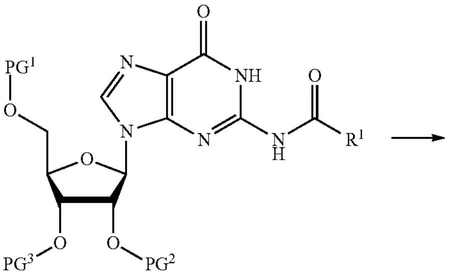

(I-4)

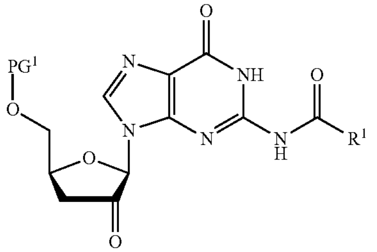

(I-4[1])

wherein the at least one Base E is selected from the group consisting of lithium hydroxide, lithium methoxide, lithium ethoxide, lithium isopropoxide, lithium tert-butoxide, sodium hydroxide, sodium methoxide, sodium ethoxide, sodium isopropoxide, sodium tert-butoxide, and mixtures thereof; and (iii) reacting the compound of Formula (I-4[1]) with at least one Fluorinating Agent B in the presence of at least one Catalyst C, at least one Base F, and water to form a product, followed by reacting the product with at least one Acid B to form a compound of Formula (I-2):

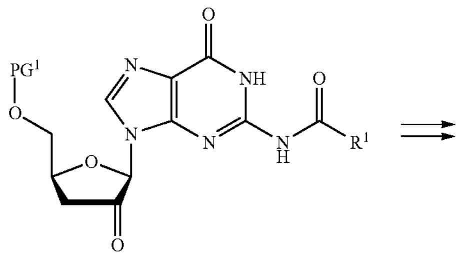

(I-4[1])

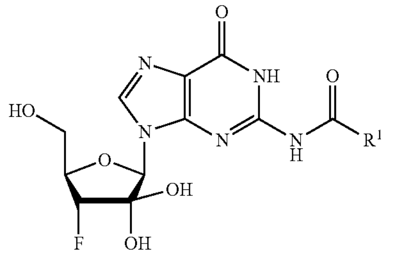

(I-2)

wherein the at least one Fluorinating Agent B is selected from the group consisting of N-fluorobenzenesulfonimide, 1-chloromethyl-4-fluoro-1,4-diazoniabicyclo[2.2.2] octane bis(tetrafluoroborate), 1-fluoro-4-methyl-1,4-diazoniabicyclo[2.2.2] octanebis(tetrafluoroborate), N-fluoropyridinium triflate, and N-fluoropyridinium tetrafluoroborate, and mixtures thereof, the at least one Catalyst C is selected from the group consisting of ($C_1$-$C_8$ alkyl)$NH_2$,

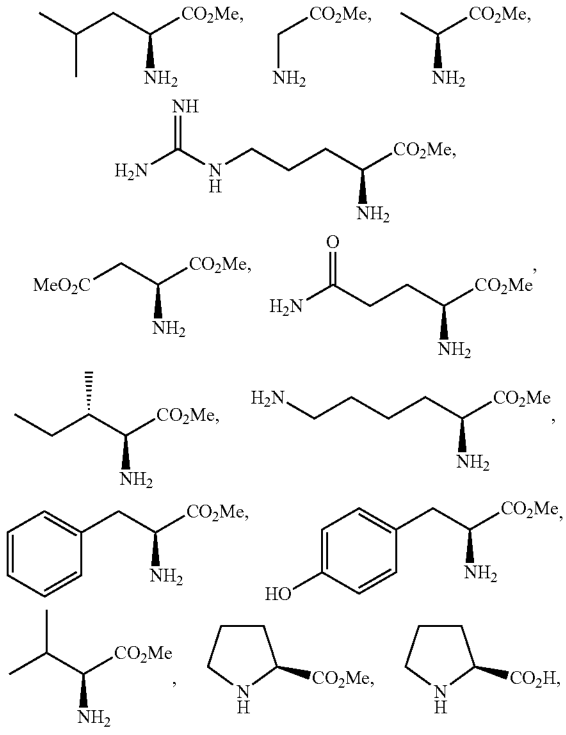

-continued

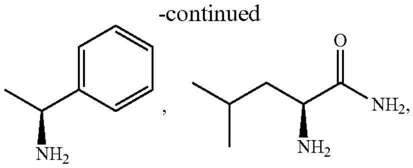

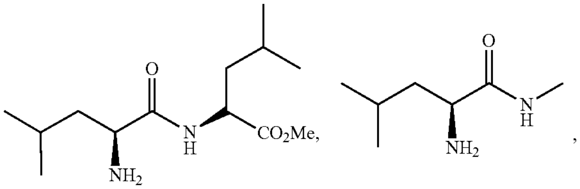

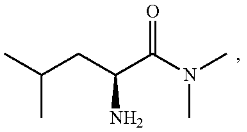

and

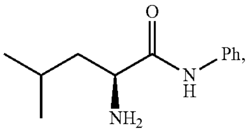

and mixtures thereof, the at least one Base F is selected from the group consisting of lithium carbonate, sodium carbonate, sodium bicarbonate, potassium carbonate, ammonium carbonate, cesium carbonate, lithium dihydrogen phosphate, sodium hydrogen phosphate, sodium dihydrogen phosphate, sodium phosphate, potassium hydrogen phosphate, potassium dihydrogen phosphate, potassium phosphate, ammonium hydrogen phosphate, sodium acetate, ammonium acetate, sodium benzoate, sodium hydrogen sulfate, potassium hydrogen sulfate, potassium fluoride, cesium fluoride, sodium formate, and ammonium formate, and mixtures thereof;

wherein the at least one Acid B is selected from the group consisting of TFA, HCl, $H_2SO_4$, methanesulfonyl hydroxide, para-toluenesulfonyl hydroxide, and mixtures thereof; and the at least one Acid B is selected from the group consisting of TFA, HCl, $H_2SO_4$, MsOH, TsOH, and mixtures thereof;

(iv) reacting the compound of Formula (I-2) with at least one Reducing Agent to provide a compound of Formula (I-1):

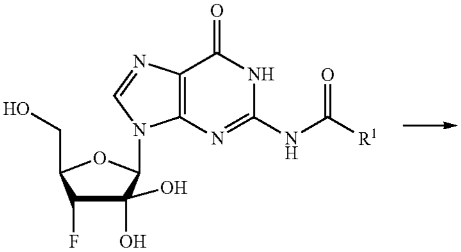

(I-2)

-continued

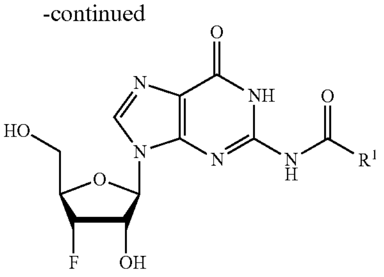

(I-1)

wherein the at least one Reducing Agent is at least one biocatalytic reducing agent selected from enzymatic reducing agents; and (v) reacting the compound of Formula (I-1) with a thiophosphorylating agent in the presence of at least one Catalyst A and at least one Base A in the presence of at least one Solvent A, to form a compound of Formula (I-1') and then reacting the compound of Formula (I-1') with at least one Base B in the presence of at least one Solvent B:

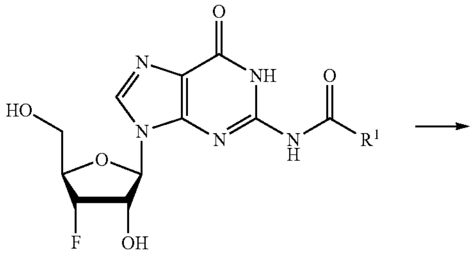

(I-1)

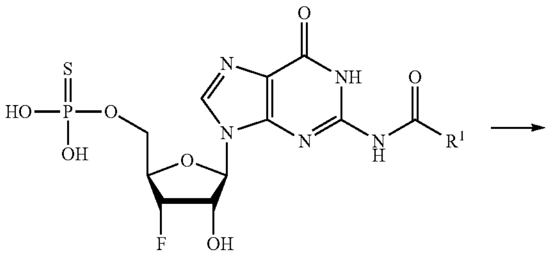

(I-1')

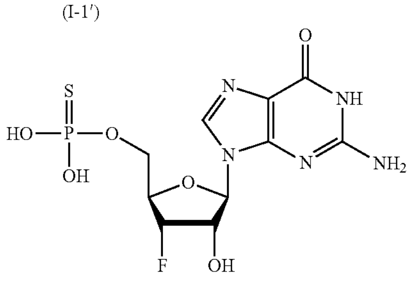

(I)

wherein the at least one thiophosphorylating agent is $PSCl_3$; and the at least one Catalyst A is selected from the group consisting of

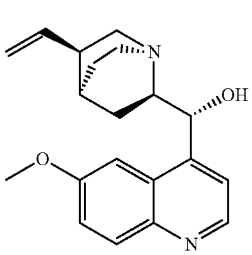

,

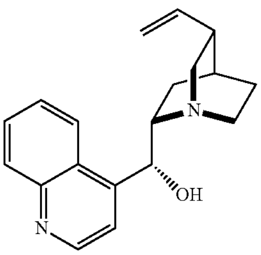

,

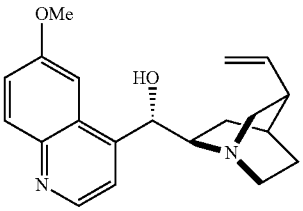

,

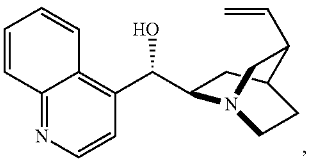

,

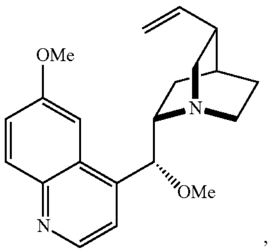

,

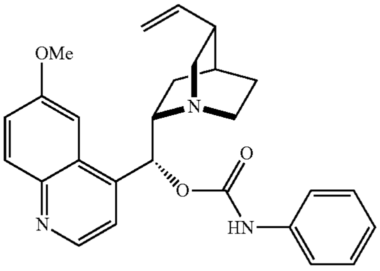

,

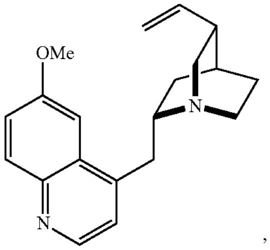

,

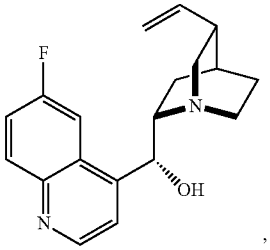

,

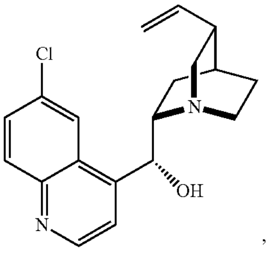

,

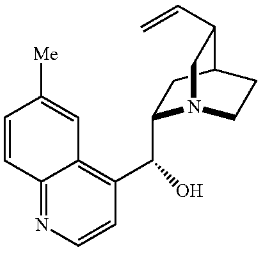

,

-continued

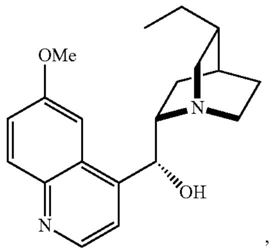,
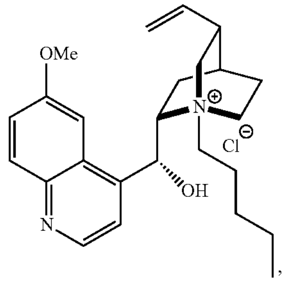,

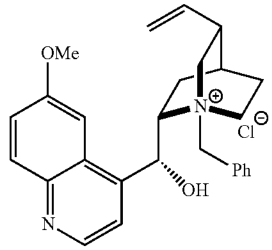,
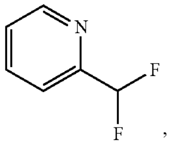,

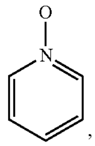, 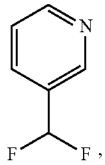, 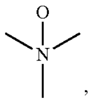, 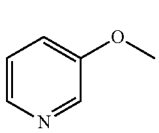,

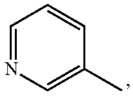, 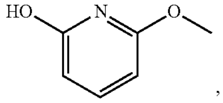, 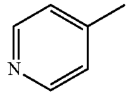,

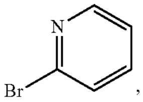, 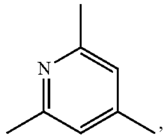, and 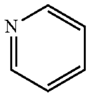;

the at least one Base A is selected from the group consisting of 2,6-lutidine, pyridine, $Et_3N$, 1,8-bis(dimethylamino) naphthalene, 2,6-lutidine, 2,4-lutidine, 2-methyl-pyridine, trimethylpyridine, 3-methoxy-pyridine, 4-methyl-pyridine, quinuclidine, Hunig's base, 3-methyl-pyridine, and 2,6-di-tert-butyl-4-methyl pyridine, and mixtures thereof;

the at least one Solvent A is selected from the group consisting of THF, MeCN, acetone, DMPU, HFIP, TFE, DME, DMAc, 2-Me-THF, EtOAc, and MIBK, and mixtures thereof;

the at least one Base B is selected from the group consisting of NaOH, KOH, $NH_4OH$, and $MeNH_2$, and mixtures thereof;

the at least one Solvent B is selected from the group consisting of MeOH, IPA, and EtOH, and mixtures thereof.

In aspects of the tenth embodiment, the process further comprises forming a sodium or potassium salt of the compound of Formula (I).

In aspects of the tenth embodiment, the at least one Reducing Agent is selected from one or more ketoreductase enzymes that have been pre-treated with isopropanol to a volume % of at least about 20% isopropanol, and then centrifuged to remove protein components that precipitate under such conditions. In specific aspects, the at least one Reducing Agent is selected from one or more ketoreductase enzymes that have been pre-treated with isopropanol to a volume % of at least about 25% isopropanol and centrifuged to remove protein components that precipitate under such conditions. Specific aspects of the tenth embodiment further comprise pre-treating the at least one Reducing Agent selected from one or more ketoreductase enzymes with isopropanol to a volume % of at least about 20% isopropanol; still further specific instances of such processes further comprise removing precipitated proteins from pretreated ketoreductase enzyme Reducing Agents by centrifuge. Specific aspects of the tenth embodiment further comprise pre-treating the at least one Reducing Agent selected from one or more ketoreductase enzymes with isopropanol to a volume % of at least about 25% isopropanol; still further specific instances of such processes further comprise removing precipitated proteins from pretreated ketoreductase enzyme Reducing Agents by centrifuge.

In an eleventh embodiment, the disclosure provides a process for the preparation of compounds of Formula (Ia), or a pharmaceutically acceptable salt, hydrate, or solvate thereof:

(Ia)

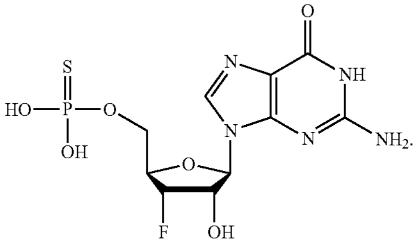

comprising (i) selectively functionalizing guanosine:

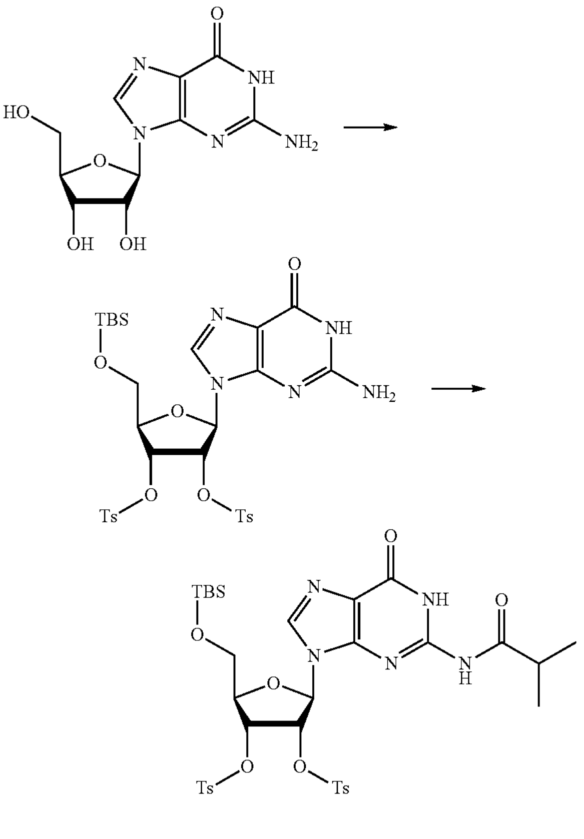

wherein the selectively functionalizing guanosine comprises:

(a) reacting guanosine with TBS-Cl in the presence of pyridine to form a product of step (a);

(b) reacting the product of step (a) with Ts-Cl and Ts-Cl in the presence of NMI to form a product of step (b); and (c) reacting the product of step (b) with isopropyl-COCl in the presence of pyridine to form a product of step (i);

(ii) reacting the product of step (i) with lithium isopropoxide, CPME, and AcOH to form a product of step (ii):

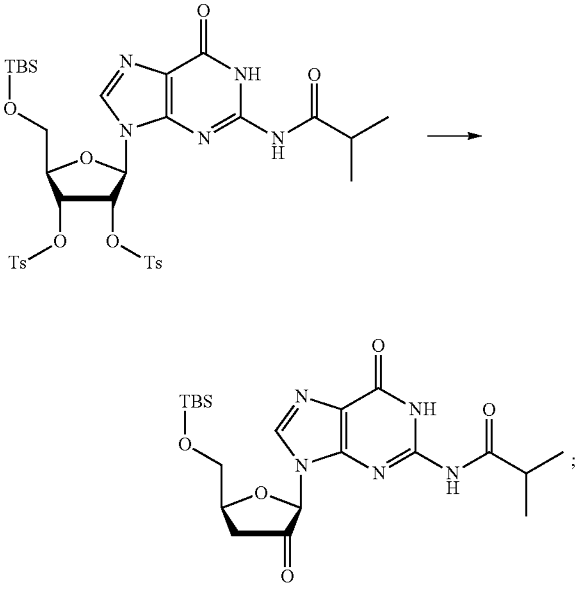

(iii) reacting the product of step (ii) with TFA to form a product of step (iii):

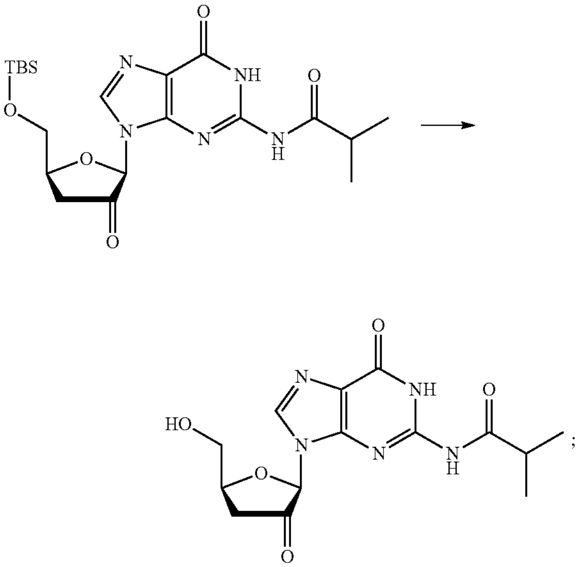

(iv) reacting the product of step (iii) with N-fluorobenzenesulfonimide in the presence of

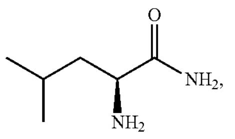

ammonium phosphate, and water, followed by TFA, to form a product of step (iv):

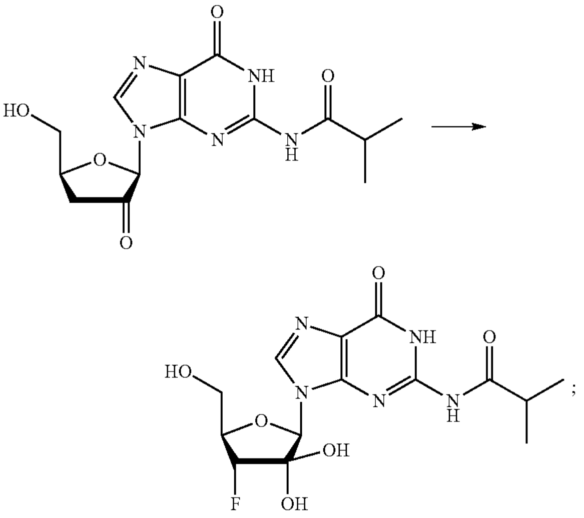

(v) reacting the product of step (iv) with sodium triacetoxyborohydride to form a product of step (iv):

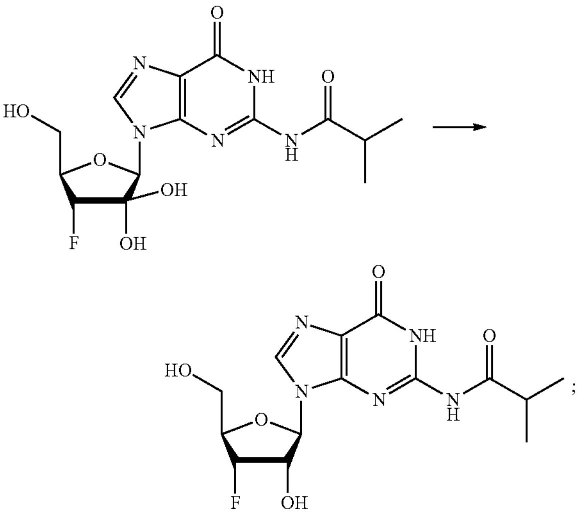

(vi) reacting the product of step (v) with $PSCl_3$ in the presence of quinine, 2,6-lutidine, and THF, followed by NaOH in the presence of MeOH and water:

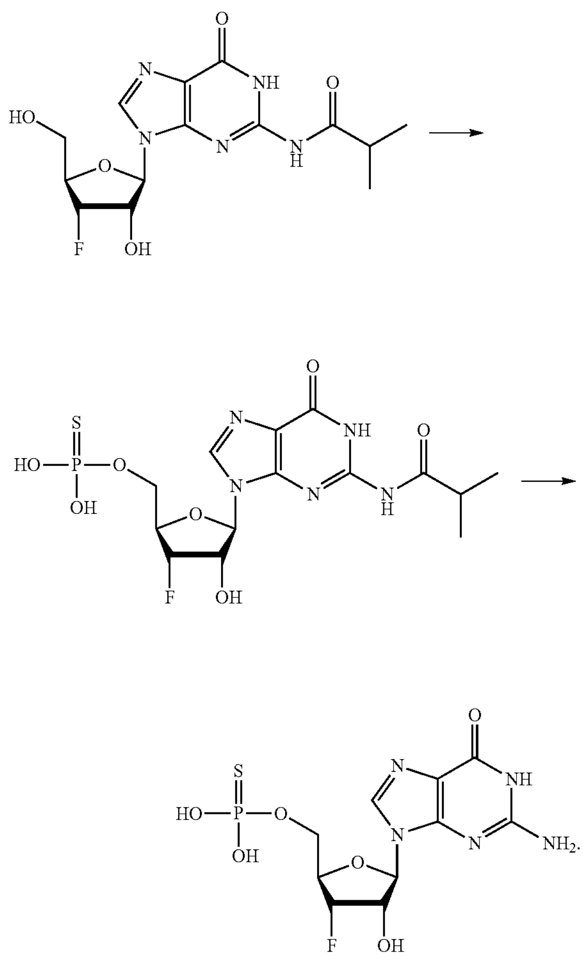

In aspects of the eleventh embodiment, the process further comprises forming a sodium or potassium salt of the compound of Formula (Ia).

In a twelfth embodiment, the disclosure provides a process for the preparation of compounds of Formula (Ia), or a pharmaceutically acceptable salt thereof:

(Ia)

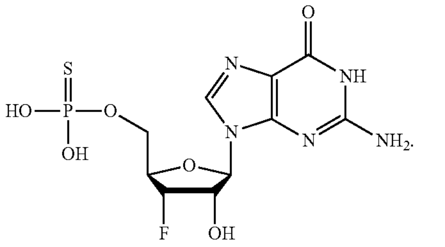

comprising (i) selectively functionalizing guanosine:

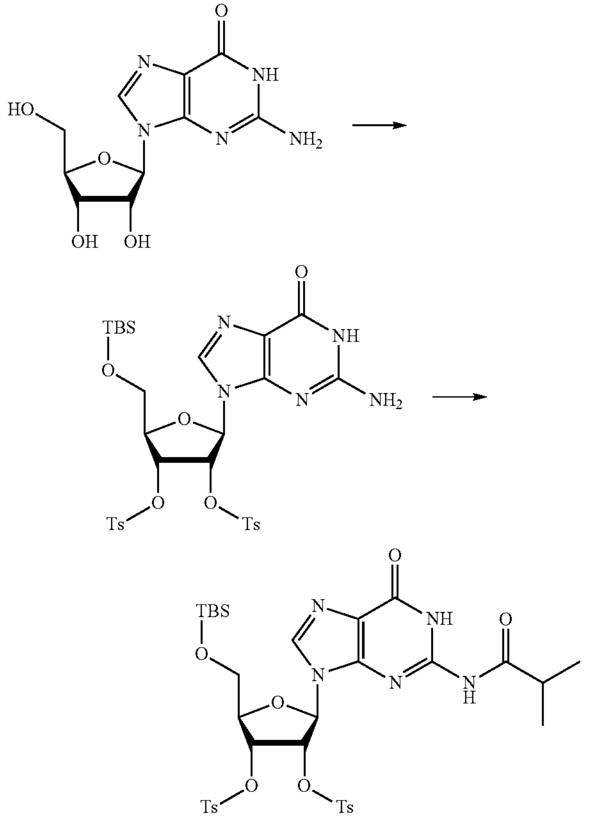

wherein the selectively functionalizing guanosine comprises:

(a) reacting guanosine with TBS-Cl in the presence of pyridine to form a product of step (a);

(b) reacting the product of step (a) with Ts-Cl and Ts-Cl in the presence of NMI to form a product of step (b); and (c) reacting the product of step (b) with isopropyl-COCl in the presence of pyridine to form a product of step (i);

(ii) reacting the product of step (i) with lithium isopropoxide, CPME, and AcOH to form a product of step (ii):

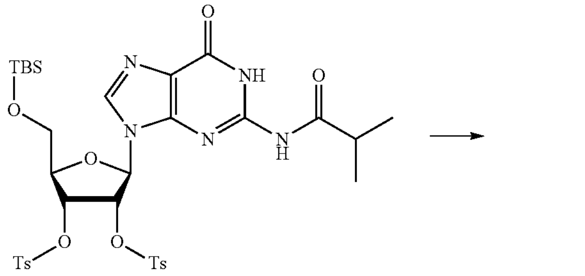

-continued

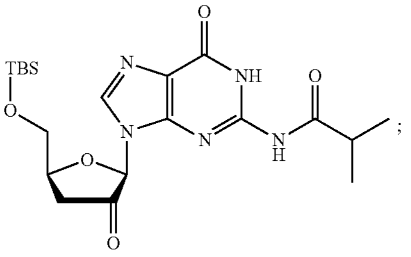

(iii) reacting the product of step (ii) with TFA to form a product of step (iii):

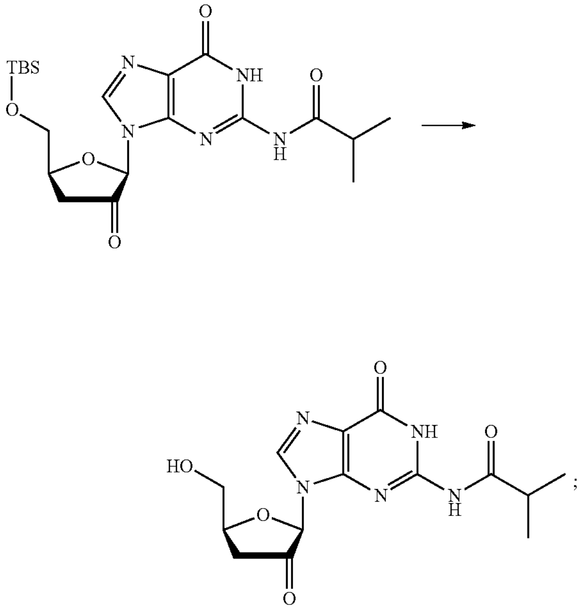

(iv) reacting the product of step (iii) with N-fluorobenzenesulfonimide in the presence of

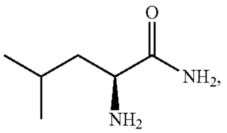

ammonium phosphate, and water, followed by TFA, to form a product of step (iv):

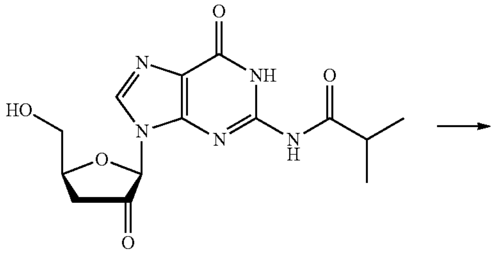

-continued

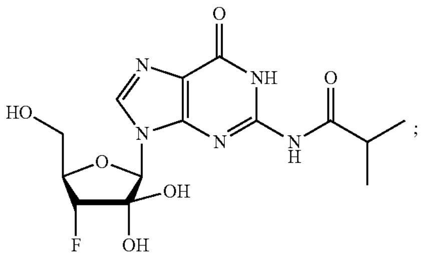

(v) reacting the product of step (iv) with an enzymatic reducing agent selected from ketoreductase enzymes having an amino acid sequence that is at least about 90% identical to the reference sequence of SEQ ID NO: 2, 3, 4, 5, 6, 7, 8, 9, 10, or 11, to form a product of step (v):

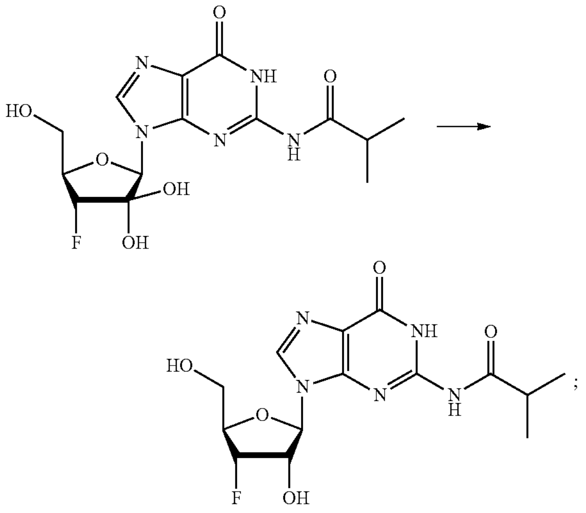

(vi) reacting the product of step (v) with $PSCl_3$ in the presence of quinine, 2,6-lutidine, and THF, followed by NaOH in the presence of MeOH and water:

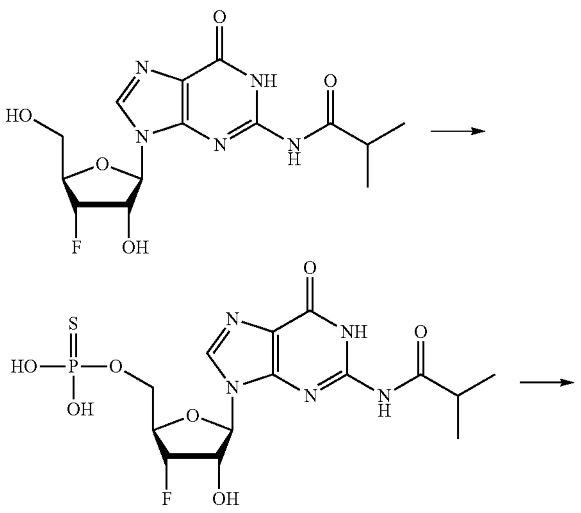

-continued

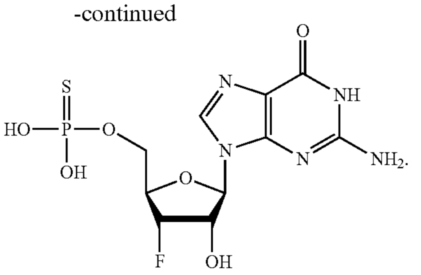

In aspects of the twelfth embodiment, the process further comprises forming a sodium or potassium salt of the compound of Formula (Ia).

In additional aspect, the process further comprises pretreating the ketoreductase enzymes with >20% isopropanol.

In aspects of the twelfth embodiment, the enzymatic reducing agent is selected from ketoreductase enzymes having an amino acid sequence that is at least about 90% identical to the reference sequence of SEQ ID NO: 2, 3, 4, 5, 6, 7, 8, 9, 10, or 11 and that have been pre-treated with isopropanol to a volume % of at least about 20% isopropanol, and then centrifuged to remove protein components that precipitate under such conditions. In specific aspects, the enzymatic reducing agent is selected from ketoreductase enzymes having an amino acid sequence that is at least about 90% identical to the reference sequence of SEQ ID NO: 2, 3, 4, 5, 6, 7, 8, 9, 10, or 11 and that have been pre-treated with isopropanol to a volume % of at least about 25% isopropanol and centrifuged to remove protein components that precipitate under such conditions. Specific aspects of the twelfth embodiment further comprise pre-treating the enzymatic reducing agent selected from ketoreductase enzymes having an amino acid sequence that is at least about 90% identical to the reference sequence of SEQ ID NO: 2, 3, 4, 5, 6, 7, 8, 9, 10, or 11 with isopropanol to a volume % of at least about 20% isopropanol; still further specific instances of such processes further comprise removing precipitated proteins from pretreated ketoreductase enzymes by centrifuge. Specific aspects of the twelfth embodiment further comprise pre-treating the enzymatic reducing agent selected from ketoreductase enzymes having an amino acid sequence that is at least about 90% identical to the reference sequence of SEQ ID NO: 2, 3, 4, 5, 6, 7, 8, 9, 10, or 11 with isopropanol to a volume % of at least about 25% isopropanol; still further specific instances of such processes further comprise removing precipitated proteins from pretreated ketoreductase enzymes by centrifuge.

In a thirteenth embodiment, the disclosure provides a process for the preparation of compounds of Formula (Ia), or a pharmaceutically acceptable salt, hydrate, or solvate thereof:

(Ia)

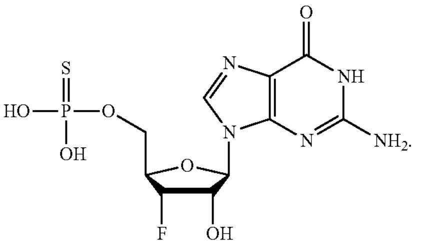

comprising (i) selectively functionalizing guanosine:

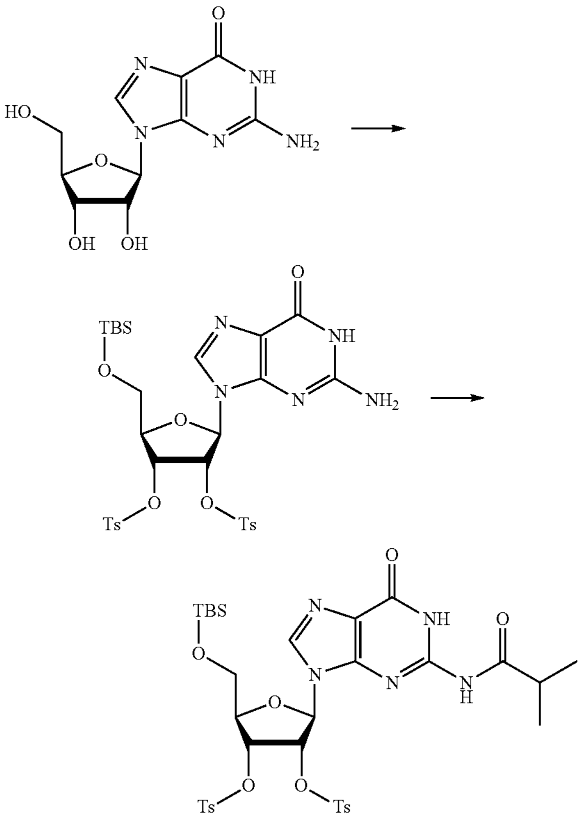

wherein the selectively functionalizing guanosine comprises:

(a) reacting guanosine with TBS-Cl in the presence of pyridine to form a product of step (a);

(b) reacting the product of step (a) with Ts-Cl and Ts-Cl in the presence of NMI to form a product of step (b); and (c) reacting the product of step (b) with isopropyl-COCl in the presence of pyridine to form a product of step (i);

(ii) reacting the product of step (i) with lithium isopropoxide, CPME, and AcOH to form a product of step (ii):

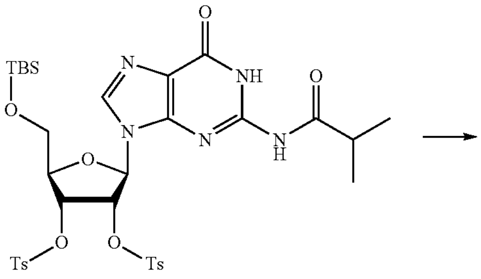

-continued

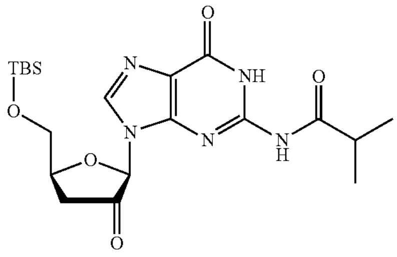

(iii) reacting the product of step (ii) with N-fluorobenzenesulfonimide in the presence of

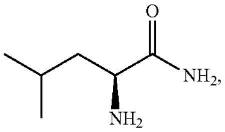

ammonium phosphate, and water, followed by TFA, to form a product of step (iii):

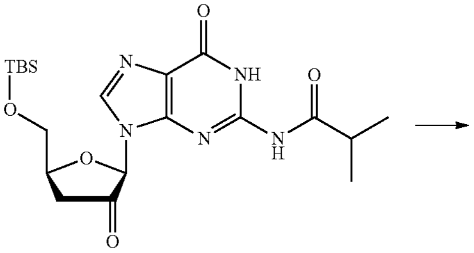

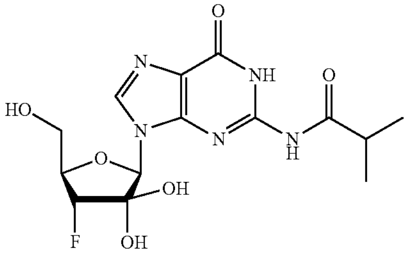

;

(iv) reacting the product of step (iii) with sodium triacetoxyborohydride to form a product of step (iv):

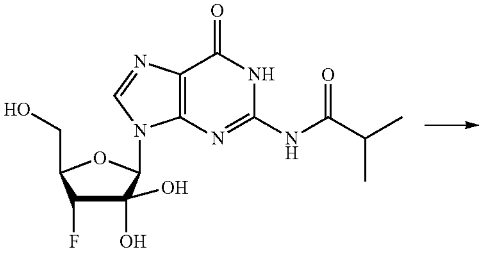

-continued

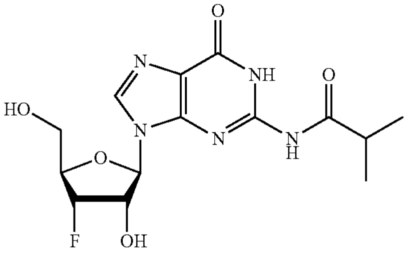

;

(v) reacting the product of step (iv) with $PSCl_3$ in the presence of quinine, 2,6-lutidine, and THF, followed by NaOH in the presence of MeOH and water, to form a product:

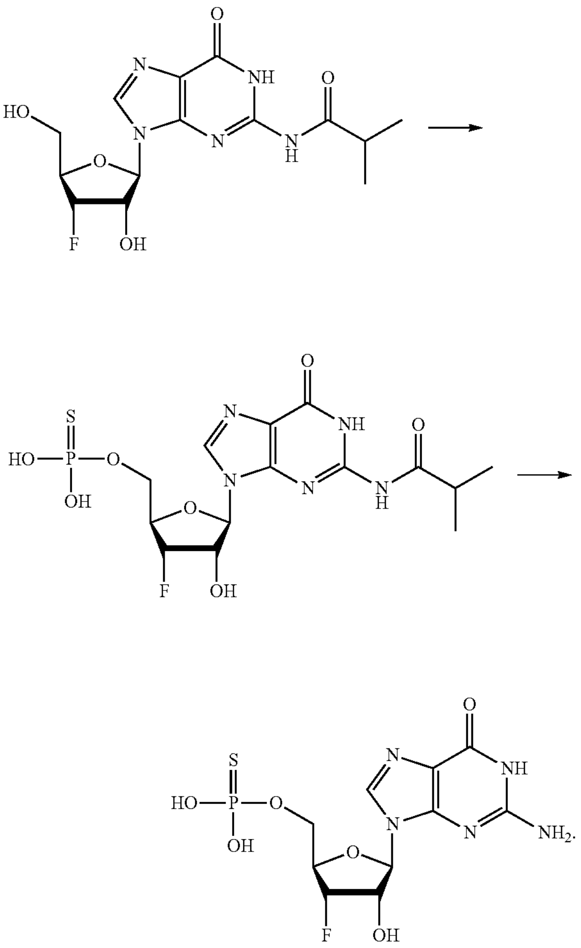

In aspects of the thirteenth embodiment, the process further comprises forming a sodium or potassium salt of the compound of Formula (Ia).

In a fourteenth embodiment, the disclosure provides a process for the preparation of compounds of Formula (Ia), or a pharmaceutically acceptable salt, hydrate, or solvate thereof:

(Ia)

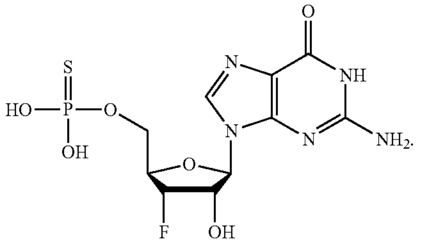

comprising (i) selectively functionalizing guanosine:

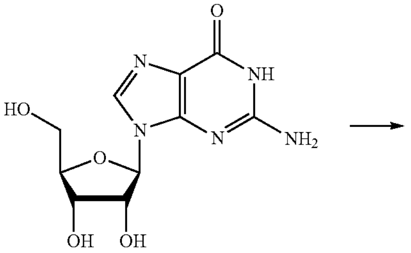

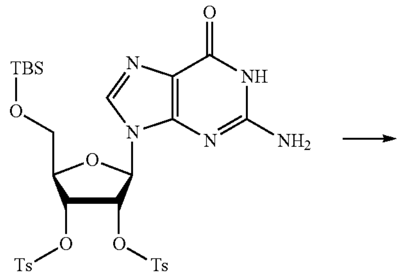

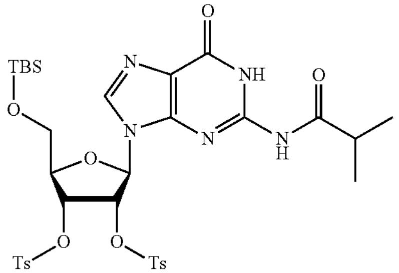

wherein the selectively functionalizing guanosine comprises:

(a) reacting guanosine with TBS-Cl in the presence of pyridine to form a product of step (a);

(b) reacting the product of step (a) with Ts-Cl and Ts-Cl in the presence of NMI to form a product of step (b); and (c) reacting the product of step (b) with isopropyl-COCl in the presence of pyridine to form a product of step (i);

(ii) reacting the product of step (i) with lithium isopropoxide, CPME, and AcOH to form a product of step (ii):

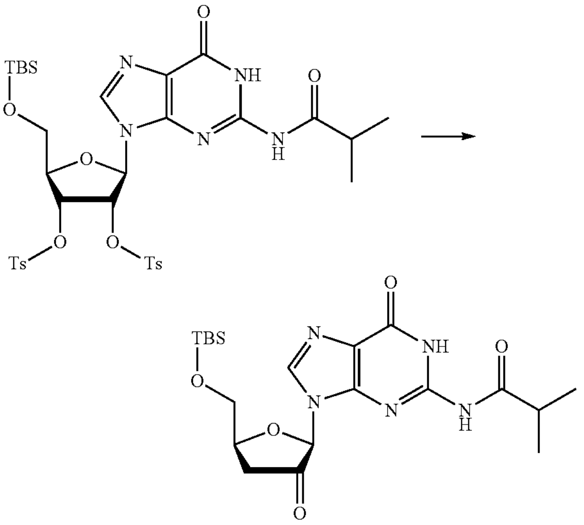

(iii) reacting the product of step (ii) with N-fluorobenzenesulfonimide in the presence of

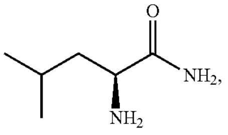

ammonium phosphate, and water, followed by TFA to form a product of step (iii):

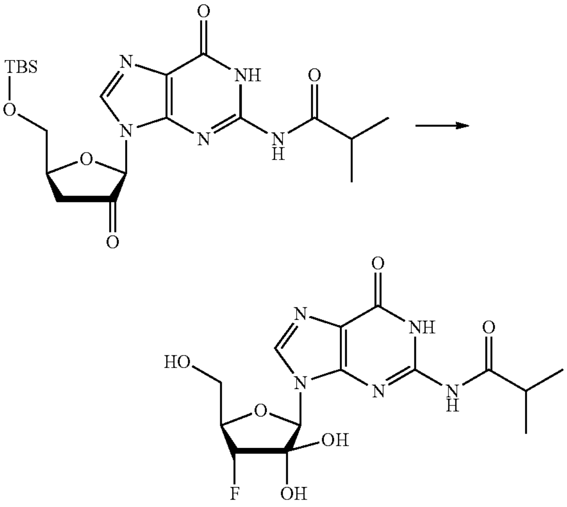

;

(iv) reacting the product of step (iii) with an enzymatic reducing agent selected from ketoreductase enzymes having an amino acid sequence that is at least about 90% identical to the reference sequence of SEQ ID NO: 2, 3, 4, 5, 6, 7, 8, 9, 10, or 11, to form a product of step (iv):

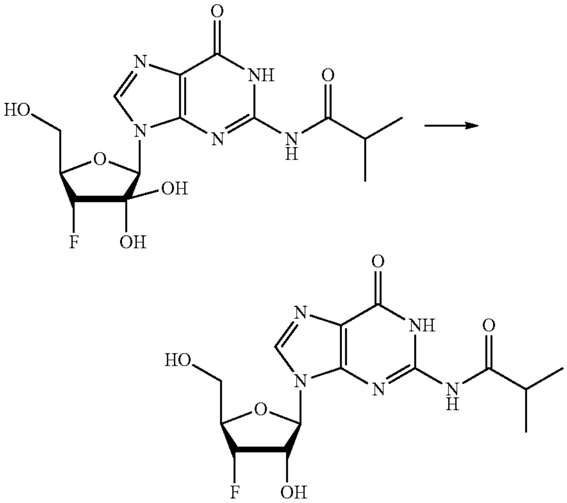

;

(v) reacting the product of step (iv) with $PSCl_3$ in the presence of quinine, 2,6-lutidine, and THF, followed by NaOH in the presence of MeOH and water:

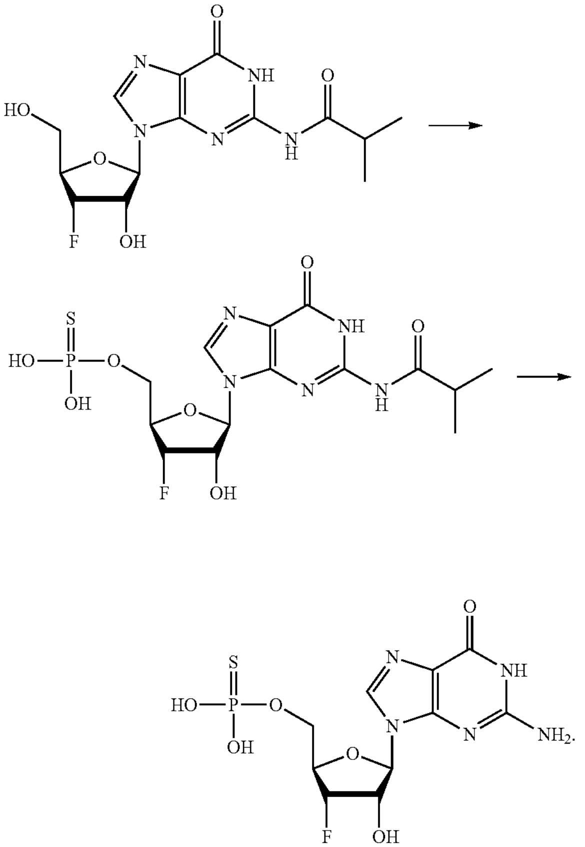

In aspects of the fourteenth embodiment, the process further comprises forming a sodium or potassium salt of the compound of Formula (Ia).

In additional aspect, the process optionally further comprises pre-treating the ketoreductase enzymes with >20% isopropanol.

The seventh through fourteenth embodiments are understood to include and incorporate the first through sixth embodiments in all their aspects.

In a fifteenth embodiment, the disclosure provides compounds selected from the group consisting of:

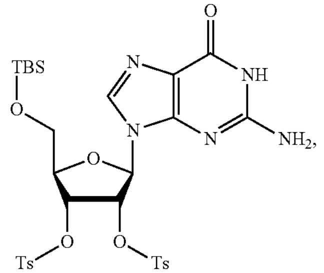

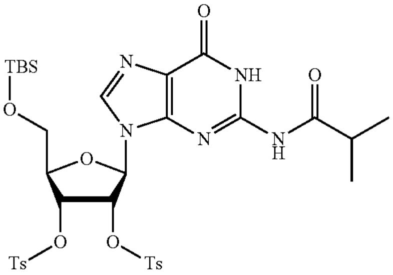

,

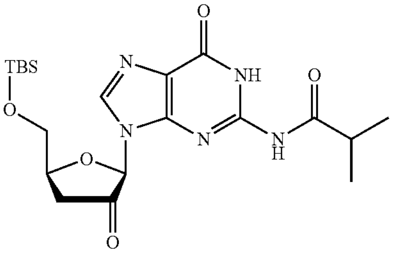

,

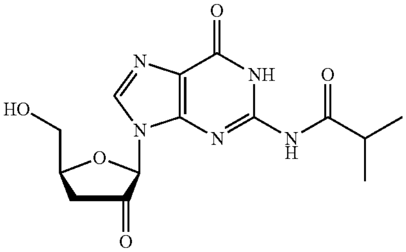

,

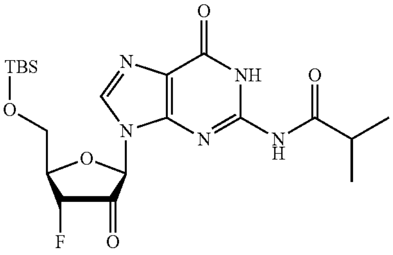

,

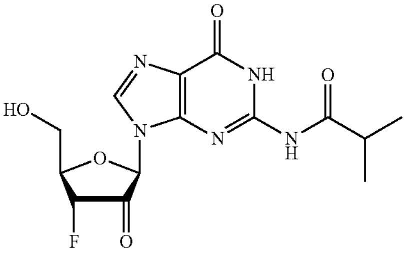

;

-continued

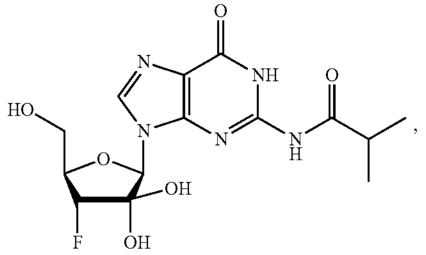

,

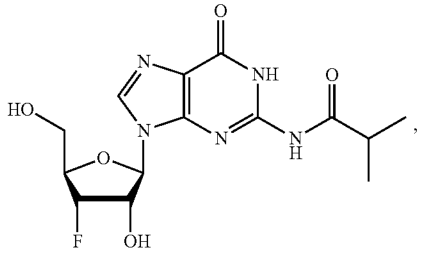

,

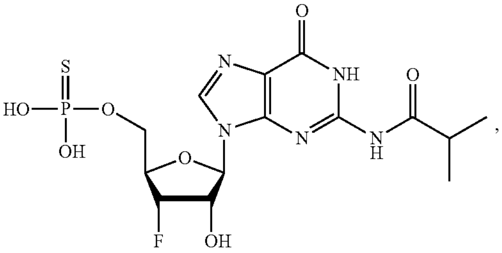

, and

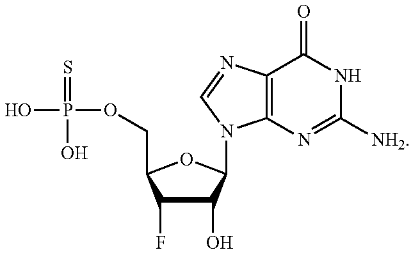

.

EXAMPLES

Example 1: Synthesis of (2R,3R,4R,5R)-2-(2-amino-6-oxo-1,6-dihydro-9H-purin-9-yl)-5-(((tert-butyldimethylsilyl)oxy)methyl)tetrahydrofuran-3,4-diyl bis(4-methylbenzenesulfonate)

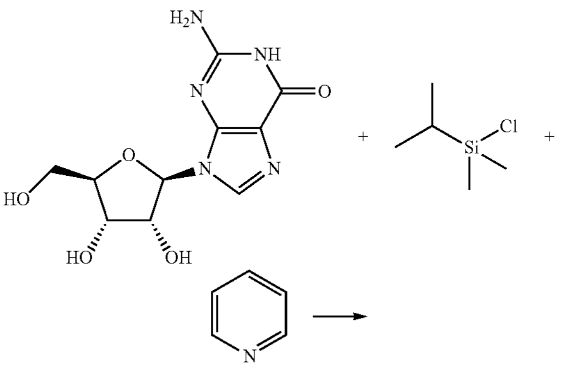

-continued

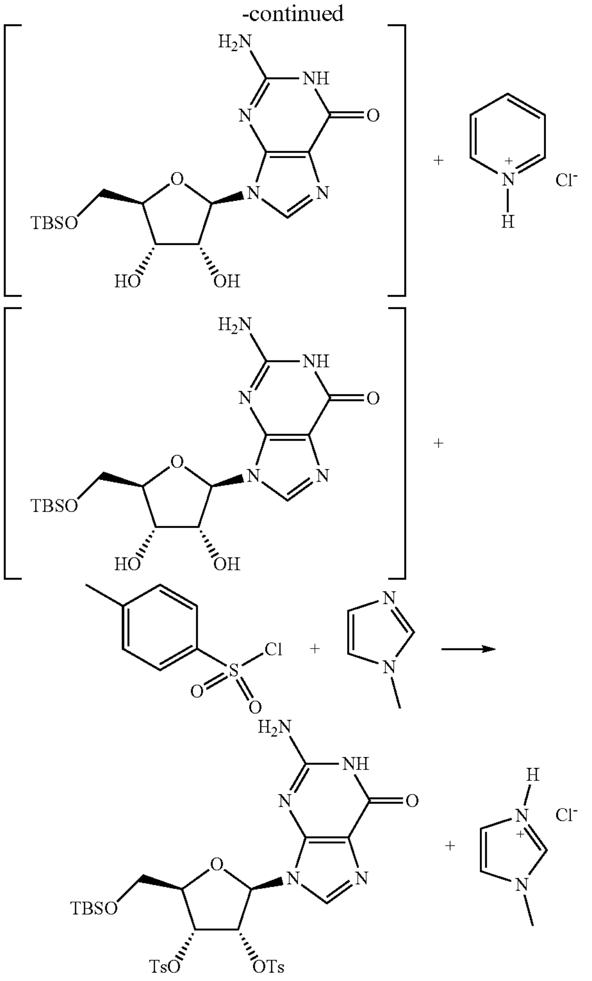

NMP (3.5 vol.) was added into a reaction vessel, and the temperature was adjusted to 48° C. to 52° C. Guanosine (800 g, 2824 mmol) was added. The reaction mixture was stirred for 30 min. to 1 h, and the temperature was adjusted to 8° C. to 12° C. TBS-Cl (575 g, 3815 mmol) (dissolved in 2 vol. NMP) was added into the reaction mixture (total NMP 5.5 vol.), and the reaction mixture was maintained at 8° C. to 12° C. Py (670 g, 8470 mmol) was added to the reaction mixture, which was maintained at 8° C. to 12° C. and stirred for 3 h to 4 h. The temperature was adjusted to −20° C. to −10° C. and stir for 8 h to 15 h, after which the temperature was adjusted to −5° C. to 5° C.

NMI (2319 g, 28240 mmol) was added to the reaction mixture, which was kept at −5° C. to 5° C. To the reaction mixture, 2.1 eq. Ts-Cl (1131 g dissolved in 3 vol. 2-Me-THF) was added, and the reaction mixture was stirred at −5° C. to 5° C. for 4 h to 8 h. Then, 0.7 eq. Ts-Cl (377 g, dissolved in 1 vol. 2-Me-THF) was added. The reaction mixture was stirred for 12 h to 14 h at −5° C. to 5° C. TsCl (0.16 eq, 86 g dissolved in 160 mL 2-Me-THF) was added to the reaction mixture, which was stirred for 3 h to 5 h. 5.5 vol. MeOH was added to the reaction mixture at 15° C. to 25° C., followed by 8 vol. water. The reaction mixture was stirred at this temperature for 12 h to 15 h. The reaction mixture was then filtered and rinsed with 2 vol. MeOH/water (1:3). The reaction product was dried under 45° C. for 70 h in two parts.

Example 2: Synthesis of (2R,3R,4R,5R)-2-(((tert-butyldimethylsilyl)oxy)methyl)-5-(2-isobutyramido-6-oxo-1,6-dihydro-9H-purin-9-yl)tetrahydrofuran-3,4-diyl bis(4-methylbenzenesulfonate)

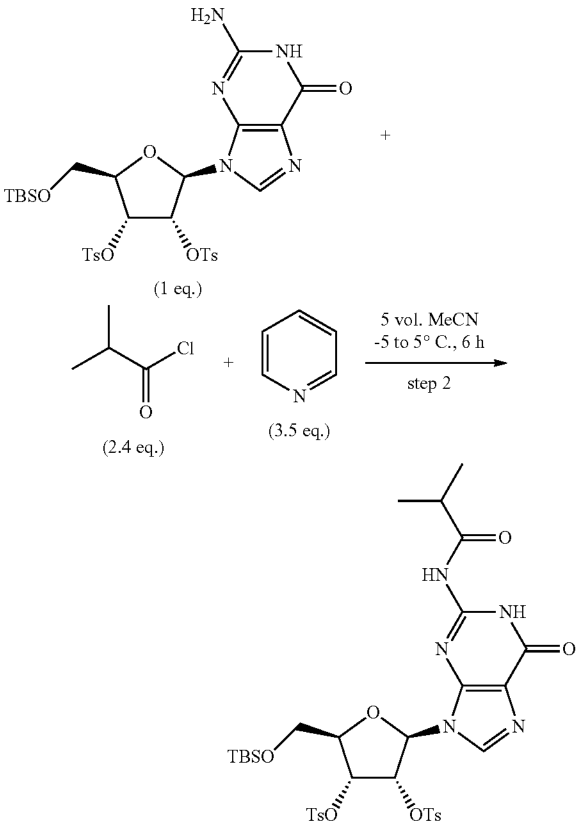

The bis-tosylate (1096.00 g (1185.50 g×92.45%)) was charged into a reaction vessel. MeCN (3.3 L, 3 vol.) and Py (510.52 g, 4.2 eq.) then were charged into the reaction vessel. The reaction mixture was cooled to −15° C. to −5° C. (slurry). Isobutyryl chloride (397.51 g, 2.4 eq.) was added by dropwise to the reaction mixture under −5° C. (slurry). The reaction mixture was stirred at −15° C. to −5° C. for 18 h. Isopropyl acetate (6 L, 5 vol.) was charged into the reaction mixture, and 15% $K_2CO_3$ liquor (6 kg) was added by dropwise into the reaction mixture under −5° C. The reaction mixture was stirred at −15° C. to −5° C. for 30 min. The reaction mixture was then warmed to 20° C. to 30° C. and stirred for 10 min to 30 min.

The reaction mixture was separated, and the aqueous layer was removed. The organic layer was concentrated to 3-4 vol. at 30° C. IPAc (6 L, 5-6 vol.) was charged into the concentrated organic layer, which was then stirred at 25° C. to 30° C. for 30 min. The organic layer was then further concentrated until it reached 5-6 vol. under 30° C. An additional IPAc (2 L, 2-3 vol.) was charged into the concentrated organic layer, and it was stirred at 25° C. to 30° C. for 30 min. The reaction mixture was cooled to 15° C. to 25° C. 3 L (3 vol.) n-heptane was added drop-wise at 15° C. to 25° C. for 6 h, then the reaction mixture was stirred for 10 h at 25° C. to 30° C. 3 L n-heptane was added drop-wise at 15° C. to 25° C. for 6 h, and the reaction mixture was stirred at 25° C. to 30° C. for 10 h. The suspension was filtered, and the filter cake was washed with 2 L mixture solution (IPAc/n-heptane=1 L/1 L) to give the product, which was dried in oven under 35° C. by reduce for 24 h.

$^1$H NMR (500 MHz, DMSO-d6) δ 11.97 (s, 1H), 11.50 (s, 1H), 7.89 (d, J=8.3 Hz, 2H), 7.86 (s, 1H), 7.55 (d, J=8.2 Hz, 2H), 7.38 (d, J=8.2 Hz, 2H), 7.07 (d, J=8.2 Hz, 2H), 6.00 (d, J=7.9 Hz, 1H), 5.58 (dd, J=7.8, 5.4 Hz, 1H), 5.05 (d, J=5.3 Hz, 1H), 4.27 (t, J=4.5 Hz, 1H), 3.85 (dd, J=12.2, 4.1 Hz, 1H), 3.70-3.66 (m, 1H), 2.76 (septet, J=6.8 Hz, 1H), 2.46 (s, 3H), 2.26 (s, 3H), 1.18 (t, J=7.2 Hz, 6H), 0.87 (s, 9H), 0.06 (s, 3H), 0.04 (s, 3H).

$^{13}$C NMR (125 MHz, DMSO-d6) δ 180.4, 154.8, 148.5, 148.3, 146.3, 146.0, 137.1, 132.6, 131.6, 131.0, 130.0, 128.3, 127.3, 120.59, 83.9, 83.4, 78.5, 76.8, 62.7, 35.4, 31.7, 28.8, 26.2, 21.7, 21.4, 19.4, 19.2, 18.4, 14.4, −5.1, −5.1.

Example 3: Ketone Synthesis

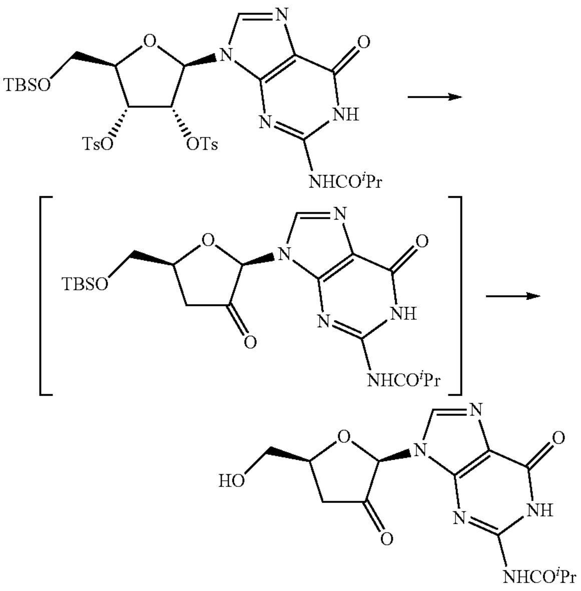

A first reaction vessel was charged with IPA (3.88 L, 50.30 mol) and THF (9.75 L, 1.5 vol) at RT and placed under $N_2$ before being cooled to −15° C. n-Butyllithium (19.18 L, 47.90 mol, 2.5M in hexanes) was then added slowly, maintaining internal temperature below 25° C. A second vessel was placed under $N_2$ and charged with the bis-tosylate (6.5 kg, 7.99 mol, 96 wt %) and CPME (26 L, 4 vol) before being cooled to −5° C. The solution of lithium isopropoxide from the first reaction vessel was then vacuum transferred to the slurry in the second reaction vessel, and the mixture was warmed to 0° C. and aged for about 18 h. The slurry was cooled to −10° C., and AcOH (2.74 L, 47.90 mol) was added slowly, maintaining internal temperature below 5° C. To this mixture was added DI water (32.5 L, 5 vol), the phases were separated, and the aqueous phase was removed from reactor. The organic layer was cooled to −10° C., and TFA (3.08 L, 40.00 mol) was added slowly, maintaining the internal temperature below 5° C., followed by trioctylamine (6.99 L, 15.98 mol). The mixture was warmed to 0° C. and aged for about 16 h. The slurry was cooled to −10° C. and trioctylamine (10.48 L, 23.97 mol) was added slowly. The resulting homogenous solution was warmed to 25° C. and seeded with 1 wt % of the ketone (26.7 g, 0.0799 mol) and aged for 18 h. The slurry was filtered, and the cake was completely deliquored. The cake was then slurry washed twice with CPME (3.25 L, 0.5 vol) and then dried under vacuum with $N_2$ sweep.

$^1$H NMR (500 MHz, DMSO-d6) δ 12.12 (s, 1H), 11.47 (s, 1H), 8.11 (s, 1H), 5.99 (s, 1H), 5.05 (t, J=5.6 Hz, 1H), 4.54 (app. dq, J=8.6, 5.4, 4.4 Hz, 1H), 3.71-3.60 (m, 2H), 2.97 (dd, J=18.5, 8.4 Hz, 1H), 2.85-2.75 (m, 2H), 1.14 (app. d, J=6.8 Hz, 6H).

$^{13}$C NMR (125 MHz, DMSO-d6) δ 209.0, 180.6, 155.2, 149.0, 148.6, 139.4, 120.4, 81.7, 77.1, 63.8, 38.0, 35.3, 19.4, 19.3.

Example 4: Ketone Fluorination

NFSI (1.964 kg in 5.5 L THF) was charged into a first reaction vessel. The ketone (1.832 kg) was then charged into a separate reaction vessel, followed by THF (5.5 L), $H_2O$ (0.932 L) and L-leucine amide hydrochloride (259 g). The reaction mixture in the second reaction vessel was agitated at 70 rpm at RT. After 40 min., the reaction temperature was 20° C., and 1.5 L NFSI solution (~20%) from the first reaction vessel was added to the second reaction vessel, followed immediately by 1.371 kg $(NH_4)_2HPO_4$. The agitation was set 80 rpm. After 20 min., the remainder of the NFSI from the first reaction vessel was charged into the second reaction vessel over 90 min., and the reaction mixture was left for 2 h at 27° C. THF (200 mL) was added to rinse the bottle, and the mixture became homogenous as the temperature increased to 27.9° C. The agitation was then set to 92 rpm. The reaction mixture was then aged for 42 h.

While the temperature was maintained at 27° C., $H_2O$ (10 vol, 18.32 L) was charged into the reaction mixture over 40 min. The reaction mixture was concentrated by distillation, removing THF in batches. Once the distillation was completed, the slurry was allowed to de-supersaturate at 22° C. overnight.

The reaction mixture was set to agitate at 47 rpm. The reaction mixture was filtered under vacuum. The wet cake was then washed with 11 L $H_2O$, followed by MeCN (2×5.5 L). The wet cake was then dried under $N_2$ sweep for a period of two and a half days.

$^1$H NMR (500 MHz, DMSO-$d_6$: $D_2O$ (5:1)) δ 12.08 (s, 1H), 11.69 (s, 1H), 8.02 (s, 1H), 7.00 (br s, 2H), 5.85 (d, J=1.9 Hz, 1H), 5.15 (br s, 1H), 4.83 (dd, J=53.6, 2.7 Hz, 1H), 4.06 (dddd, J=26.2, 8.3, 2.9, 2.8 Hz, 1H), 3.70-3.63 (m, 2H), 2.77 (sept, J=6.8 Hz, 1H), 1.12 (d, J=6.7 Hz, 6H).

$^{13}$C NMR (126 MHz, DMSO-$d_6$: $D_2O$ (5:1)) δ 180.7, 155.6, 149.6, 148.3, 139.7, 119.5, 97.2 (d, J=17.8 Hz), 93.4 (d, J=188.7 Hz), 86.1, 81.8 (d, J=23.2 Hz), 60.8 (d, J=7.6 Hz), 35.3, 19.2, 19.1.

$^{19}$F NMR (470 MHz, DMSO-$d_6$: $D_2O$ (5:1)) 6-189.1 (dd, J=53.6, 26.1 Hz).

Example 5: Chemical Ketone Reduction to 3'-FG

A first reaction vessel was charged with HOAc (2.8 L, 2.0 vol) and MeCN (4.2 L, 3.0 vol) followed by STAB (2.30 kg, 3.0 eq). The walls of the first reaction vessel were rinsed with MeCN (2.8 L, 2.0 vol). The resulting solution had an internal temperature of 14° C. and was heated to 22° C. over 1 h. The resulting solution was then stirred for 3 h at RT.

A second reaction vessel was charged with HOAc (4.2 L, 3 vol.) and MeCN (6.3 L, 4.5 vol.) followed by the fluorinated ketone (1.40 kg, 3.0 eq.). The vessel walls were rinsed with MeCN (2.1 L, 1.5 vol). The resulting slurry was heated to 35° C. over 40 min. The solution of STAB from the first reaction vessel was added to the slurry over approximately 2 h. The resulting slurry was stirred for 2 h at 35° C. to 40° C., before the slurry was cooled to 25° C. over 30 min. MeOH (2.8 L, 2 vol.) was added over 1 h, and the resulting solution was allowed to stir for 13.5 h at RT.

The reaction vessel was placed under vacuum for distillation, and the temperature was set to 50° C., with distillation starting when the internal temperature reached to 35° C. Distillation was continued until total~4 vol. (5.6 L) of the reaction mixture remained. DI water (2.8 L) was added over 6 min when internal temperature reached 55° C. The walls were washed with water. $(NH_4)_2SO_4$ (2.8 L, 2 vol.) was added over 20 min to the washed reaction solution.

The reaction mixture was seeded with 10 g and aged for 40 min. Following aging, $(NH_4)_2SO_4$ (22.4 L, 16 vol.) was added over 4 h, and the slurry was aged again for 2 h at 55° C. The reaction mixture was cooled to RT over 5 h, and then aged at RT for 5.5 h.

After aging, the reaction mixture was filtered, and the filter cake was washed with 4.3 L of $H_2O$:MeOH (3:1) twice. The cake was then dried under $N_2$ sweep and vacuum.

$^1$H NMR (500M Hz, DMSO-$d_6$) δ 11.68 (s, 2H), 8.27 (s, 1H), 5.96 (d, J=5.4 Hz, 1H), 5.83 (d, J=8.1 Hz, 1H), 5.22 (t, J=5.4 Hz, 1H), 5.07 (dd, J=54.3, 4.1 Hz, 1H), 4.77 (dddd, 27.3, 8.1, 4.1, 4.1 Hz, 1H), 4.25 (dddd, J=27.2, 8.1, 4.1 Hz, 4.1 Hz, 1H), 3.61 (m, 2H), 2.75 (sept, J=6.8 Hz, 1H), 1.12 (d, J=6.8 Hz, 6H).

$^{13}$C NMR (125 MHz, DMSO-$d_6$) δ 180.2, 154.8, 149.3, 148.4, 137.4, 120.1, 92.8 (d, J=183 Hz), 85.0, 83.6 (d, J=21.1 Hz), 83.5, 72.6 (d, J=16.1 Hz), 60.6 (d, J=11.2 Hz), 34.8, 18.8, 18.8.

$^{19}$F NMR (500 MHz, DMSO-$d_6$) δ −197.5.

Example 6: Biocatalytic Ketone Reduction to 3'-FG (Alternative to Chemical Ketone Reduction)

10 uL of a ketoreductase enzyme that can be represented by amino acid sequence as set forth above in SEQ ID NO. 6 was inoculated into 5 mL of Luria-Bretani Broth (culture media for cells), supplemented with 1% glucose and 50 ug/ml of Kanamycin antibiotic and grown overnight for 20 h to 24 h at 30° C., 250 rpm, in a shaking incubator.

5 mL of the overnight culture was used to subculture 250 mL of Terrific Broth growth media (commercially available from ThermoFisher Scientific as Catalog #A1374301) in a 1 L flask. The subculture was allowed to grow at 30° C. for 3 h at 250 rpm, in a shaking incubator. When the OD measures between 0.4 and 0.6, the IPTG was introduced to an IPTG final concentration of 1 mM. The subculture was allowed to grow overnight, for 18 h to 20 h.

After the growth period, the culture was transferred to a centrifuge bottle and centrifuged for 20 min. at 4000 rpm at 4° C. Following centrifuge, the supernatant was discarded. The cell pellets were resuspended in 50 mM sodium phosphate buffer (pH=7).

The cells from the resuspended cell pellets were lysed using a microfluidizer, and the cell lysate was collected and centrifuged for 60 min. at 10000 rpm at 4° C. The cell lysate was centrifuged, and the supernatant (the "clarified cell lysate") was transferred to a petri dish and frozen at −80° C. for a minimum of 2 h. Frozen samples were then lyophilized using a standard automated protocol.

In instances in which ketoreductase enzymes with improved purity was desired, the clarified cell lysate was pre-treated with isopropanol to bring the volume % of isopropanol to 25%. The isopropanol treated lysate was incubated for between 1 h and overnight at room temperature. The isopropanol-treated lysate was centrifuged, and the pellet was removed. The supernatant was transferred to a petri dish and frozen at −80° C. for a minimum of 2 h. Samples were lyophilized using a standard automated protocol.

20 mg of a commercially available ketoreductase enzyme (KRED-P1 B10, available from CODEXIS) added to a reaction vessel, along with NADPH (20 mg), a ketoreductase enzyme that can be represented by amino acid sequence as set forth above in SEQ ID NO. 6 (250 mg, harvested from the subculture), and fluoroketone (250 mg, Example 4 above). 10 mL of phosphate buffer (0.1M, pH=6.0) and 1 mL IPA were added to the reaction vessel. The temperature was set at 30° C., and the reaction mixture was stirred at 350 rpm. After 20 h, the mixture was cooled to 15° C. NaCl (2 g) was added to the reaction vessel, and the reaction mixture was allowed to de-supersaturate overnight. The solids were filtered and washed with 2.5 mL (10 vol) of water. The wet cake was placed into a 50° C. vacuum oven to dry overnight.

Example 7: Thiophosphorylation

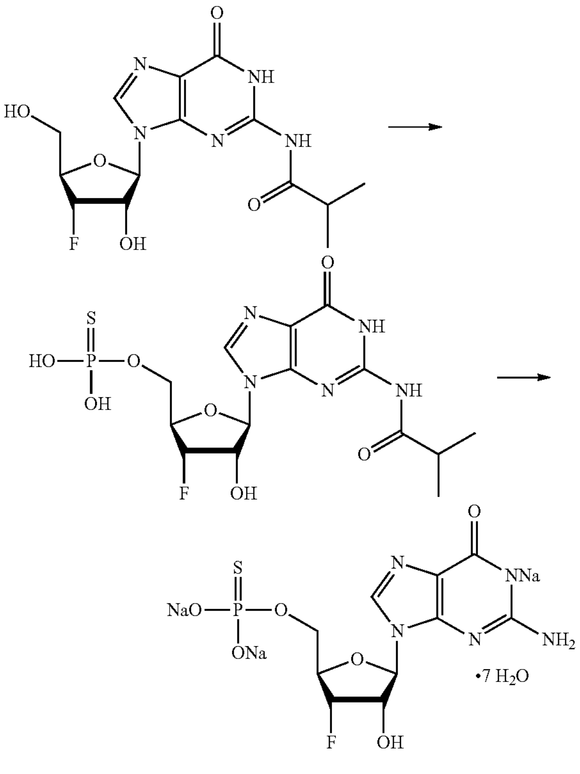

A reaction vessel at 22° C. was charged with THF (16 L). Quinine (234 g, 0.72 mol, 0.25 equiv) was charged into the reaction vessel, followed by 2,6-lutidine (463 g, 4.32 mol, 1.5 equiv), and 3'-FG (1100 g, 2.88 mol, 1.0 equiv, Example 6 above). THF (6 L) was used to rinse the sides of the reaction vessel, and the temperature was set to 0° C. $PSCl_3$ (658 g, 3.89 mol, 1.35 equiv) was charged, maintaining the temperature below 2° C. The reaction mixture was stirred at 80 rpm for approximately 40 h at 0° C. The reaction progress was monitored by UPLC analysis; once 96% conversion had been obtained, the reaction temperature was adjusted to −10° C. $H_2O$ (2.2 L) was added dropwise, maintaining the temperature below 0° C. After the addition, the temperature was adjusted to 25° C., and the reaction mixture was held at this temperature for 1 h.

The THF was removed in vacuo. After THF removal (at least 17 vol.), the vacuum was broken, and the temperature was set to 25° C. MeOH (11 L) was charged into the reaction vessel, and the temperature was adjusted to −10° C. Aqueous NaOH (50 wt %) was diluted with $H_2O$ (1.1 L) and charged into the reaction vessel, maintaining the temperature below 25° C.

The temperature was then adjusted to 45° C., and, after 90 min, the reaction mixture was seeded with 3'-F-thio-GMP (1 wt %, 11 g). The mixture was held at 45° C. for 5 h, then cooled to 20° C. over 5 h, and held at 20° C. THF (1.8 L, 1.6 V) added over 45 min at 20° C., and the mixture was agitated for 3 h. The mixture was then filtered, and the wet cake was washed with 10:4:2 MeOH:THF:$H_2O$ (10 L). The cake was then washed with THF (10 L), and the cake was dried under vacuum under a sweep of humidified $N_2$.

$^{1}$H NMR (500 MHz, $D_2O$): δ 8.17 (s, 1H), 5.94 (d, J=8.4 Hz, 1H), 5.30 (dd, J=54.2, 4.3 Hz, 1H), 4.93 (ddd, J=25.9, 8.4, 4.3 Hz, 1H), 4.63-4.54 (m, 1H), 4.08-4.00 (m, 1H), 3.97-3.89 (m, 1H).

$^{13}$C NMR (126 MHz, $D_2O$): 167.7, 161.0, 152.15, 135.93, 117.4[1], 92.53-93.96 (d), 84.68, 82.95 (m), 73.25 (m), 63.50 (m).

$^{19}$F NMR (470 MHz, $D_2O$) δ −197.9.

$^{31}$P NMR (203 MHz, $D_2O$) δ 43.31.

It will be appreciated that various of the above-discussed and other features and functions, or alternatives thereof, may be desirably combined into many other different systems or applications. It will also be appreciated that various presently unforeseen or unanticipated alternatives, modifications, variations, or improvements therein may be subsequently made by those skilled in the art, and these are also intended to be encompassed by the following claims.

What is claimed is:

1. A process for preparing a compound of Formula (I), or a pharmaceutically acceptable salt, hydrate, or solvate thereof:

(I)

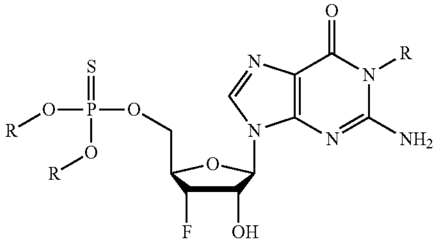

wherein each R is independently selected from the group consisting of H, Na, and K, comprising reacting a compound of Formula (I-2) with at least one Reducing Agent to provide a compound of Formula (I-1):

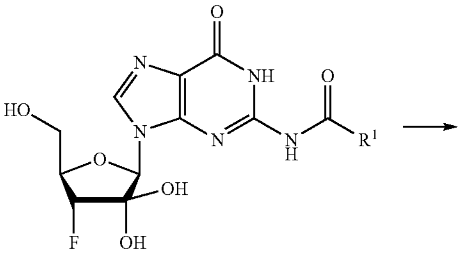

(I-2)

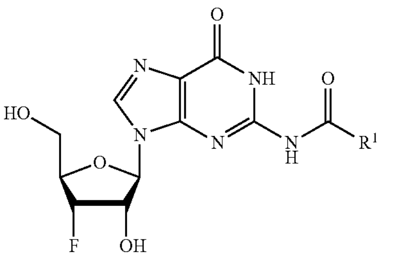

(I-1)

reacting the compound of Formula (I-1) with a thiophosphorylating agent in the presence of at least one Catalyst A and at least one Base A in the presence of at least one Solvent A, to form a compound of Formula (I-1') and then reacting the compound of Formula (I-1') with at least one Base B in the presence of at least one Solvent B:

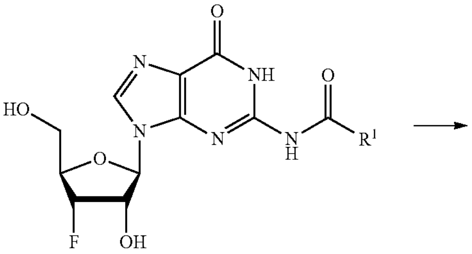

(I-1)

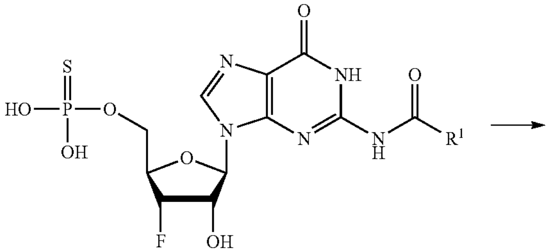

(I-1')

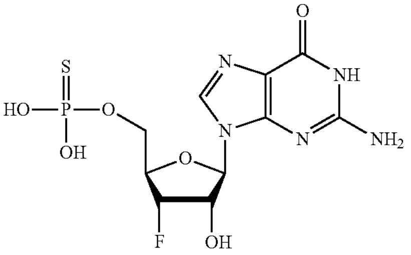

(I)

wherein each $R^1$ is selected from the group consisting of $C_1$-$C_{12}$ alkyl, benzyl, aryl, and heteroaryl, wherein the at least one thiophosphorylating agent is thiophosphoryl chloride; and the at least one Catalyst A is selected from the group consisting of

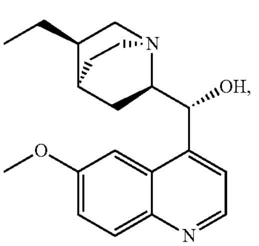

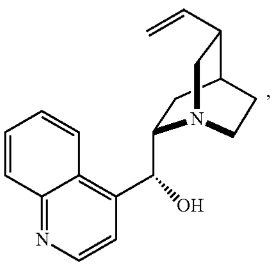

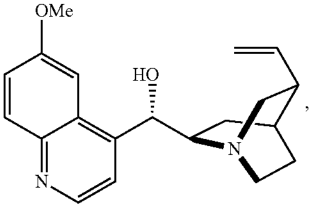

-continued

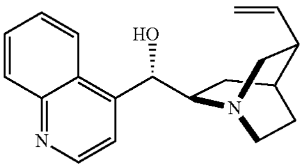
,

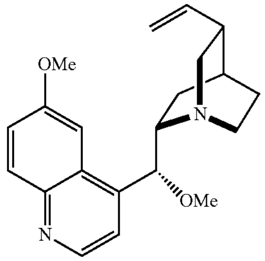
,

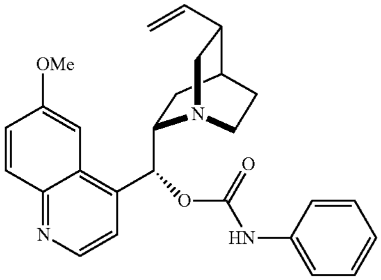
,

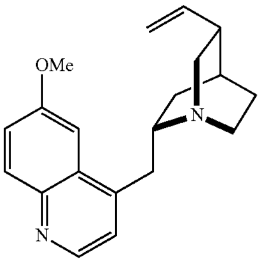
,
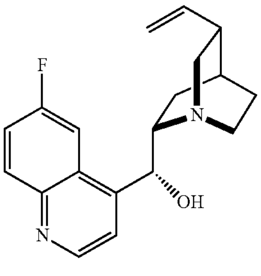
,

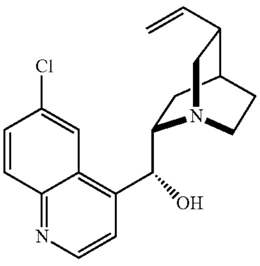
,
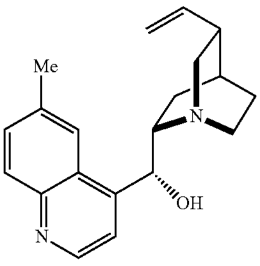
,

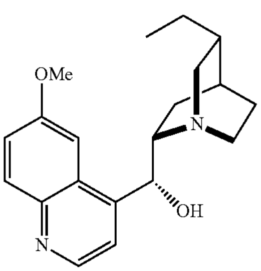
,
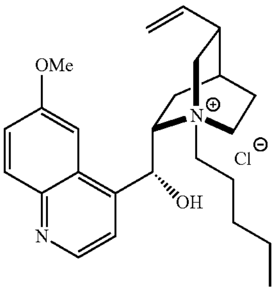
,

-continued

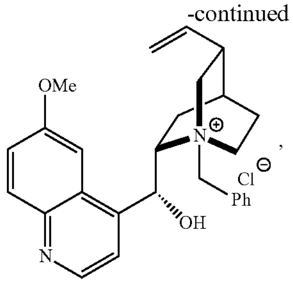
,
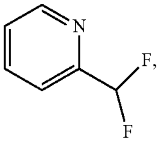

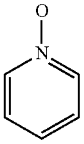
,
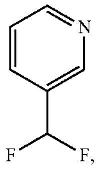
,
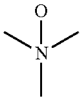
,
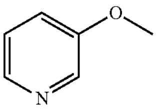
,

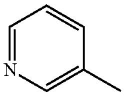
,
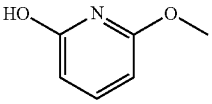
,
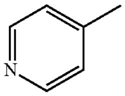
,

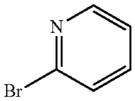
,
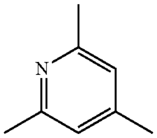
, and
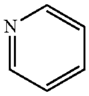
.

2. The process according to claim 1, wherein the compound of Formula (I) is a compound of Formula (Ia), or a pharmaceutically acceptable salt, hydrate, or solvate thereof:

(Ia)

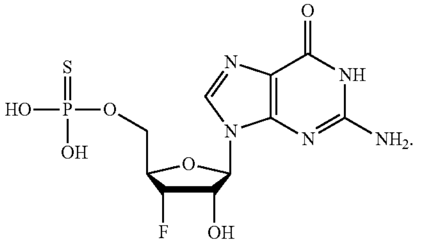

3. The process according to claim 1, wherein the at least one Base A is selected from the group consisting of 2,6-lutidine, pyridine, $Et_3N$, 1,8-bis(dimethylamino) naphthalene, 2,6-lutidine, 2,4-lutidine, 2-methyl-pyridine, trimethylpyridine, 3-methoxy-pyridine, 4-methyl-pyridine, quinuclidine, Hunig's base, 3-methyl-pyridine, and 2,6-di-tert-butyl-4-methyl pyridine, and mixtures thereof.

4. The process according to claim 1, wherein the at least one Solvent A is selected from the group consisting of THE, MeCN, acetone, DMPU, HFIP, TFE, DME, DMAC, 2-Me-THF, EtOAc, and MIBK, and mixtures thereof.

5. The process according to claim 1, wherein the reacting to form the compound of Formula (I-1') is conducted at a temperature in a range of from about −40° C. to about 40° C.

6. The process according to claim 1, wherein the at least one Base B is selected from the group consisting of NaOH, KOH, $NH_4OH$, and $MeNH_2$, and mixtures thereof.

7. The process according to claim 1, wherein the at least one Solvent B is selected from the group consisting of MeOH, IPA, and EtOH, and mixtures thereof.

8. The process according to claim 1, further comprising isolating the compound of Formula (I) by crystallization from at least one Solvent C selected from the group of IPA, THE, EtOH, and MeCN, and mixtures thereof.

9. The process according to claim 1, wherein the at least one Reducing Agent is at least one chemical reducing agent selected from the group consisting of sodium triacetoxy borohydride, sodium cyanoborohydride, sodium borohydride, sodium tris(trifluoroacetoxy) borohydride, tetramethylammonium triacetoxyborohydride, sodium tri (2-methylacetoxy) borohydride, sodium tri (2-phenylacetoxy) borohydride, and mixtures thereof.

10. The process according to claim 1, wherein the at least one Reducing Agent is selected from the group consisting of enzymatic reducing agents.

11. The process according to claim 10, wherein the at least one Reducing Agent is selected from the group consisting of ketoreductase enzymes.

12. The process according to claim 10, wherein the at least one Reducing Agent is selected from the group consisting of ketoreductase enzymes having an amino acid sequence that is at least about 90% identical to the reference sequence of SEQ ID NO: 2, 3, 4, 5, 6, 7, 8, 9, 10, or 11.

13. The process according to claim 11, further comprising pre-treating the ketoreductase enzymes with >20% isopropanol.

14. The process according to claim 1, further comprising reacting a compound of Formula (I-3) with at least one Fluorinating Agent A in the presence of at least one Catalyst B, at least one Base C, and water to provide the compound of Formula (I-2):

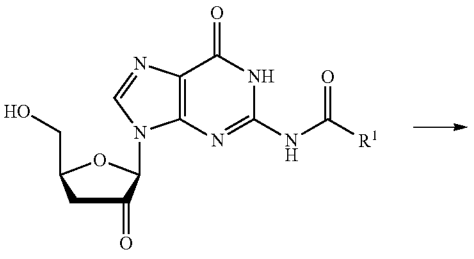

(I-3)

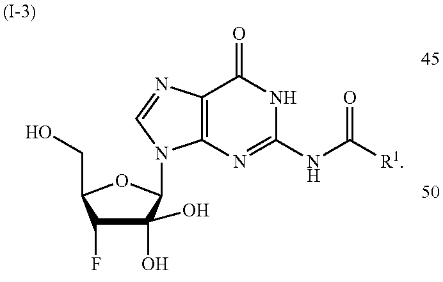

(I-2)

15. The process according to claim 14, wherein the at least one Fluorinating Agent A is selected from the group consisting of N-fluorobenzenesulfonimide, 1-chloromethyl-4-fluoro-1,4-diazoniabicyclo[2.2.2] octane bis(tetrafluoroborate), 1-fluoro-4-methyl-1,4-diazoniabicyclo[2.2.2] octanebis(tetrafluoroborate), N-fluoropyridinium triflate, and N-fluoropyridinium tetrafluoroborate, and mixtures thereof.

16. The process according to claim 14, wherein the at least one Catalyst B is selected from the group consisting of ($C_1$-$C_8$ alkyl) $NH_2$,

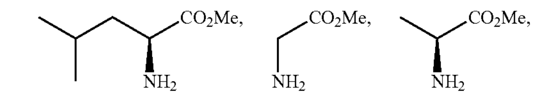

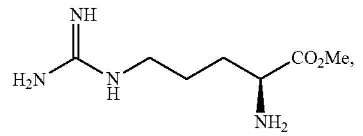

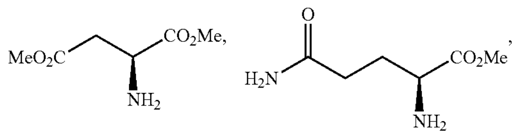

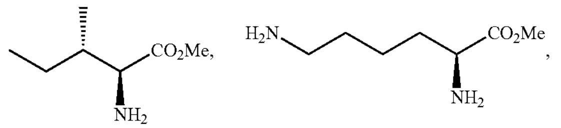

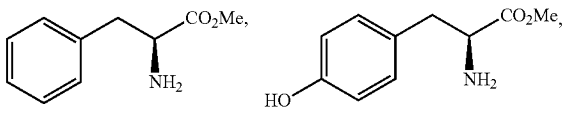

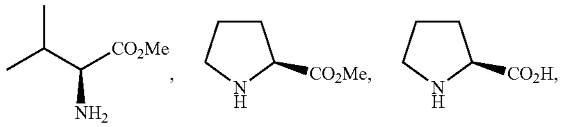

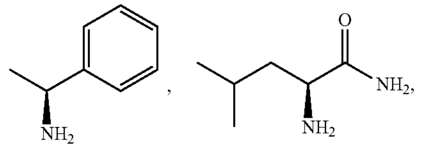

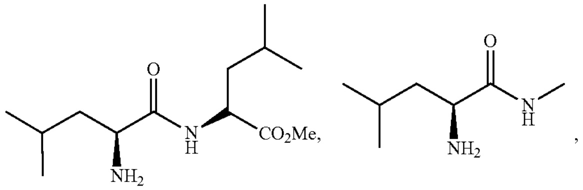

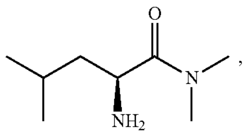

and

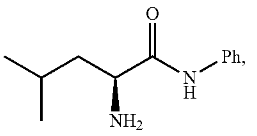

and mixtures thereof.

17. The process according to claim 14, wherein the at least one Base C is selected from the group consisting of lithium carbonate, sodium carbonate, sodium bicarbonate, potassium carbonate, ammonium carbonate, cesium carbonate, lithium dihydrogen phosphate, sodium hydrogen phosphate, sodium dihydrogen phosphate, sodium phosphate, potassium hydrogen phosphate, potassium dihydrogen phosphate, potassium phosphate, ammonium hydrogen phosphate, sodium acetate, ammonium acetate, sodium benzoate, sodium hydrogen sulfate, potassium hydrogen sulfate, potassium fluoride, cesium fluoride, sodium formate, and ammonium formate, and mixtures thereof.

18. The process according to claim 14, further comprising reacting a compound of Formula (I-4) with at least one Base D to form a compound of Formula (I-4[1])

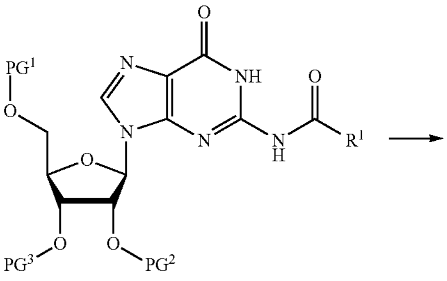

(I-4)

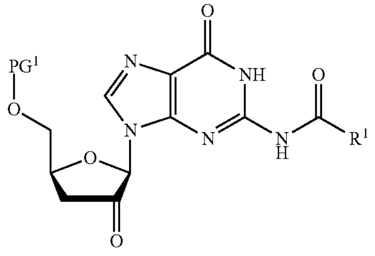

(I-4[1])

wherein protecting group $PG^1$ is selected from the group consisting of isobutyryl, pivaloyl, trityl, tert-butyldiphenylsilyl, and tert-butyldimethylsilyl, protecting group $PG^2$ is selected from the group consisting of isobutyryl, pivaloyl, methanesulfonyl, ethanesulfonyl, benzenesulfonyl, 2-nitrobenzenesulfonyl, 4-nitrobenzensulfonyl, 4-chlorobenzenesulfonyl, 4-fluorobenzenesulfonyl, and p-toluenesulfonyl, and protecting group $PG^3$ is selected from the group consisting of methanesulfonyl, ethanesulfonyl, benzenesulfonyl, 2-nitrobenzenesulfonyl, 4-nitrobenzene sulfonyl, 4-chlorobenzenesulfonyl, 4-fluorobenzenesulfonyl, and p-toluenesulfonyl, and the at least one Base D is selected from the group consisting of lithium hydroxide, lithium methoxide, lithium ethoxide, lithium isopropoxide, lithium tert-butoxide, sodium hydroxide, sodium methoxide, sodium ethoxide, sodium isopropoxide, sodium tert-butoxide, and mixtures thereof; and reacting the compound of Formula (I-4[1]) with at least one Acid A to form the compound of Formula (I-3)

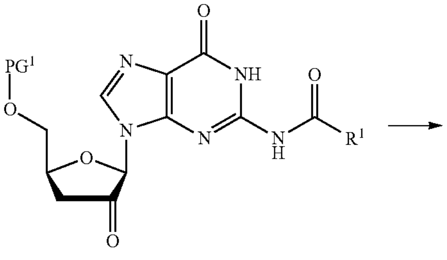

(I-4[1])

-continued

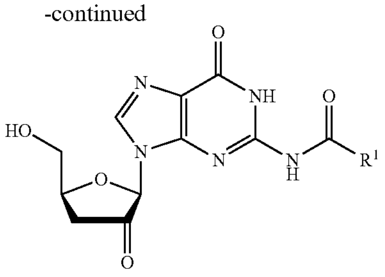

(I-3)

wherein the at least one Acid A is selected from the group consisting of TFA, HCl, $H_2SO_4$, methanesulfonyl hydroxide, para-toluenesulfonyl hydroxide, and mixtures thereof.

19. The process according to claim 18, wherein the reacting the compound of Formula (I-4[1]) with at least one Acid A to form the compound of Formula (I-3) further comprises reacting the compound of Formula (I-4[1]) with at least one Tri-Alkyl Amine A, selected from the group consisting of $N(C_1\text{-}C_{10}\ alkyl)_3$ and mixtures thereof.

20. The process according to claim 18, further comprising selectively functionalizing guanosine to provide a compound of Formula (I-4):

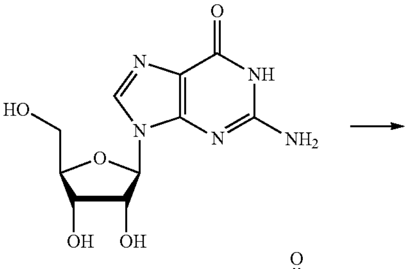

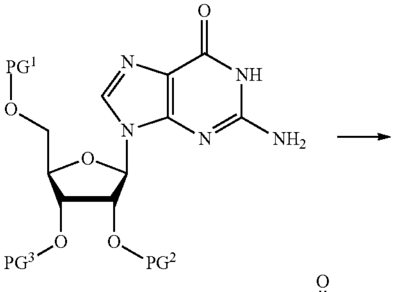

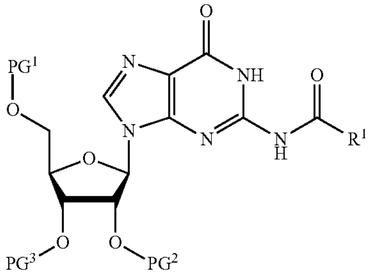

(I-4)

wherein protecting group $PG^1$ is selected from the group consisting of isobutyryl, pivaloyl, trityl, tert-butyldiphenylsilyl, and tert-butyldimethylsilyl; protecting group $PG^2$ is selected from the group consisting of isobutyryl, pivaloyl, methanesulfonyl, ethanesulfonyl, benzenesulfonyl, 2-nitrobenzenesulfonyl, 4-nitrobenzensulfonyl, 4-chlorobenzenesulfonyl, 4-fluorobenzenesulfonyl, and p-toluenesulfonyl;

and protecting group $PG^3$ is selected from the group consisting of methanesulfonyl, ethanesulfonyl, benzenesulfonyl, 2-nitrobenzenesulfonyl, 4-nitrobenzene sulfonyl, 4-chlorobenzenesulfonyl, 4-fluorobenzenesulfonyl, and p-toluenesulfonyl; wherein the selectively functionalizing guanosine to provide a compound of Formula (I-4) comprises:

a) reacting guanosine with $PG^1$-Cl in the presence of at least one Base G, wherein the at least one Base G is selected from the group consisting of pyridine, NMI, 2,6-lutidine, 2,4,6-collidine, DBU, DABCO, tetramethylguanidine, triethylamine, diisopropylethylamine, and mixtures thereof;

b) reacting the product of step a) with $PG^2$-Cl and $PG^3$-Cl in the presence of at least one Base H, wherein the at least one Base His selected from the group consisting of pyridine, NMI, 2,6-lutidine, 2,4,6-collidine, DBU, DABCO, tetramethylguanidine, triethylamine, diisopropylethylamine, and mixtures thereof; and c) reacting the product of step b) with $R^1$—COCl in the presence of at least one Base I, wherein the at least one Base I is selected form the group consisting of pyridine, NMI, 2,6-lutidine, 2,4,6-collidine, DBU, DABCO, tetramethylguanidine, triethylamine, diisopropylethylamine, and mixtures thereof.

21. The process according to claim 1, further comprising reacting the compound of Formula (I-4) with at least one Base E to form a compound of Formula ($I-4^1$)

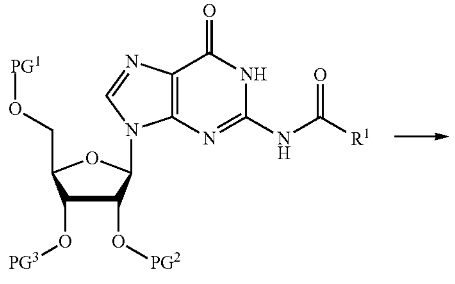

(I-4)

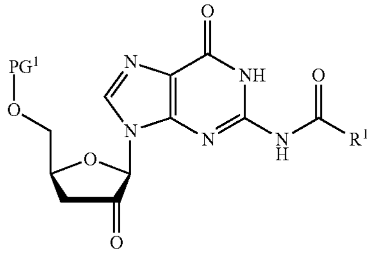

($I-4^1$)

wherein protecting group $PG^1$ is selected from the group consisting of isobutyryl, pivaloyl, trityl, tert-butyldiphenylsilyl, and tert-butyldimethylsilyl chloride, protecting group $PG^2$ is selected from the group consisting of isobutyroyl, pivaloyl, methanesulfonyl, ethanesulfonyl, benzenesulfonyl, 2-nitrobenzenesulfonyl, 4-nitrobenzensulfonyl, 4-chlorobenzenesulfonyl, 4-fluorobenzenesulfonyl, and p-toluenesulfonyl, and protecting group $PG^3$ is selected from the group consisting of methanesulfonyl, ethanesulfonyl, benzenesulfonyl, 2-nitrobenzenesulfonyl, 4-nitrobenzene sulfonyl, 4-chlorobenzenesulfonyl, 4-fluorobenzenesulfonyl, and p-toluenesulfonyl, at least one Base E is selected from the group consisting of lithium hydroxide, lithium methoxide, lithium ethoxide, lithium isopropoxide, lithium tert-butoxide, sodium hydroxide, sodium methoxide, sodium ethoxide, sodium isopropoxide, sodium tert-butoxide, and mixtures thereof;

reacting the compound of Formula ($I-4^1$) with at least one Fluorinating Agent B in the presence of at least one Catalyst C, at least one Base F, and water to form a product, followed by reacting the product with at least one Acid B to form a compound of Formula (I-2):

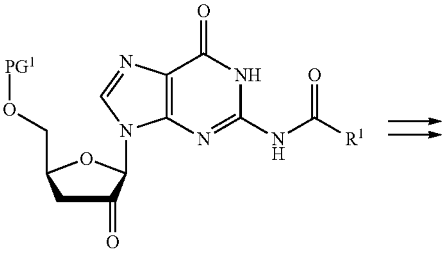

($I-4^1$)

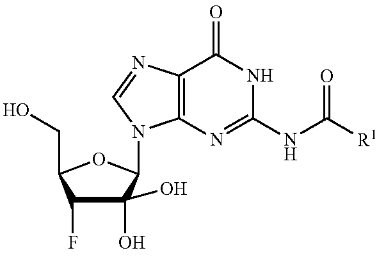

(I-2)

wherein the at least one Fluorinating Agent B is selected from the group consisting of N-fluorobenzenesulfonimide, 1-chloromethyl-4-fluoro-1,4-diazoniabicyclo[2.2.2] octane bis(tetrafluoroborate), 1-fluoro-4-methyl-1,4-diazoniabicyclo[2.2.2] octanebis(tetrafluoroborate), N-fluoropyridinium triflate, and N-fluoropyridinium tetrafluoroborate, and mixtures thereof, the at least one Catalyst C is selected from the group consisting of ($C_1$-$C_8$alkyl) $NH_2$,

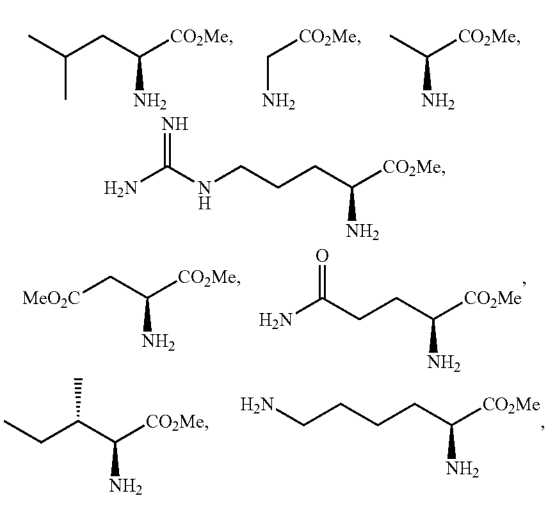

-continued

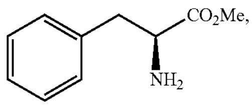 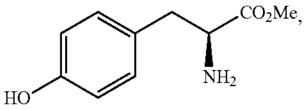

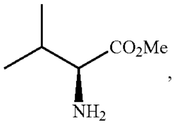 , 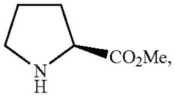 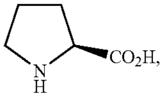

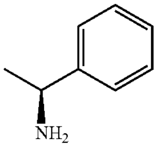 , 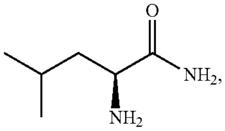

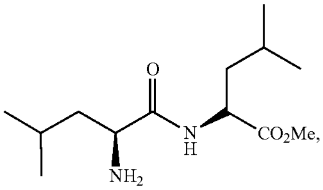 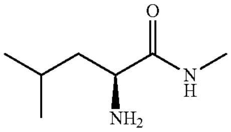 ,

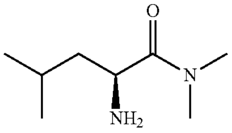 , and 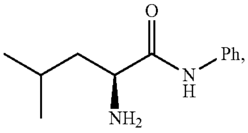

and mixtures thereof, the at least one Base F is selected from the group consisting of lithium carbonate, sodium carbonate, sodium bicarbonate, potassium carbonate, ammonium carbonate, cesium carbonate, lithium dihydrogen phosphate, sodium hydrogen phosphate, sodium dihydrogen phosphate, sodium phosphate, potassium hydrogen phosphate, potassium dihydrogen phosphate, potassium phosphate, ammonium hydrogen phosphate, sodium acetate, ammonium acetate, sodium benzoate, sodium hydrogen sulfate, potassium hydrogen sulfate, potassium fluoride, cesium fluoride, sodium formate, and ammonium formate, and mixtures thereof; wherein the at least one Acid B is selected from the group consisting of TFA, HCl, $H_2SO_4$, methanesulfonyl hydroxide, para-toluenesulfonyl hydroxide, and mixtures thereof; and the at least one Acid B is selected from the group consisting of TFA, HCl, $H_2SO_4$, MsOH, TsOH, and mixtures thereof.

22. A compound selected from the group consisting of:

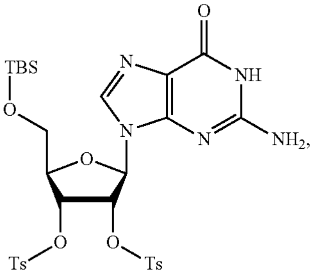

-continued

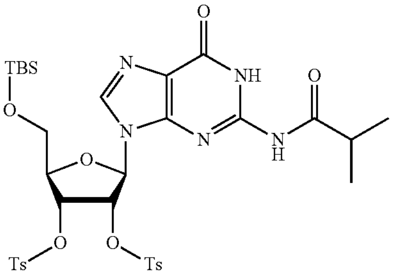 ,

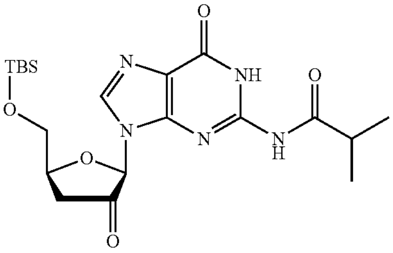 ,

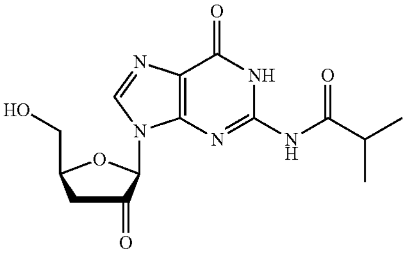 ,

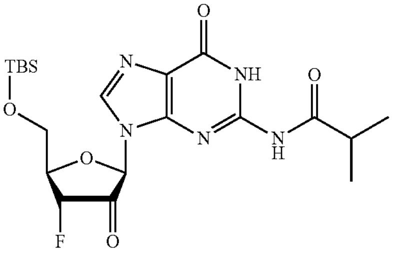 ,

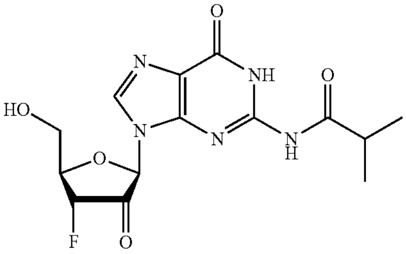 ,

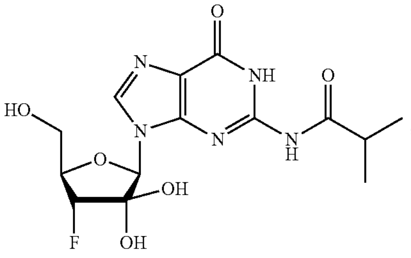 , and

-continued
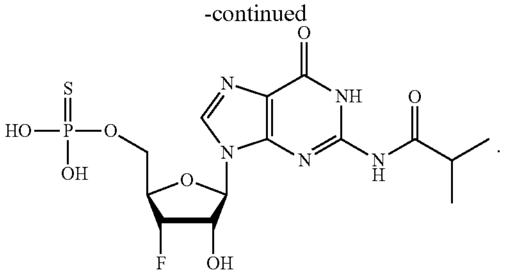
* * * * *

SEQUENCE LISTING

```
<160> NUMBER OF SEQ ID NOS: 11

<210> SEQ ID NO 1
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: His-tagged wild-type ketoreductase

<400> SEQUENCE: 1

Met His His His His His His Asn Lys Thr Ile Val Val Thr Gly Gly
1               5                   10                  15

Thr Lys Gly Ile Gly Arg Ala Ile Val Glu Lys Phe Ala Lys Glu Gly
            20                  25                  30

Phe Thr Val Leu Thr Cys Ala Arg Thr Lys Gly Asp Asn Phe Pro Glu
        35                  40                  45

Asn Val His Phe Phe Lys Ala Asp Leu Ser Lys Lys Val Glu Val Leu
    50                  55                  60

Ala Phe Ala Asp Phe Ile Lys Gln Thr Val Asn Gln Val Asp Ile Leu
65                  70                  75                  80

Val Asn Asn Thr Gly Phe Phe Leu Pro Gly Glu Ile Asn Asn Glu Ala
                85                  90                  95

Glu Gly Thr Leu Glu Ala Met Ile Glu Thr Asn Leu Tyr Ser Ala Tyr
            100                 105                 110

Tyr Leu Thr Arg Ala Leu Val Gly Asp Met Ile Thr Lys Lys Glu Gly
        115                 120                 125

His Ile Phe Asn Ile Cys Ser Thr Ala Ser Ile Thr Ala Tyr Thr Asn
    130                 135                 140

Gly Gly Ser Tyr Cys Ile Ser Lys Phe Ala Leu Leu Gly Met Ser Lys
145                 150                 155                 160

Val Leu Arg Glu Glu Leu Lys Pro His His Val Arg Val Thr Ser Ile
                165                 170                 175

Leu Pro Gly Ala Thr Leu Thr Asp Ser Trp Ala Gly Val Glu Leu Pro
            180                 185                 190

Ala Glu Arg Phe Ile Ala Ser Glu Asp Ile Ala Gln Ile Val Trp Thr
        195                 200                 205

Ala His Cys Leu Pro Ser Thr Thr Val Leu Glu Glu Ile Leu Ile Arg
    210                 215                 220

Pro Gln Leu Gly Asp Leu
225                 230


<210> SEQ ID NO 2
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial  ketoreductase

<400> SEQUENCE: 2

Met His His His His His His Asn Lys Thr Ile Val Val Thr Gly Gly
1               5                   10                  15

Thr Lys Gly Ile Gly Arg Ala Ile Val Glu Lys Phe Ala Lys Glu Gly
            20                  25                  30

Phe Thr Val Leu Thr Cys Ala Arg Thr Lys Gly Asp Asn Phe Pro Glu
        35                  40                  45

Asn Val His Phe Phe Lys Ala Asp Leu Ser Lys Lys Val Glu Val Leu
    50                  55                  60

Ala Phe Ala Asp Phe Ile Lys Gln Thr Val Asn Gln Val Asp Ile Leu
65                  70                  75                  80

Val Asn Asn Thr Gly Phe Phe Leu Pro Gly Glu Ile Asn Asn Glu Ala
```

-continued

```
                85                  90                  95

Glu Gly Thr Leu Glu Ala Met Ile Glu Thr Asn Leu Tyr Ser Ala Tyr
            100                 105                 110

Tyr Leu Thr Arg Ala Leu Val Gly Asp Met Ile Thr Lys Lys Glu Gly
        115                 120                 125

His Ile Phe Asn Ile Cys Ser Thr Ala Ser Ile Thr Ala Tyr Thr Asn
    130                 135                 140

Gly Gly Ser Tyr Cys Ile Ser Lys Phe Ala Leu Leu Gly Met Ser Lys
145                 150                 155                 160

Val Leu Arg Glu Glu Leu Lys Pro His His Val Arg Val Thr Ser Ile
                165                 170                 175

Leu Pro Gly Ala Thr Leu Asn Asp Ser Trp Ala Gly Val Glu Leu Pro
            180                 185                 190

Ala Glu Arg Phe Ile Ala Ser Glu Asp Ile Ala Gln Ile Val Trp Thr
        195                 200                 205

Ala His Cys Leu Pro Ser Thr Thr Val Leu Glu Glu Ile Leu Ile Arg
    210                 215                 220

Pro Gln Leu Gly Asp Leu
225                 230


<210> SEQ ID NO 3
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial ketoreductase

<400> SEQUENCE: 3

Met His His His His His His Asn Lys Thr Ile Val Val Thr Gly Gly
1               5                   10                  15

Thr Lys Gly Ile Gly Arg Ala Ile Val Glu Lys Phe Ala Lys Glu Gly
            20                  25                  30

Phe Thr Val Leu Thr Cys Ala Arg Thr Lys Gly Asp Asn Phe Pro Glu
        35                  40                  45

Asn Val His Phe Phe Lys Ala Asp Leu Ser Lys Lys Val Glu Val Leu
    50                  55                  60

Ala Phe Ala Asp Phe Ile Lys Gln Thr Val Asn Gln Val Asp Ile Leu
65                  70                  75                  80

Val Asn Asn Thr Gly Phe Phe Leu Pro Gly Glu Ile Asn Asn Glu Ala
                85                  90                  95

Glu Gly Thr Leu Glu Ala Met Ile Glu Thr Asn Leu Tyr Ser Ala Tyr
            100                 105                 110

Tyr Leu Thr Arg Ala Leu Val Gly Asp Met Ile Thr Lys Lys Glu Gly
        115                 120                 125

His Ile Phe Asn Ile Cys Ser Tyr Ala Ser Ile Thr Ala Tyr Thr Ser
    130                 135                 140

Gly Gly Ser Tyr Cys Ile Ser Lys Phe Ala Leu Leu Gly Met Ser Lys
145                 150                 155                 160

Val Leu Arg Glu Glu Leu Lys Pro His His Val Arg Val Thr Ser Ile
                165                 170                 175

Leu Pro Gly Ala Thr Leu Asn Asp Ser Trp Ala Lys Val Glu Leu Pro
            180                 185                 190

Ala Glu Arg Phe Ile Ala Ser Glu Asp Ile Ala Gln Ile Val Trp Thr
```

```
        195                 200                 205

Ala His Cys Leu Pro Ser Thr Thr Val Leu Glu Glu Ile Leu Ile Arg
    210                 215                 220

Pro Gln Leu Gly Asp Leu
225                 230
```

<210> SEQ ID NO 4
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial ketoreductase

<400> SEQUENCE: 4

```
Met His His His His His Pro Ala Thr Ile Val Val Thr Gly Gly Thr
1               5                   10                  15

Lys Gly Ile Gly Arg Ala Ile Val Glu Lys Phe Ala Lys Glu Gly Phe
            20                  25                  30

Thr Val Leu Thr Cys Ala Arg Thr Lys Gly Asp Asn Phe Pro Glu Asn
        35                  40                  45

Val His Phe Phe Lys Ala Asp Leu Ser Lys Lys Val Glu Val Leu Ala
    50                  55                  60

Phe Ala Asp Phe Ile Lys Gln Thr Val Asn Gln Val Asp Ile Leu Val
65                  70                  75                  80

Asn Asn Thr Gly Phe Phe Leu Pro Gly Glu Ile Asn Asn Glu Ala Glu
                85                  90                  95

Gly Thr Leu Glu Ala Met Ile Glu Thr Asn Leu Tyr Ser Ala Tyr Tyr
            100                 105                 110

Leu Thr Arg Ala Leu Val Gly Asp Met Ile Thr Lys Lys Glu Gly His
        115                 120                 125

Ile Phe Asn Ile Cys Ser Tyr Ala Ser Ile Thr Ala Tyr Thr Ser Gly
    130                 135                 140

Gly Ser Tyr Cys Ile Ser Lys Thr Ala Leu Leu Gly Met Ser Lys Val
145                 150                 155                 160

Leu Arg Glu Glu Leu Lys Pro His His Val Arg Val Thr Ser Ile Leu
                165                 170                 175

Pro Gly Ala Thr Leu Asn Asp Ser Trp Ala Lys Val Glu Leu Pro Ala
            180                 185                 190

Glu Trp Phe Ile Ala Ser Glu Asp Ile Ala Gln Ile Val Trp Thr Ala
        195                 200                 205

His Cys Leu Pro Ser Thr Thr Val Leu Glu Glu Ile Leu Ile Arg Pro
    210                 215                 220

Gln Leu Gly Asp Leu
225
```

<210> SEQ ID NO 5
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial ketoreductase

<400> SEQUENCE: 5

```
Met His His His His His Pro Ala Thr Ile Val Val Thr Gly Gly Thr
1               5                   10                  15

Lys Gly Ile Gly Arg Ala Ile Val Glu Lys Phe Ala Lys Glu Gly Phe
            20                  25                  30

Thr Val Leu Thr Cys Ala Arg Thr Lys Gly Asp Asn Phe Pro Glu Asn
        35                  40                  45

Val His Phe Phe Lys Ala Asp Leu Ser Lys Lys Val Glu Val Leu Ala
    50                  55                  60

Phe Ala Asp Phe Ile Lys Gln Thr Val Asn Gln Val Asp Ile Leu Val
65                  70                  75                  80

Asn Asn Thr Gly Trp Phe Leu Pro Gly Glu Ile Asn Asn Glu Ala Glu
                85                  90                  95

Gly Thr Leu Glu Ala Met Ile Glu Thr Asn Leu Tyr Ser Ala Tyr Tyr
            100                 105                 110

Leu Thr Arg Ala Leu Val Gly Asp Met Ile Thr Lys Lys Glu Gly His
        115                 120                 125

Ile Phe Asn Ile Cys Ser Tyr Ala Ser Ile Val Pro Tyr Thr Ser Gly
    130                 135                 140

Gly Ser Tyr Cys Ile Ser Lys Thr Ala Gln Leu Gly Met Ser Lys Val
145                 150                 155                 160

Leu Arg Glu Glu Leu Lys Pro His His Val Arg Val Thr Ser Ile Leu
                165                 170                 175

Pro Gly Ala Val Leu Asn Asp Ser Trp Ala Lys Val Glu Leu Pro Ala
            180                 185                 190

Glu Trp Phe Ile Ala Ser Glu Asp Ile Ala Gln Ile Val Trp Thr Ala
        195                 200                 205

His Cys Leu Pro Ser Thr Thr Val Leu Glu Glu Ile Leu Ile Arg Pro
    210                 215                 220

Gln Leu Gly Asp Leu
225


<210> SEQ ID NO 6
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial ketoreductase

<400> SEQUENCE: 6

Met His His His His His Pro Ala Thr Ile Val Val Thr Gly Gly Thr
1               5                   10                  15

Lys Gly Ile Gly Arg Ala Ile Val Glu Lys Phe Ala Lys Glu Gly Phe
            20                  25                  30

Thr Val Leu Thr Cys Ala Arg Thr Lys Gly Asp Asn Phe Pro Glu Asn
        35                  40                  45

Val His Phe Phe Lys Ala Asp Leu Ser Lys Lys Val Glu Val Leu Ala
    50                  55                  60

Phe Ala Asp Phe Ile Lys Gln Thr Val Asn Gln Val Asp Ile Leu Val
65                  70                  75                  80

Asn Asn Thr Gly Trp Phe Leu Pro Gly Glu Ile Asn Asn Glu Ala Glu
                85                  90                  95

Gly Thr Leu Glu Ala Met Ile Glu Thr Asn Leu Tyr Ser Ala Tyr Tyr
            100                 105                 110
```

```
Leu Thr Arg Ala Leu Val Gly Asp Met Ile Thr Lys Lys Glu Gly His
        115                 120                 125

Ile Phe Asn Ile Cys Ser Tyr Ala Ser Ile Val Pro Tyr Thr Ser Gly
    130                 135                 140

Gly Ser Tyr Cys Ile Ser Lys Thr Ala Gln Leu Gly Met Ser Lys Val
145                 150                 155                 160

Leu Arg Glu Glu Leu Lys Pro His His Val Arg Val Thr Ser Ile Leu
                165                 170                 175

Pro Gly Ala Val Leu Asn Asp Ser Trp Ala Lys Val Glu Leu Pro Ala
            180                 185                 190

Glu Leu Phe Ile Ala Pro Glu Asp Ile Ala Gln Ile Val Trp Thr Ala
        195                 200                 205

His Cys Leu Pro Ser Thr Thr Val Leu Glu Glu Ile Leu Ile Arg Pro
    210                 215                 220

Gln Thr Gly Asp Leu
225


<210> SEQ ID NO 7
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial ketoreductase

<400> SEQUENCE: 7

Met His His His His His Pro Ala Thr Ile Val Val Thr Gly Gly Thr
1               5                   10                  15

Lys Gly Ile Gly Arg Ala Ile Val Glu Lys Phe Ala Lys Glu Gly Phe
            20                  25                  30

Thr Val Leu Thr Cys Ala Arg Thr Ala Gly Asp Asn Phe Pro Glu Asn
        35                  40                  45

Val His Phe Phe Lys Ala Asp Leu Ser Lys Lys Val Glu Val Leu Ala
    50                  55                  60

Phe Ala Asp Phe Ile Lys Gln Thr Val Asn Gln Val Asp Ile Leu Val
65                  70                  75                  80

Asn Asn Thr Gly Trp Phe Leu Pro Gly Glu Ile Asn Asn Glu Glu Glu
                85                  90                  95

Gly Thr Leu Glu Ala Met Ile Glu Thr Asn Leu Tyr Ser Ala Tyr Tyr
            100                 105                 110

Leu Thr Arg Ala Leu Val Gly Asp Met Ile Thr Lys Lys Glu Gly His
        115                 120                 125

Ile Phe Asn Ile Cys Ser Tyr Ala Ser Ile Val Pro Tyr Thr Ser Gly
    130                 135                 140

Gly Ser Tyr Cys Ile Ser Lys Thr Ala Gln Leu Gly Met Ser Lys Val
145                 150                 155                 160

Leu Arg Glu Glu Leu Lys Pro His His Val Arg Val Thr Ser Ile Leu
                165                 170                 175

Pro Gly Ala Val Leu Asn Asp Ser Trp Ala Lys Val Glu Leu Pro Ala
            180                 185                 190

Glu Leu Phe Ile Ala Pro Glu Asp Ile Ala Gln Ile Val Trp Thr Ala
        195                 200                 205

His Cys Leu Pro Ser Thr Thr Val Leu Glu Glu Ile Leu Ile Arg Pro
    210                 215                 220
```

```
Gln Glu Gly Asp Leu
225


<210> SEQ ID NO 8
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial ketoreductase

<400> SEQUENCE: 8

Met His His His His His Pro Ala Thr Ile Val Val Thr Gly Gly Thr
1               5                   10                  15

Lys Gly Ile Gly Arg Ala Ile Val Glu Lys Phe Ala Lys Glu Gly Phe
            20                  25                  30

Thr Val Leu Thr Cys Ala Arg Thr Ala Gly Asp Asn Phe Pro Glu Asn
        35                  40                  45

Val His Phe Phe Lys Ala Asp Leu Ser Lys Lys Val Glu Val Leu Ala
    50                  55                  60

Phe Ala Asp Phe Ile Lys Gln Thr Val Asn Gln Val Asp Ile Leu Val
65                  70                  75                  80

Asn Asn Thr Gly His Phe Leu Pro Gly Glu Ile Asn Asn Glu Glu Glu
                85                  90                  95

Gly Thr Leu Glu Ala Met Ile Glu Thr Asn Leu Tyr Ser Ala Tyr Tyr
            100                 105                 110

Leu Thr Arg Ala Leu Val Gly Asp Met Ile Thr Lys Lys Glu Gly His
        115                 120                 125

Ile Phe Asn Ile Cys Ser Tyr Ala Ser Ile Val Pro Tyr Thr Ser Gly
    130                 135                 140

Gly Ser Tyr Cys Ile Ser Lys Thr Ala Glu Leu Gly Met Ser Lys Val
145                 150                 155                 160

Leu Arg Glu Glu Leu Lys Pro His His Val Arg Val Thr Ser Ile Leu
                165                 170                 175

Pro Gly Ala Val Leu Asn Asp Ser Trp Ala Lys Ala Glu Leu Pro Ala
            180                 185                 190

Glu Leu Phe Ile Ala Pro Glu Asp Ile Ala Gln Ile Val Trp Thr Ala
        195                 200                 205

His Cys Leu Pro Ser Thr Thr Val Leu Glu Glu Ile Leu Ile Arg Pro
    210                 215                 220

Gln Glu Gly Asp Leu
225


<210> SEQ ID NO 9
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial ketoreductase

<400> SEQUENCE: 9

Met His His His His His Pro Ala Thr Ile Val Val Thr Gly Gly Thr
1               5                   10                  15

Lys Gly Ile Gly Arg Ala Ile Val Glu Lys Phe Ala Lys Glu Gly Phe
            20                  25                  30
```

```
Thr Val Leu Thr Cys Ala Arg Thr Ala Gly Asp Asn Phe Pro Glu Asn
        35                  40                  45

Val His Phe Phe Lys Ala Asp Leu Ser Lys Lys Val Glu Val Leu Ala
    50                  55                  60

Phe Ala Asp Phe Ile Lys Gln Thr Val Asn Gln Val Asp Ile Leu Val
65                  70                  75                  80

Asn Asn Thr Gly His Phe Leu Pro Gly Glu Ile Asn Asn Glu Glu Glu
                85                  90                  95

Gly Thr Leu Glu Ala Met Ile Glu Thr Asn Leu Tyr Ser Ala Tyr Tyr
            100                 105                 110

Leu Thr Arg Ala Leu Val Gly Asp Met Ile Thr Lys Lys Glu Gly His
        115                 120                 125

Ile Phe Asn Ile Cys Ser Tyr Ala Ser Ile Val Pro Tyr Thr Ser Gly
    130                 135                 140

Gly Ser Tyr Cys Ile Ser Lys Thr Ala Glu Leu Ala Met Ser Arg Val
145                 150                 155                 160

Leu Arg Glu Glu Leu Lys Pro His His Val Arg Val Thr Ser Ile Leu
                165                 170                 175

Pro Gly Ala Val Leu Asn Asp Asn Trp Ala Lys Ala Glu Leu Pro Ala
            180                 185                 190

Glu Leu Phe Ile Ala Pro Glu Asp Ile Ala Gln Ile Val Trp Thr Ala
        195                 200                 205

His Cys Leu Pro Ser Thr Thr Val Leu Glu Glu Ile Leu Ile Arg Pro
    210                 215                 220

Thr Glu Gly Asp Leu
225


<210> SEQ ID NO 10
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial ketoreductase

<400> SEQUENCE: 10

Met His His His His His Pro Ala Thr Ile Val Val Thr Gly Gly Thr
1               5                   10                  15

Lys Gly Ile Gly Arg Ala Ile Val Glu Lys Phe Ala Lys Glu Gly Phe
            20                  25                  30

Thr Val Leu Thr Cys Ala Arg Thr Ala Gly Asp Asn Phe Pro Glu Asn
        35                  40                  45

Val His Phe Phe Lys Ala Asp Leu Ser Lys Lys Val Glu Val Leu Ala
    50                  55                  60

Phe Ala Asp Phe Ile Lys Ala Thr Val Asn Gln Val Asp Ile Leu Val
65                  70                  75                  80

Asn Asn Thr Gly His Phe Leu Pro Gly Glu Ile Asn Asn Glu Glu Glu
                85                  90                  95

Gly Thr Leu Glu Ala Met Ile Glu Thr Asn Leu Tyr Ser Ala Tyr Tyr
            100                 105                 110

Leu Thr Arg Ala Leu Val Gly Asp Met Ile Thr Lys Lys Glu Gly His
        115                 120                 125

Ile Phe Asn Ile Cys Ser Tyr Ala Ser Ile Val Pro Tyr Thr Pro Gly
    130                 135                 140
```

-continued

```
Gly Ser Tyr Cys Ile Ser Lys Thr Ala Glu Leu Ala Met Ser Arg Val
145                 150                 155                 160

Leu Arg Glu Glu Leu Lys Pro His His Val Arg Val Thr Ser Ile Leu
                165                 170                 175

Pro Gly Ala Val Leu Asn Asp Asn Trp Ala Lys Ala Glu Leu Pro Ala
            180                 185                 190

Glu Leu Phe Ile Ala Pro Glu Asp Ile Ala Gln Ile Val Trp Thr Ala
        195                 200                 205

His Cys Leu Pro Ser Thr Thr Val Leu Glu Glu Ile Leu Ile Arg Pro
    210                 215                 220

Thr Glu Gly Asp Leu
225


<210> SEQ ID NO 11
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Artificial ketoreductase

<400> SEQUENCE: 11

Met His His His His His Pro Ala Thr Ile Val Val Thr Gly Gly Thr
1               5                   10                  15

Lys Gly Ile Gly Arg Ala Ile Val Glu Lys Phe Ala Lys Glu Gly Phe
            20                  25                  30

Thr Val Leu Thr Cys Ala Arg Thr Ala Gly Asp Asn Phe Pro Glu Asn
        35                  40                  45

Val His Phe Phe Lys Ala Asp Leu Ser Lys Lys Val Glu Val Leu Ala
    50                  55                  60

Phe Ala Asp Phe Ile Lys Ala Thr Val Asn Gln Val Asp Ile Leu Val
65                  70                  75                  80

Asn Asn Thr Gly His Phe Leu Pro Gly Glu Ile Asn Asn Glu Glu Glu
                85                  90                  95

Gly Thr Leu Glu Ala Met Ile Glu Thr Asn Leu Tyr Ser Ala Tyr Tyr
            100                 105                 110

Leu Thr Arg Ala Leu Val Gly Asp Met Ile Thr Lys Lys Glu Gly His
        115                 120                 125

Ile Phe Asn Ile Cys Ser Tyr Ala Ser Ile Val Pro Tyr Thr Ser Gly
    130                 135                 140

Gly Ser Tyr Cys Ile Ser Lys Thr Ala Met Leu Ala Met Ser Arg Val
145                 150                 155                 160

Leu Arg Glu Glu Leu Lys Pro His His Val Arg Val Thr Ser Ile Leu
                165                 170                 175

Pro Gly Ala Val Leu Asn Asp Asn Trp Ala Lys Ala Glu Leu Pro Ala
            180                 185                 190

Glu Leu Phe Ile Ala Pro Glu Asp Ile Ala Gln Ile Val Trp Thr Ala
        195                 200                 205

His Cys Leu Pro Ser Thr Thr Val Leu Glu Glu Ile Leu Ile Arg Pro
    210                 215                 220

Thr Glu Gly Asp Leu
225
```